US011542536B2

(12) United States Patent
Prakash et al.

(10) Patent No.: US 11,542,536 B2
(45) Date of Patent: Jan. 3, 2023

(54) PREPARING NOVEL STEVIOL GLYCOSIDES BY BIOCONVERSION

(71) Applicant: The Coca-Cola Company, Atlanta, GA (US)

(72) Inventors: Indra Prakash, Alpharetta, GA (US); Gil Ma, Atlanta, GA (US)

(73) Assignee: The Coca-Cola Company, Atlanta, GA (US)

( * ) Notice: Subject to any disclaimer, the term of this patent is extended or adjusted under 35 U.S.C. 154(b) by 854 days.

(21) Appl. No.: 16/469,439

(22) PCT Filed: Dec. 14, 2017

(86) PCT No.: PCT/US2017/066400
§ 371 (c)(1),
(2) Date: Jun. 13, 2019

(87) PCT Pub. No.: WO2018/112189
PCT Pub. Date: Jun. 21, 2018

(65) Prior Publication Data
US 2020/0277640 A1 Sep. 3, 2020

Related U.S. Application Data

(60) Provisional application No. 62/434,125, filed on Dec. 14, 2016.

(51) Int. Cl.
C12P 19/56 (2006.01)
A23L 27/30 (2016.01)
A23L 2/60 (2006.01)
C07H 15/256 (2006.01)

(52) U.S. Cl.
CPC ............... *C12P 19/56* (2013.01); *A23L 2/60* (2013.01); *A23L 27/36* (2016.08); *C07H 15/256* (2013.01); *C12Y 204/01005* (2013.01); *A23V 2002/00* (2013.01)

(58) Field of Classification Search
CPC . C12P 19/56; A23L 2/60; A23L 27/36; C07H 15/256; C12Y 204/01005; A23V 2002/00
See application file for complete search history.

(56) References Cited

U.S. PATENT DOCUMENTS

2016/0198748 A1   7/2016   Prakash et al.

FOREIGN PATENT DOCUMENTS

| WO | WO 2016/043926 | 3/2016 |
| WO | WO 2016/086233 | 6/2016 |
| WO | WO 02/064810 | 8/2016 |
| WO | WO 2016/144175 | 9/2016 |

OTHER PUBLICATIONS

International Search Report from PCT/US2017/066400, dated Feb. 22, 2018.
Ko, J. et al. Glucosyl Rubusosides By Dextransucrases Improve the Quality of Taste and Sweetness. J. Microbiol. Biotechnol. Jan. 26, 2016, vol. 26, pp. 493-497.

*Primary Examiner* — Donald R Spamer
*Assistant Examiner* — Jeffrey D Benson
(74) *Attorney, Agent, or Firm* — King & Spalding

(57) ABSTRACT

Methods of preparing novel steviol glycosides are described herein. The methods utilize biocatalysts for converting a starting steviol glycoside to a target steviol glycoside. Compositions and consumables comprising said novel steviol glycosides as well as methods of purifying and using said novel steviol glycosides, are also provided.

3 Claims, 18 Drawing Sheets

PREPARING NOVEL STEVIOL GLYCOSIDES BY BIOCONVERSION

CROSS REFERENCE TO RELATED APPLICATIONS

This application is a national phase application under 35 U.S.C. § 371 of International Application No. PCT/US2017/066400, filed Dec. 14, 2017, which claims priority to U.S. Provisional Patent Application No. 62/434,125, filed Dec. 14, 2016. The contents of each of the above-identified applications is fully incorporated herein by reference.

FIELD OF THE INVENTION

The present invention relates to a biocatalytic process for preparing novel target steviol glycosides from starting steviol glycosides. The present invention also relates to the use of said novel target steviol glycosides as sweeteners. The present invention also relates to compositions and consumables comprising said novel target steviol glycosides.

BACKGROUND OF THE INVENTION

High intensity sweeteners possess a sweetness level that is many times greater than the sweetness level of sucrose. They are essentially non-caloric and are commonly used in diet and reduced-calorie products, including foods and beverages. High intensity sweeteners do not elicit a glycemic response, making them suitable for use in products targeted to diabetics and others interested in controlling for their intake of carbohydrates.

Steviol glycosides are a class of compounds found in the leaves of *Stevia rebaudiana* Bertoni, a perennial shrub of the Asteraceae (Compositae) family native to certain regions of South America. They are characterized structurally by a single base, steviol, differing by the presence of carbohydrate residues at positions C13 and C19. They accumulate in *Stevia* leaves, composing approximately 10%-20% of the total dry weight. On a dry weight basis, the four major glycosides found in the leaves of *Stevia* typically include stevioside (9.1%), rebaudioside A (3.8%), rebaudioside C (0.6-1.0%) and dulcoside A (0.3%). Other known steviol glycosides include rebaudioside B, C, D, E, F and M, steviolbioside and rubusoside.

Although methods are known for preparing steviol glycosides from *Stevia rebaudiana*, many of these methods are unsuitable for use commercially.

Accordingly, there remains a need for simple, efficient and economical methods for preparing compositions comprising steviol glycosides, including purified steviol glycoside compositions.

SUMMARY OF THE INVENTION

The present invention provides a biocatalytic process for preparing a composition comprising a target steviol glycoside comprising contacting a medium comprising a starting composition comprising a starting steviol glycoside with a biocatalyst, thereby producing a composition comprising a target steviol glycoside.

In one embodiment, the biocatalyst is an enzyme, or a cell comprising one or more enzymes, capable of converting the starting steviol glycoside to the target steviol glycoside. The biocatalyst can be located on the surface of and/or inside the cell. The biocatalyst can be provided in the form of a whole cell suspension, a crude lysate or as purified enzyme(s). The biocatalyst can be in free form or immobilized to a solid support made from inorganic or organic materials.

In one aspect, the present invention is a method for preparing target steviol glycoside CC-00326 ((13-[(2-O-β-D-glucopyranosyl-3-O-β-D-glucopyranosyl-β-D-glucopyranosyl)oxy]ent-kaur-16-en-19-oic acid-[(6-O-α-D-glucopyranosyl-β-D-glucopyranosyl) ester])) comprising contacting a medium comprising a composition comprising starting steviol glycoside rebaudioside A with Dextransucrase from *Leuconostoc Lactis* (DS-LeuLac) to produce a composition comprising target steviol glycoside CC-00326:

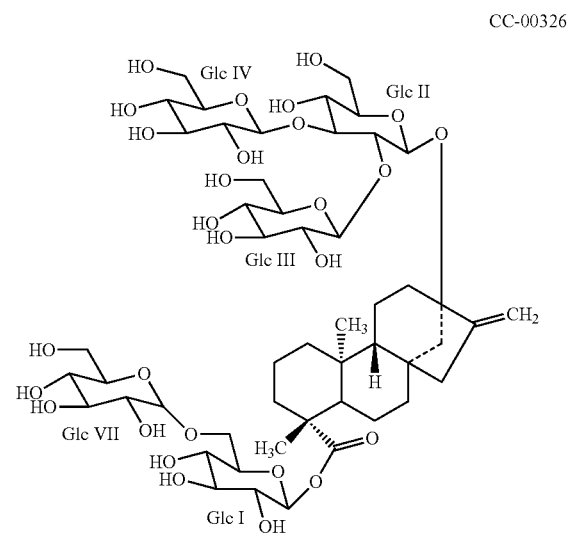

In another aspect, the present invention is a method for preparing target steviol glycoside CC-00342 ((13-[(2-O-β-D-glucopyranosyl-3-O-β-D-glucopyranosyl)-β-D-glucopyranosyl)oxy]ent-kaur-16-en-19-oic acid-[(2-O-β-D-glucopyranosyl-6-O-α-D-glucopyranosyl)-β-D-glucopyranosyl) ester]) comprising contacting a medium comprising a composition comprising starting steviol glycoside CC-00326 with EUGT11 to produce a composition comprising target steviol glycoside CC-00342:

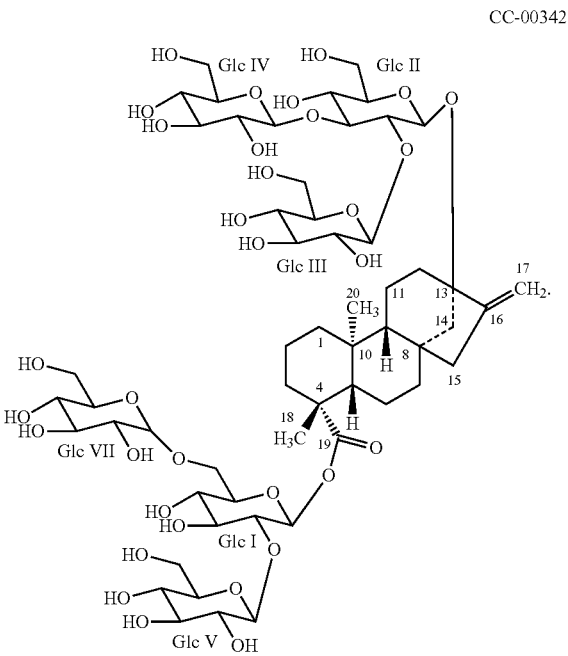

In another aspect, the present invention is a method for preparing target steviol glycoside CC-00345 ((13-[(2-O-β-D-glucopyranosyl-3-O-β-D-glucopyranosyl)-β-D-glucopyranosyl)oxy]ent-kaur-16-en-19-oic acid-[(2-O-β-D-glucopyranosyl-3-O-β-D-glucopyranosyl-6-O-α-D-glucopyranosyl)-β-D-glucopyranosyl) ester]) comprising contacting a medium comprising a composition comprising starting steviol glycoside CC-00342 with UGT76G1 to produce a composition comprising CC-00345:

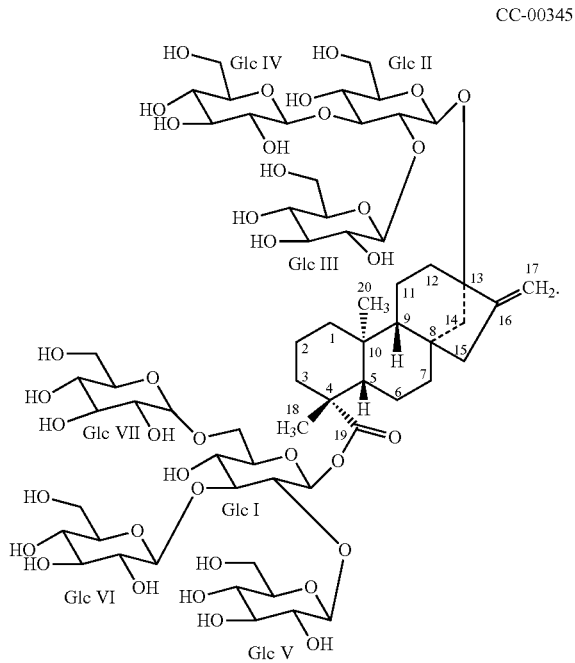

CC-00345

In another aspect, the present invention is a method of preparing target steviol glycoside CC-00337 ((13-[(2-O-β-D-glucopyranosyl-3-O-β-D-glucopyranosyl)-β-D-glucopyranosyl)oxy]ent-kaur-16-en-19-oic acid-[(2-O-β-D-glucopyranosyl-(3-O-α-D-glucopyranosyl)-β-D-glucopyranosyl) ester]) comprising contacting a medium comprising a composition comprising starting steviol glycoside rebaudioside D with Dextransucrase ATCC 11449 to produce a composition comprising target steviol glycoside CC-00337:

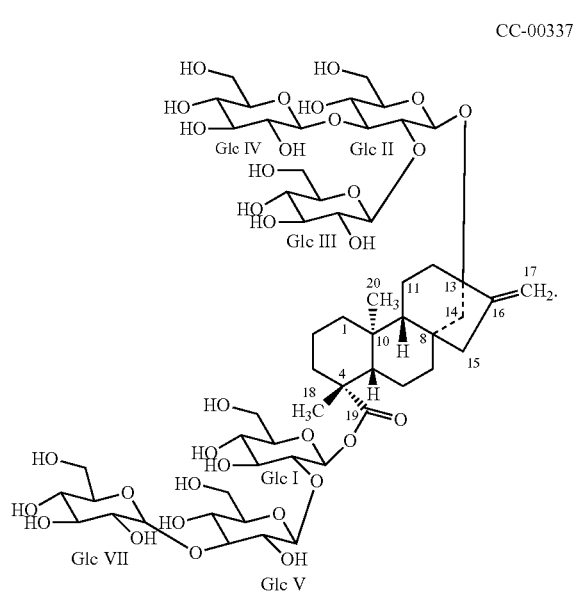

CC-00337

The composition comprising the target steviol glycoside typically includes reaction by-products, excess reagents, unreacted starting material and other undesirable materials. Accordingly, in some embodiments, the methods disclosed herein further comprise separating the target steviol glycoside from at least some of these undesirable materials in the composition comprising the target steviol glycoside composition to provide a separated target steviol glycoside composition. In further embodiments, the separated target steviol glycoside composition is further purified to provide a purified steviol glycoside composition.

In another aspect, the present invention is an isolated and purified target steviol glycoside described herein.

In yet another aspect, the present invention is a composition comprising at least one target steviol glycoside described herein, and the target steviol glycoside is sweet. In exemplary embodiments, the composition further comprises at least one additional sweetener and/or additive and/or functional ingredient.

In still another aspect, the present invention is a consumable comprising at least one target steviol glycoside described herein. Exemplary consumables include, but are not limited to, pharmaceutical compositions, edible gel mixes and compositions, dental compositions, foodstuffs (confections, condiments, chewing gum, cereal compositions baked goods dairy products, and tabletop sweetener compositions), beverages and beverage products. In a particular embodiment, the consumable is a beverage.

In a further aspect, the present invention is a method of preparing a sweetened consumable comprising: (i) providing a consumable and (ii) adding at least one target steviol glycoside of the present invention to the consumable to provide a sweetened consumable.

BRIEF DESCRIPTION OF THE DRAWINGS

The accompanying drawings are included to provide a further understanding of the invention. The drawings illustrate embodiments of the invention and together with the description serve to explain the principles of the embodiments of the invention.

DETAILED DESCRIPTION

Figure 1:
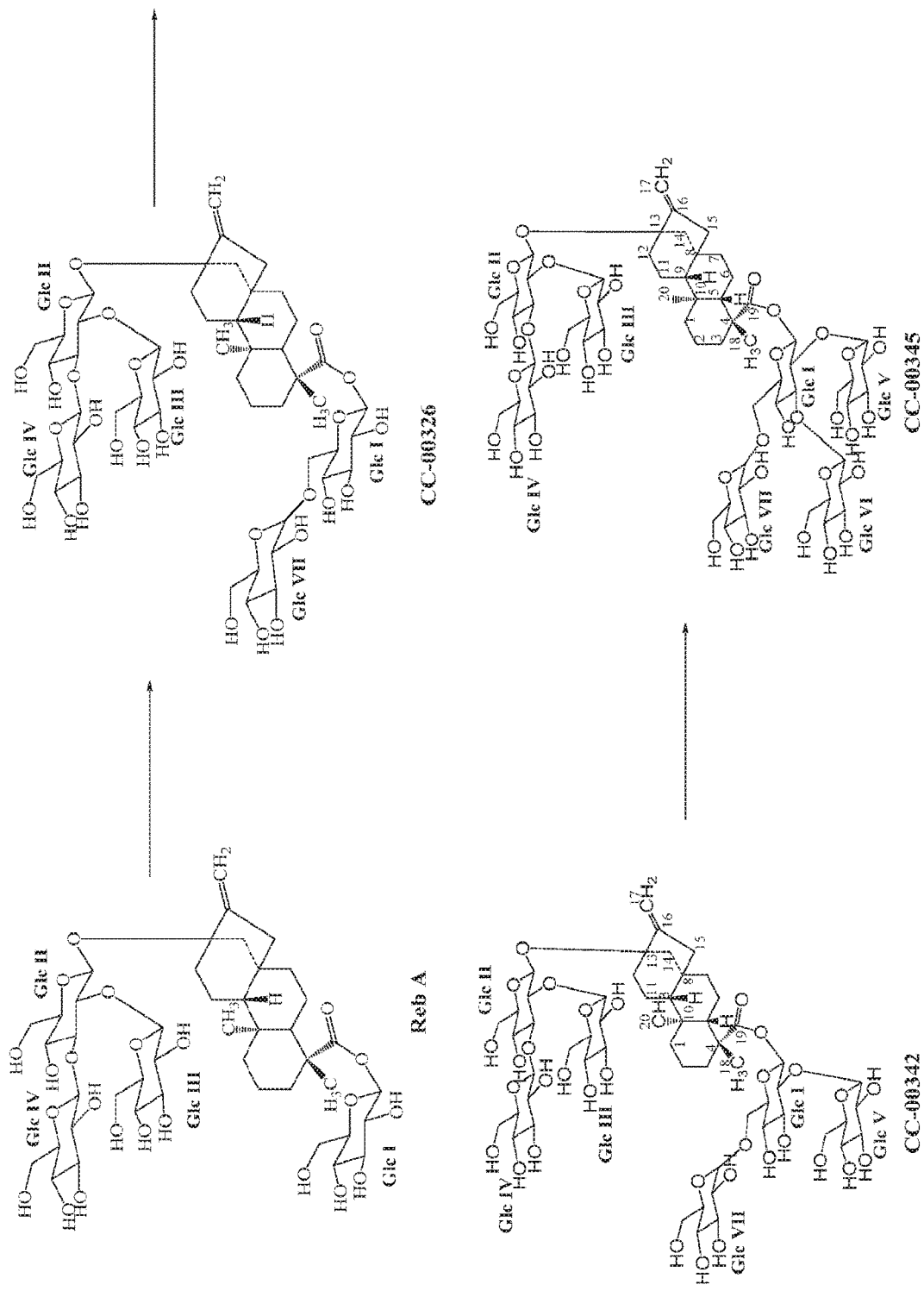
FIG. 1 shows the biocatalytic production of CC-00326, CC-00342 and CC-00345 from rebaudioside A.
Figure 2:
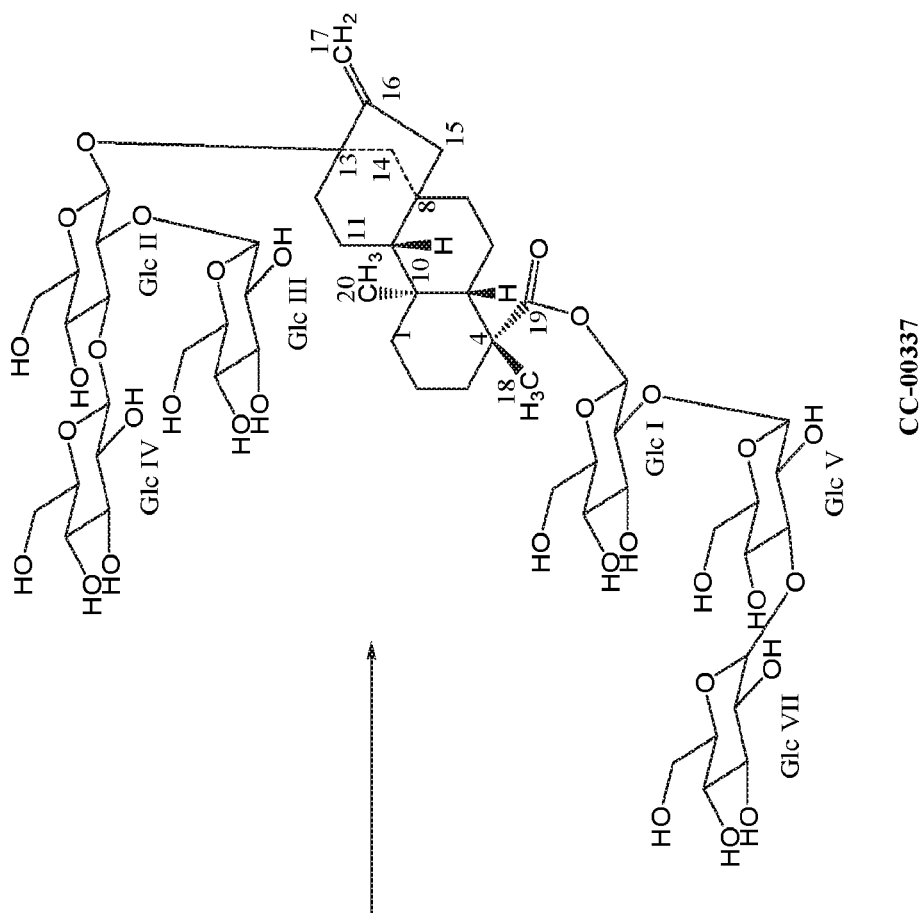
FIG. 2 shows the biocatalytic production of CC-00337 from rebaudioside D.
Figure 2:
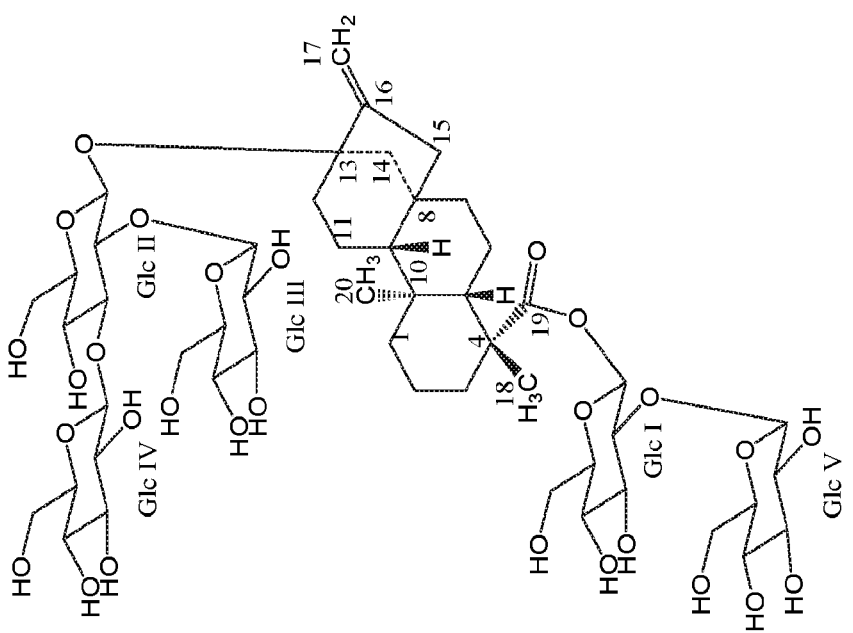

The present invention provides a biocatalytic process for preparing a composition comprising a target steviol glycoside by contacting a medium comprising a starting composition comprising a starting steviol glycoside with a biocatalyst, thereby producing a composition comprising a target steviol glycoside.

As used herein, "starting composition" refers to any composition containing the starting or first steviol glycoside, i.e. the glycoside to be transformed into the target steviol glycoside. The starting composition may be synthetic or purified (partially or entirely), commercially available or prepared.

As used here, "medium" refers to a composition (usually aqueous) comprising the starting composition and any other substances required for transformation of the starting or first steviol glycoside to the target glycoside. For example, a medium can comprise water, a starting composition, buffer and/or salts.

In one embodiment, the medium comprises one or more co-substrates for the biocatalyst, e.g. sucrose in the case of dextransucrase or UDP-glucose in the case of UGTs.

As used herein, "biocatalysis" or "biocatalytic" refers to the use of natural or genetically engineered biocatalysts, such as enzymes, or cells comprising one or more enzyme, capable of single or multiple step chemical transformations of organic compounds. Biocatalysis processes include fermentation, biosynthesis and biotransformation processes. Both isolated enzyme and whole-cell biocatalysis methods are known in the art. Biocatalyst protein enzymes can be naturally occurring or recombinant proteins.

The starting steviol glycoside is the steviol glycoside to which the biocatalyst adds a glucose unit, thereby producing the target steviol glycoside.

In some embodiments of the present method, the target steviol glycoside is subjected to a further biocatalysis step, i.e. the target steviol glycoside is actually an intermediate. In such embodiments, the starting steviol glycoside is referred to as the "first steviol glycoside" and the target steviol glycoside is referred to as the "second steviol glycoside".

In such embodiments, the method comprises (a) contacting a first medium containing a first composition comprising a first steviol glycoside with a biocatalyst to product a second composition comprising a second steviol glycoside; (b) contacting a second medium comprising the second composition comprising a second steviol glycoside with a biocatalyst to produce a composition comprising a third steviol glycoside. The third steviol glycoside can be treated similarly to provide a fourth steviol glycoside, etc.

The starting composition comprises the starting steviol glycoside. In some embodiments, the starting composition is a steviol glycoside mixture or Stevia extract (commercial or prepared), optionally enriched in the starting steviol glycoside. In other embodiments, the starting composition comprises the starting steviol glycoside in at least about 50% by weight on a dry basis, at least about 60% by weight on a dry basis, at least about 70% by weight on a dry basis, at least about 80% by weight on a dry basis or at least about 90% by weight on a dry basis. In still other embodiments, the starting composition is substantially pure starting steviol glycoside, i.e. a composition comprising the starting steviol glycoside in at least about 95% purity by weight on a dry basis.

In yet other embodiments, the starting composition is the composition obtained from reaction of a previous biocatalytic step, e.g. the second composition comprising a second steviol glycoside in step (b), above, is the second composition comprising the second steviol glycoside of step (a), above. The starting composition obtained from previous biocatalytic steps (e.g. the second composition) can be at least partially separated from the reaction medium and biocatalytic products.

In one embodiment, the starting steviol glycoside is rebaudioside A and the target steviol glycoside is CC-00326:

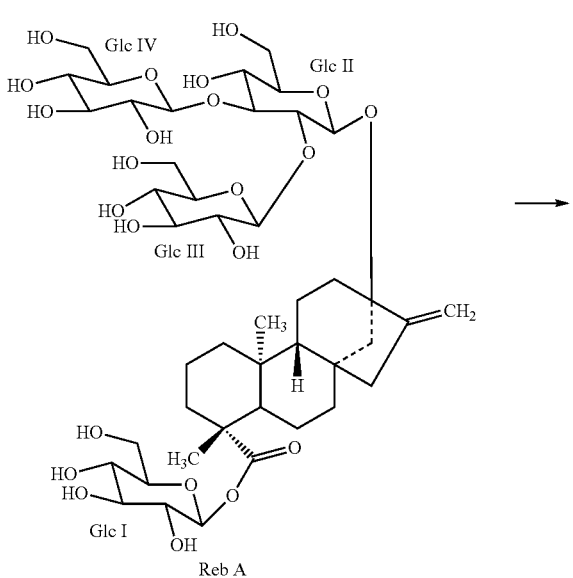

Reb A

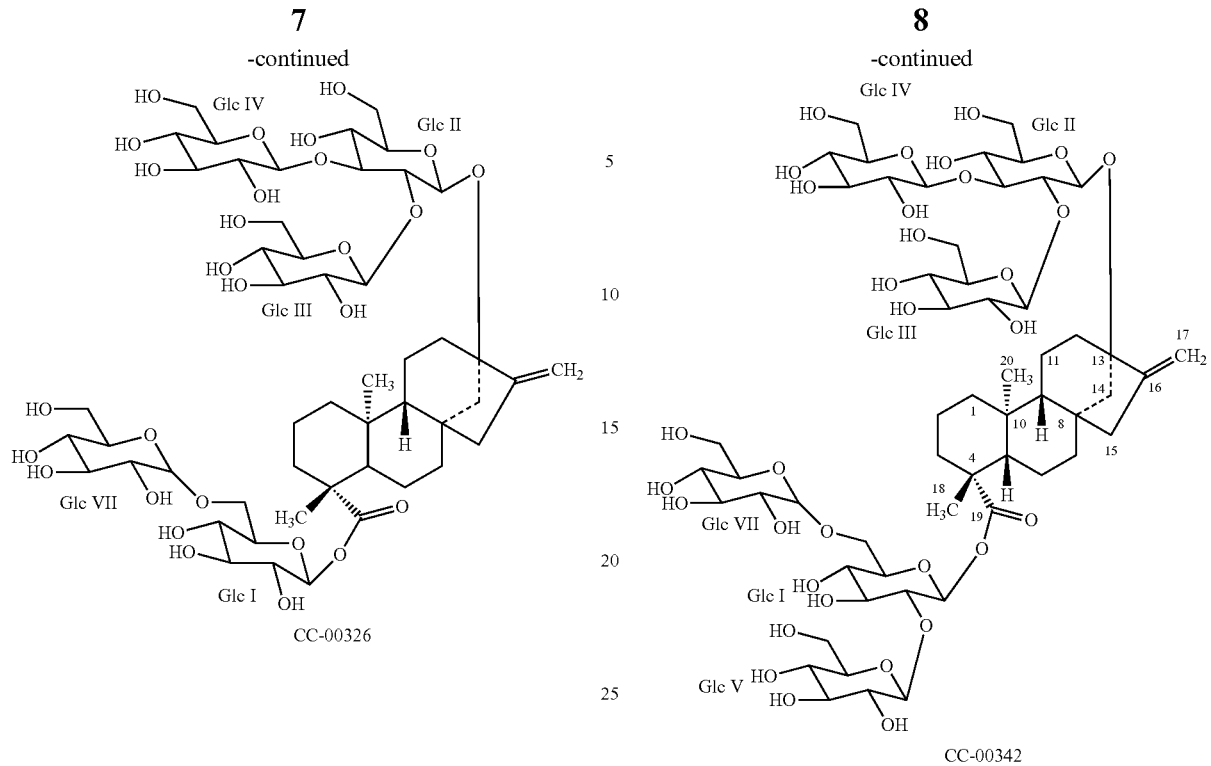

As such, a method for preparing CC-00326 comprises contacting a medium comprising a composition comprising rebaudioside A with a biocatalyst to produce a composition comprising CC-00326.

In another embodiment, the starting steviol glycoside is CC-00326 and the target steviol glycoside is CC-00342:

As such, a method for preparing CC-00342 comprises contacting a medium comprising a composition comprising CC-00326 with a biocatalyst to produce a composition comprising CC-00342.

In yet another embodiment, the starting steviol glycoside is CC-00342 and the target steviol glycoside is CC-00345:

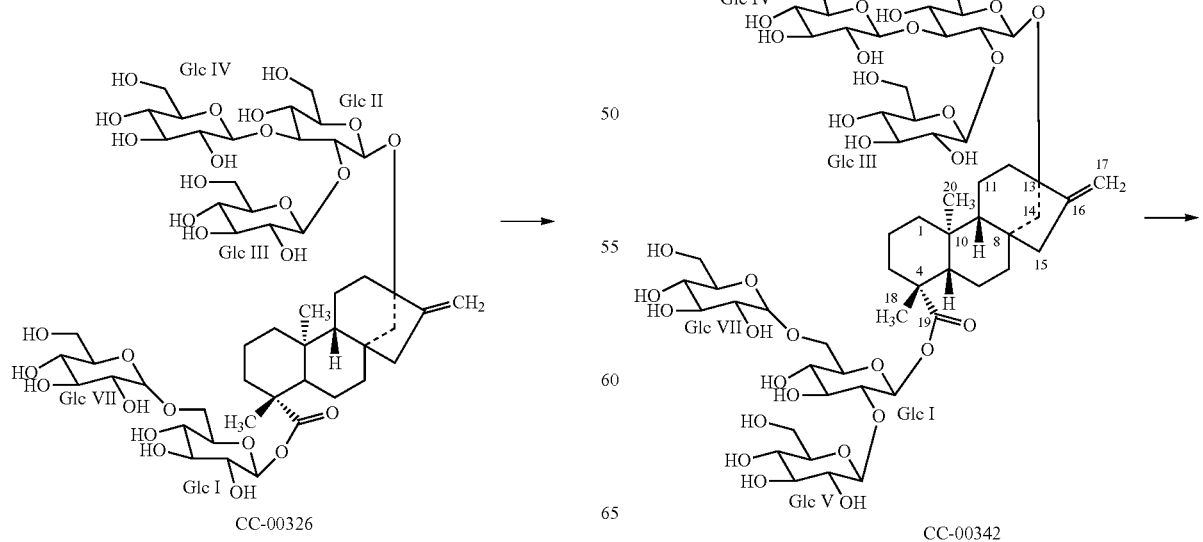

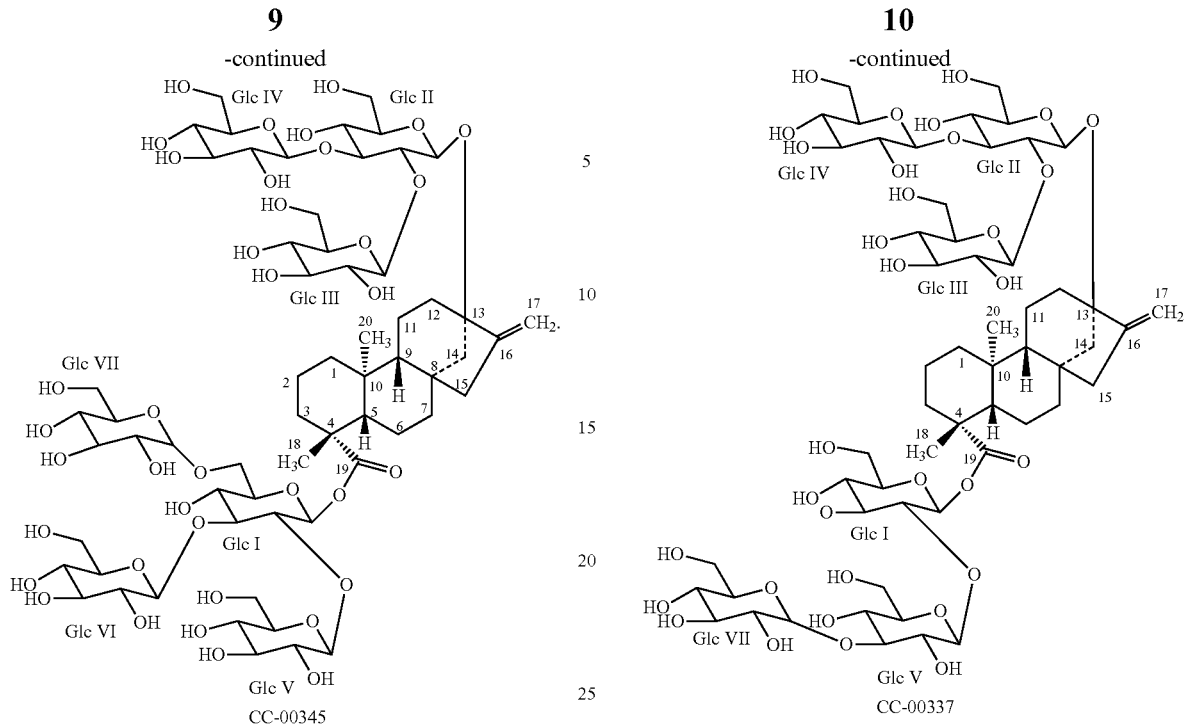

CC-00345

As such, a method for preparing CC-00345 comprises contacting a medium comprising a composition comprising CC-00342 with a biocatalyst to produce a composition comprising CC-00345.

In still another embodiment, the starting steviol glycoside is rebaudioside D and the target steviol glycoside is CC-00337.

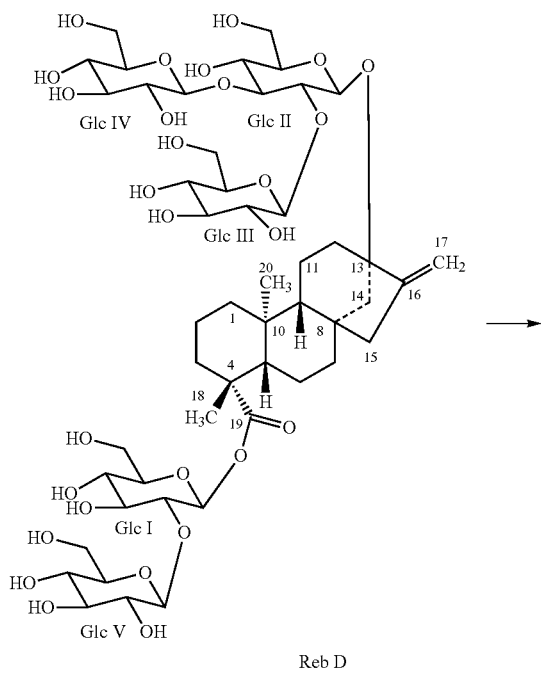

Reb D

CC-00337

As such, a method for preparing CC-00337 comprises contacting a medium comprising a composition comprising rebaudioside D with a biocatalyst to produce a composition comprising CC-00337.

In yet another embodiment, a method for preparing CC-00345 comprises (a) contacting a first medium containing a first composition comprising rebaudioside A with a biocatalyst to produce a second composition comprising CC-00326; (b) contacting a second medium comprising the second composition comprising CC-00326 with a biocatalyst to produce a third composition comprising CC-00342. The method may further comprise (c) contacting a third medium comprising the third composition comprising CC-00342 with a biocatalyst to produce a composition comprising CC-00345.

The concentration of the steviol glycoside in the medium is typically from about 1.0 mM to about 50 mM, such as, for example, from about 1.0 mM to about 20 mM, or from about 1.0 mM to about 15 mM.

In one embodiment, the starting composition is contacted with the biocatalyst in a medium comprising water, and, e.g. various components selected from carbon sources, energy sources, nitrogen sources, microelements, vitamins, nucleosides, nucleoside phosphates, nucleoside diphosphates, nucleoside triphosphates, organic and inorganic salts, organic and mineral acids, bases and combinations thereof. Exemplary carbon sources include glycerol, glucose, carbon dioxide, carbonates, bicarbonates. Exemokart nitrogen sources include nitrates, nitrites, amino acids, peptides, peptones, or proteins.

In a particular embodiment, the medium comprises buffer. Suitable buffers include, but are not limited to, PIPES buffer, acetate buffer, phosphate buffer and combinations thereof. In a particular embodiment, the medium comprises phosphate buffer.

In one embodiment, the medium can also include an organic solvent, e.g. methanol, ethanol, propanol and the like.

As used herein, "biocatalyst" refers to an enzyme capable of converting a starting steviol glycoside to a target steviol glycoside. The enzyme can be naturally occurring or a recombinant enzyme (e.g., recombinant protein). At least one biocatalyst is used for the present method. However, multiple biocatalysts can be used, as necessary. Accordingly, in some embodiments, two or more biocatalysts are utilized, such as, for example, three or more biocatalysts, four or more biocatalysts or five or more biocatalysts.

The biocatalyst can be provided in the form of a whole cell suspension, a crude lysate, purified form or a combination thereof. In one embodiment, the biocatalyst is provided in purified form, i.e., as a purified enzyme. In another embodiment, the biocatalyst is provided in the form of a crude lysate. In still another embodiment, the biocatalyst is provided in the form of a whole cell suspension.

In another embodiment, the biocatalyst is provided in the form of one or more cells, i.e., the biocatalyst is associated with a cell(s). The biocatalyst can be located on the surface of the cell, inside the cell, or both on the surface of the cell and inside the cell.

In another embodiment, the biocatalyst is provided in the form of a microorganism, i.e., the biocatalyst is associated with a microorganism. The microorganism can be any microorganism possessing the necessary biocatalyst(s)/enzyme(s). Suitable microorganisms include, but are not limited to, *E. coli, Saccharomyces* sp., *Aspergillus* sp., *Pichia* sp., *Bacillus* sp., *Yarrowia* sp. etc.

In one embodiment, the microorganism is free (i.e., not immobilized) when contacted with the starting composition.

In another embodiment, the microorganism is immobilized when contacted with the starting composition. For example, the microorganism may be immobilized to a solid support made from inorganic or organic materials. Non-limiting examples of solid supports suitable to immobilize the microorganism include derivatized cellulose or glass, ceramics, metal oxides or membranes. The microorganism may be immobilized to the solid support, for example, by covalent attachment, adsorption, cross-linking, entrapment or encapsulation.

In still another embodiment, the biocatalyst is secreted by the microorganism into the reaction medium.

Suitable biocatalysts for the present method are capable of forming glycosidic bonds including, but are not limited to, glycosyltransferases.

Glycosyltransferases are enzymes that catalyze the transfer of sugar moieties from activated donor molecules to specific acceptor molecules, forming glycosidic bonds. The glycosyltransferases used herein add glucose moieties to the glycoside at C-19 of the aglycone.

Any glycosyltransferase that is capable of adding a glucose at the correct position and providing the proper stereochemistry can be utilized. Suitable glycosyltransferases include, but are not limited to, dextransucrase and UDP glucosyltransferases.

Dextransucrase from *Leuconostoc Lactis* (DS-LeuLac) selectively glucosylates rebaudioside A at the C-19 β-linked glucose residue with a α1→6 linked glucose to provide CC-00326. In one embodiment, the DS-LeuLac is provided as a cell lysate.

The concentration of DS-LeuLac can vary based on activity of the enzyme, i.e. the amount of reducing sugars (3,5-dinitrosalicylic acid assay) produced from sucrose (100 g/L) in 20 mM sodium acetate buffer pH 5.5 in the presence of 0.02 g/L $CaCl_2$ at 30° C.

Dextransucrase requires sucrose as a glucose donor. The concentration of the sucrose in the medium is typically equimolar to the steviol glycoside. In one embodiment, the concentration of sucrose in the medium is from about 1.0 mM to about 50 mM, such as, for example, from about 100 mM to about 500 mM, or from about 200 mM to about 300 mM.

UDP glucosyltransferases (UGTs) are efficient enzymes with high region-specificity, catalyzing the transfer of α- or β-linked glucoses at a specific location. UGTs catalyzes the addition of the glycosyl group from a UTP-sugar to a molecule.

In one embodiment, the UDP glucosyltransferase is EUGT11. EUGT11 selectively glucosylates C-00326 at the C-19 β-linked glucose residue with a β1→2 linked glucose to provide CC-00342. In one embodiment, the EUGT11 is provided as a cell lysate. In a more particular embodiment, the EUGT11 is provided in an *E. coli* cell lysate.

The concentration of EUGT11 will vary based on activity of the enzyme, i.e. the amount of enzyme required for conversion of rebaudioside A to rebaudioside D under assay conditions.

EUGT11 requires UDP-glucose as the glucose donor/substrate. The concentration of the UDP-glucose in the medium is typically equimolar to the starting steviol glycoside. In one embodiment, the concentration of UDP-glucose in the medium is from about 1.0 mM to about 50 mM, such as, for example, from about 100 mM to about 500 mM, or from about 200 mM to about 300 mM.

In certain embodiments, the methods of the present invention further comprise recycling UDP to provide UDP-glucose. UDP is concomitantly recycled by providing a recycling catalyst, i.e., a biocatalyst capable of UDP-glucose overproduction, and a recycling substrate, such that the conversion of the starting steviol glycoside to the target steviol glycoside is carried out using catalytic amounts of UDP-glucosyltransferase and UDP-glucose. For example, the UDP-glucose recycling catalyst can sucrose synthase and the recycling substrate can be sucrose.

When catalytically performed, the concentration of UDP in the medium is typically 0.25 equivalents of the starting steviol glycoside. In one embodiment, the concentration of UDP is from about 0.10 mM to about 0.5 mM, such as 0.25 mM. The concentration of sucrose is typically from about 50 mM to about 200 mM, such as, for example, from about 100 mM to about 150 mM. The concentration of sucrose synthase will vary based on the activity of the enzyme, i.e. the amount of enzyme required for formation of reducing sugars from the reaction of sucrose with UDP using di-nitro salicylic acid (DNS) assay.

In one embodiment, the UDP glucosyltransferase is UGT76G1. UGT76G1 selectively glucosylates C-00342 at the C-19 β-linked glucose residue with a β1→3 linked glucose to provide CC-00345. In one embodiment, the UGT76G1 is provided as a cell lysate. In a more particular embodiment, the EUGT11 is provided in an *E. coli* cell lysate.

Like EUGT11, UGT76G1 also requires UDP-glucose as the glucose donor. The concentration of the UDP-glucose in the medium is typically equimolar to the starting steviol glycoside. In one embodiment, the concentration of UDP-glucose in the medium is from about 1.0 mM to about 50 mM, such as, for example, from about 100 mM to about 500 mM, or from about 200 mM to about 300 mM.

The concentration of UGT76G1 will vary based on activity of the enzyme, i.e. the amount of enzyme required for conversion of rebaudioside D to rebaudioside M under assay conditions.

In certain embodiments, the methods of the present invention further comprise recycling UDP to provide UDP-glucose. UDP is concomitantly recycled by providing a recycling catalyst, i.e., a biocatalyst capable of UDP-glucose overproduction, and a recycling substrate, such that the conversion of the starting steviol glycoside to the target steviol glycoside is carried out using catalytic amounts of UDP-glucosyltransferase and UDP-glucose. For example, the UDP-glucose recycling catalyst can sucrose synthase and the recycling substrate can be sucrose.

When catalytically performed, the concentration of UDP in the medium is typically 0.25 equivalents of the starting steviol glycoside. In one embodiment, the concentration of UDP is from about 0.10 mM to about 0.5 mM, such as 0.25 mM. The concentration of sucrose is typically from about 50 mM to about 200 mM, such as, for example, from about 100 mM to about 150 mM. The concentration of sucrose synthase will vary based on the activity of the enzyme, i.e. the amount of enzyme required for formation of reducing sugars from the reaction of sucrose with UDP using di-nitro salicylic acid (DNS) assay.

Dextransucrase ATCC11449 (DS-ATCC11449) selectively glucosylates rebaudioside D at the C-19 β-linked glucose residue with a α1→3 linked glucose to provide CC-00337. In one embodiment, the dextransucrase ATCC11449 is provided as a cell lysate. In a more particular embodiment, the dextransucrase is from *Leuconostoc mesenteroides mesenteroides*.

The concentration of DS-ATCC11449 will vary based on activity of the enzyme, i.e. the amount of reducing sugars (3,5-dinitrosalicylic acid assay) that was produced from sucrose (100 g/L) in 20 mM sodium actetate buffer pH 5.5 in the presence of 0.02 g/L $CaCl_2$ at 30° C.

DS-ATCC11449 requires sucrose as a glucose donor/substrate. The concentration of the sucrose in the medium is typically equimolar to the steviol glycoside. In one embodiment, the concentration of sucrose in the medium is from about 1.0 mM to about 50 mM, such as, for example, from about 100 mM to about 500 mM, or from about 200 mM to about 300 mM.

The reactions of the present invention are typically performed at temperatures from about 20° C. to about 70° C., such as, for example from about 23° C. to about 40° C., or about 30° C.

The reactions of the present invention are typically performed in the pH range of about 3 to about 9, such as, for example, from about 5 to about 8.

In a particular embodiment, the methods of the present invention provide a composition comprising the target steviol glycoside in an amount of about 1% or greater by weight, such as, for example, about 5% or greater, about 10% or greater, about 20% or greater, about 30% or greater, about 40% or greater, about 50% or greater, about 60% or greater, about 70% or greater, about 80% or greater or about 90% or greater by weight.

The composition comprising the target steviol glycoside typical includes reaction by-products, excess reagents, unreacted starting material and other undesirable materials. Accordingly, in some embodiments, the methods disclosed herein further comprise separating the target steviol glycoside from at least some of these undesirable materials in the composition to provide a separated target steviol glycoside composition. Any suitable method separation method can be used, such as, for example, lysis, crystallization, separation by membranes, centrifugation, extraction (liquid or solid phase), chromatographic separation, HPLC (preparative or analytical) or a combination of such methods. In a particular embodiment, separation can be achieved by lysis and centrifugation.

In one embodiment, the target steviol glycoside is continuously removed from the medium while the conversion progresses. In another embodiment, the target steviol glycoside is separated from the medium after the reaction is quenched (not necessarily complete).

Separation results in compositions having a lower target steviol glycoside content than desired and/or the composition may contain additional components, e.g., non-desirable steviol glycosides (in identity or content) and/or residual reaction products. In one embodiment, the separated target steviol glycoside composition comprises the target steviol glycoside in a purity of at least about 50% by weight or greater on a dry basis, such as, for example, about 60% or greater, about 65% or greater, about 70% or greater, about 75% or greater, about 80% or greater, about 85% or greater, about 90% or greater.

The separated target steviol glycoside composition can be further purified to provide a purified target steviol glycoside composition. The purity of the target steviol glycoside in the purified target steviol glycoside composition is greater than the purity of the target steviol glycoside in the separated target steviol glycoside composition. The term "purified", as used herein, refers to a composition having greater than about 80% by weight target steviol glycoside on a dry basis. In one embodiment, the purified composition contains greater than about 90% of the target steviol glycoside by weight, such as, for example, greater than about 91%, greater than about 92%, greater than about 93%, greater than about 94%, greater than about 95%, greater than about 96%, greater than about 97%, greater than about 98% or about 99% by weight.

In exemplary embodiments, purification provides a pure target steviol glycoside, i.e., >99% by weight target steviol glycoside on a dry basis.

Purification can be affected by any means known to one of skill in the art including, but not limited to, crystallization, separation by membranes, centrifugation, extraction (liquid or solid phase), chromatographic separation, HPLC (preparative or analytical) or a combination of such methods. In a particular embodiment, HPLC is used. In a more particular embodiment, preparative HPLC is used. Preparative HPLC can be iteratively performed until the desired purity is achieved.

The present invention also extends to methods of purifying a steviol glycoside of the present invention.

In one embodiment, the present invention is a method for purifying a steviol glycoside of the present invention comprising (i) passing a solution comprising a source material comprising a steviol glycoside of the present invention through a HPLC column and (ii) eluting fractions comprising a steviol glycoside of the present invention to provide purified steviol glycoside of the present invention. The HPLC column can be any suitable HPLC preparative or semi-preparative scale column.

As used herein, the term "preparative HPLC" refers to an HPLC system capable of producing high (500 or more) microgram, milligram, or gram sized product fractions. The term "preparative" includes both preparative and semi-preparative columns, but is not intended to include analytical columns, which provide fractions in the nanogram to low microgram range.

As used herein, an "HPLC compatible detector" is a detector suitable for use in an HPLC system which is capable of providing a detectable signal upon elution of a compound peak. For example, a detector capable of generating a signal when a compound elutes from the compound is an HPLC compatible detector. Where component absorbance varies widely, it may be necessary to utilize more than one detector. A detector capable of detecting a desired component is not an "incompatible" detector due to its inability to detect a non-desired peak.

An HPLC device typically includes at least the following components: a column, packed with a suitable stationary phase, a mobile phase, a pump for forcing the mobile phase through the column under pressure and a detector for detecting the presence of compounds eluting off of the column. The devices can optionally include a means for providing for gradient elution, although that is not necessary using the methods described herein. Routine methods and apparatus for carrying out HPLC separations are well known in the art.

Suitable stationary phases are those in which the compound of interest elutes. Preferred columns include, and are not limited to, normal phase columns (neutral, acidic or basic), reverse phase columns (of any length alkyl chain), a synthetic crosslinked polymer columns (e.g., styrene and divinylbenzene), size exclusion columns, ion exchange columns, bioaffinity columns and any combination thereof. The particle size of the stationary phase is within the range from a few μm to several 100 μm.

Suitable detection devices include, but are not limited to, mass spectrometers, UV detectors, IR detectors and light scattering detectors. The methods described herein use any combination of these detectors. The most preferable embodiment uses mass spectrometers and UV detectors.

"Source material", as used herein, refers to the material being purified by the present method. The source material contains a steviol glycoside of the present invention in a purity less than the purity provided by the present purification method. The source material can be liquid or solid. Exemplary source materials include, but are not limited to, mixtures of steviol glycosides, Stevia extract, Stevia plant leaves, by-products of other steviol glycosides' isolation and purification processes, commercially available steviol extracts or Stevia extracts, by-products of biotransformation reactions of other steviol glycosides or any combination thereof.

As understood by persons skilled in the art, any solid source materials must be brought into solution prior to carrying out the HPLC method.

In one embodiment, a representative analytical HPLC protocol is correlated to a preparative or semi-preparative HPLC protocol used to purify a compound.

In another embodiment, appropriate conditions for purifying a steviol glycoside of the present invention can be worked out by route scouting a representative sample for a given analytical HPLC column, solvent system and flow rate. In yet another embodiment, a correlated preparative or semipreparative HPLC method can be applied to purify a steviol glycoside of the present invention with modifications to the purification parameters or without having to change the purification parameters.

In some embodiments, the eluent (mobile phase) is selected from the group consisting of water, acetonitrile, methanol, 2-propanol, ethyl acetate, dimethylformamide, dimethylsulfide, pyridine, triethylamine, formic acid, trifluoroacetic acid, acetic acid, an aqueous solution containing ammonium acetate, heptafluorobutyric acid and any combination thereof.

In one embodiment, the HPLC method is isocratic. In another embodiment, the HPLC method is a gradient. In still another embodiment, the HPLC method is step-wise.

In one embodiment, impurities are eluted off of the HPLC column after eluting one or more fractions containing a steviol glycoside of the present invention. In another embodiment, impurities are eluted off of the HPLC column before eluting one or more fractions containing a steviol glycoside of the present invention.

The method can further include removal of solvent from the eluted solution, i.e. drying. In one embodiment, the method further comprises partial removal of solvents from the eluted solution to provide a concentrate comprising a steviol glycoside of the present invention. In another embodiment, the method further comprises removing substantially all the solvent from the eluted solutions to provide substantially dry material comprising a steviol glycoside of the present invention.

Removal of solvent can be performed by any means known to one of skill in the art including, but not limited to, evaporation, distillation, vacuum drying and spray drying.

The resulting purified fractions comprising a steviol glycoside of the present invention can be further purified by other methods to increase purity. Suitable methods include, but are not limited to, crystallization, chromatography, extraction and distillation. Such methods are well-known to persons skilled in the art.

The source material can be one fraction, or multiple fractions, containing a steviol glycoside of the present invention collected from at least one previous method or HPLC protocol. In one embodiment, multiple fractions from the same, previous methods or HPLC protocols are pooled and optionally, solvents are removed, prior to re-subjecting the source material to another method. In other embodiments, fractions from different, previous methods or HPLC protocol are pooled, and optionally, solvents are removed, prior to re-subjecting the source material to another method.

In one embodiment, the source material re-subjected to additional method(s) comprises liquid fractions obtained from one or more previous (and optionally, different) methods mixed with substantially dry material obtained via drying of fractions obtained from one or more previous (and optionally, different) methods. In another embodiment, the source material re-subjected to additional method(s) comprises substantially dry material obtained via drying of fractions obtained from one or more previous (and optionally, different) methods, where said source material is brought into solution prior to passing the solution through the next HPLC column.

The second and subsequent methods may have different HPLC protocols (e.g. solvent systems, columns, methods) and different steps following elution (e.g. partial removal of solvent, complete removal of solvent, elution of impurities, use of crystallization or extraction).

The material isolated can be subjected to further methods 2, 3, 4 or more times, each time providing a higher level of purity of purified steviol glycoside of the present invention.

In one embodiment, the method provides a purified target steviol glycoside of the present invention. In another embodiment, the method provides a pure target steviol glycoside of the present invention.

Between each conversion the target steviol glycoside may be separated and/or purified from the reaction medium prior to contacting with the next biocatalyst.

I. Compounds

In one aspect, the present invention provides one of the following target steviol glycosides:

CC-00326

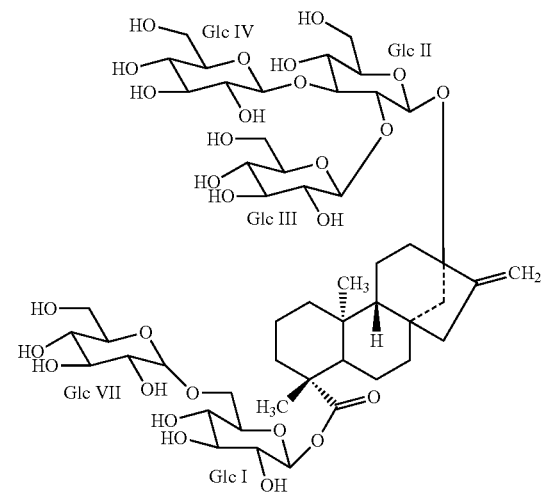

CC-00342

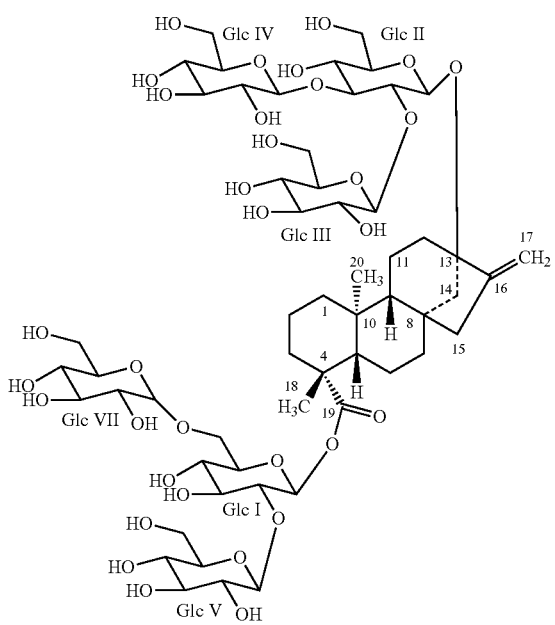

CC-00345

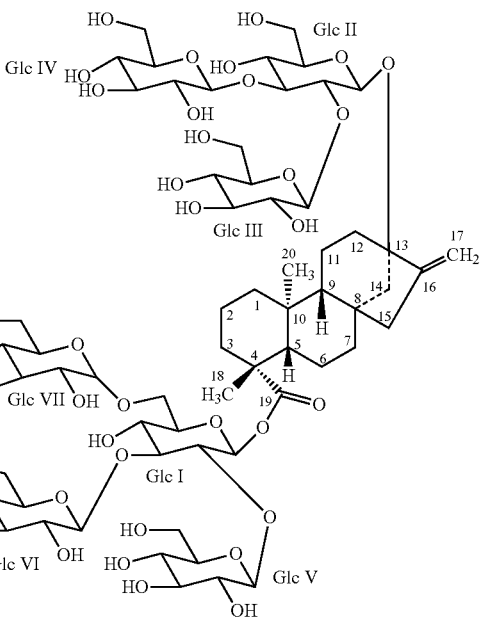

CC-00337

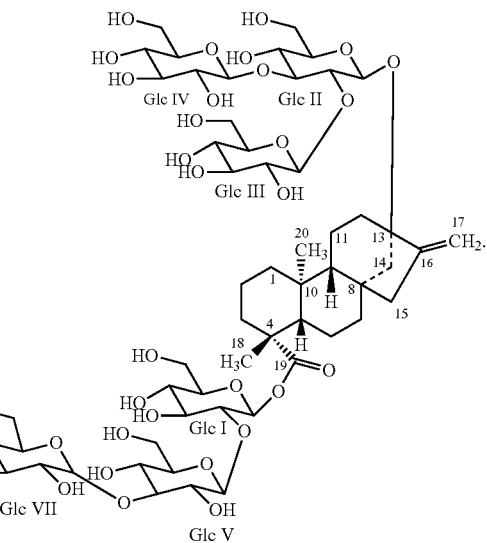

In exemplary embodiments, the target steviol glycoside of the present invention is isolated and purified. The term "isolated and purified", as used herein, means that the target steviol glycoside is about 95% by weight or greater on a dry basis, i.e. is greater than about 95% pure. The remainder of the mixture is typically other steviol glycoside. In more specific embodiments, the target steviol glycoside has a purity of about 96% or greater, about 97% or greater, about 98% or greater or about 99% or greater.

The target steviol glycosides of the present invention are sweet. The sweetness of a given composition is typically measured with reference to a solution of sucrose. See generally "A Systematic Study of Concentration-Response Relationships of Sweeteners," G. E. DuBois, D. E. Walters, S. S. Schiffman, Z. S. Warwick, B. J. Booth, S. D. Pecore, K. Gibes, B. T. Carr, and L. M. Brands, in *Sweeteners: Discovery, Molecular Design and Chemoreception*, D. E.

Walters, F. T. Orthoefer, and G. E. DuBois, Eds., American Chemical Society, Washington, D.C. (1991), pp 261-276.

The sweetness of a non-sucrose sweetener can be measured against a sucrose reference by determining the non-sucrose sweetener's sucrose equivalence (SE). Typically, taste panelists are trained to detect sweetness of reference sucrose solutions containing between 1-15% sucrose (w/v). Other non-sucrose sweeteners are then tasted at a series of dilutions to determine the concentration of the non-sucrose sweetener that is as sweet as a given percent sucrose reference. For example, if a 1% solution of a sweetener is as sweet as a 10% sucrose solution, then the sweetener is said to be 10 times as potent as sucrose, and has 10% sucrose equivalence.

In one embodiment, the target steviol glycoside is present in an amount that, when added to a consumable, provides a sucrose equivalence of greater than about 2% (w/v), such as, for example, greater than about 3%, about 4%, about 5%, about 6%, about 7%, about 8%, about 9%, about 10%, about 11%, about 12%, about 13% or about 14%.

The amount of sucrose, and thus another measure of sweetness, in a reference solution may be described in degrees Brix (° Bx). One degree Brix is 1 gram of sucrose in 100 grams of solution and represents the strength of the solution as percentage by weight (% w/w) (strictly speaking, by mass). In one embodiment, the target steviol glycoside of the present invention is present in an amount that, when added to a consumable, provides a sweetness equivalent from about 0.50 to 14 degrees Brix, such as, for example, from about 5 to about 12 degrees Brix, about 7 to 10 degrees Brix, or above 10 degrees Brix.

II. Compositions

The present invention includes compositions comprising at least one target steviol glycoside of the present invention. "Composition," as the term is used herein, refers to a mixture of at least one target steviol glycoside of the present invention and at least one other substance.

In a particular embodiment, the at least one other substance does not occur and/or is not admixed with the target steviol glycoside in nature, i.e. the *Stevia* leaf. As such, the compositions contemplated by the present invention do not occur in nature.

In one embodiment, the present invention is a composition comprising at least one target steviol glycoside of the present invention, provided as part of a mixture. In a particular embodiment, the mixture is selected from the group consisting of diterpene glycosides, *Stevia* extract, by-products of other diterpene glycosides' isolation and purification processes (e.g. the methods above), commercially available diterpene extracts or *Stevia* extracts, by-products of biotransformation reactions of other diterpene glycosides, or any combination thereof.

In one embodiment, the mixture contains at least one target steviol glycoside of the present invention in an amount that ranges from about 1% to about 99% by weight on a dry basis, such as, for example, about 5% to about 99% by weight on a dry basis, from about 10% to about 99%, from about 20% to about 99%, from about 30% to about 99%, from about 40% to about 99%, from about 50% to about 99%, from about 60% to about 99%, from about 70% to about 99%, from about 80% to about 99% and from about 90% to about 99%. In a particular embodiment, the mixture contains at least one target steviol glycoside of the present invention in an amount greater than about 90% by weight on a dry basis, for example, greater than about 91%, greater than about 92%, greater than about 93%, greater than about 94% or greater than about 95%.

In certain exemplary embodiments, the composition comprises one purified target steviol glycoside of this invention. In other embodiments, the composition comprises more than one steviol glycoside of the present invention.

In one embodiment, a purified target steviol glycoside of the present invention is the sole sweetener in the composition, i.e. the target steviol glycoside is the only compound present in the composition that provides a detectable sweetness.

In further embodiments, the composition comprises at least one target steviol glycoside of the present invention in combination with at least one additional sweetener. In a more particular embodiment, a composition comprises at least one purified target steviol glycoside and at least one additional sweetener.

The amount of target steviol glycoside of the present invention in the composition may vary. In one embodiment, the target steviol glycoside is present in a composition in any amount to impart the desired sweetness when the composition is added to a sweetenable composition or sweetenable consumable. In a particular embodiment, the target steviol glycoside is present in a concentration above its threshold sweetness recognition concentration.

In one embodiment, the target steviol glycoside is present in the composition in an amount effective to provide a sucrose equivalence of greater than about 2% (w/v) when the composition is added to a sweetenable composition or sweetenable consumable, such as, for example, greater than about 3%, about 4%, about 5%, about 6%, about 7%, about 8%, about 9%, about 10%, about 11%, about 12%, about 13% or about 14%.

In other embodiments, a target steviol glycoside is present in the composition in an amount that, when added to a consumable, will provide a concentration of the steviol glycoside greater than about 10 ppm, such as, for example, greater than about 20 ppm, about 30 ppm, about 40 ppm, about 50 ppm, about 60 ppm, about 70 ppm, about 80 ppm, about 90 ppm, about 100 ppm, about 200 ppm, about 300 ppm, about 400 ppm, about 500 ppm, about 600 ppm, about 700 ppm, about 800 ppm or about 900 ppm.

In still other embodiments, a target steviol glycoside is present in the composition in an amount that, when added to a consumable, will provide a concentration of the target steviol glycoside from about 1 ppm to about 1,000 ppm, such as, for example, from about 50 ppm to about 1,000 ppm, from about 100 ppm to about 1,000 ppm, from about 200 ppm to about 1,000 ppm, from about 300 ppm to about 1,000 ppm, from about 400 ppm to about 1,000 ppm, from about 500 ppm to about 1,000 ppm, from about 600 ppm to about 1,000 ppm, from about 700 ppm to about 1,000 ppm, from about 800 ppm to about 1,000 ppm or from about 900 ppm to about 1,000 ppm.

In a more particular embodiment, a target steviol glycoside is present in the composition in an amount that, when added to a consumable, will provide a concentration of the target steviol glycoside from about 50 ppm to about 600 ppm, such as, for example, from about 100 ppm to about 600 ppm, from about 200 ppm to about 600 ppm, from about 300 ppm to about 600 ppm, from about 400 to about 600 ppm and from about 500 to about 600 ppm.

In one embodiment, the additional sweetener is at least one natural high-potency sweetener. As used herein, the phrase "natural high potency sweetener" refers to any sweetener found naturally in nature and characteristically has a sweetness potency greater than sucrose, fructose, or glucose, yet has less calories. The natural high potency sweetener can be provided as a pure compound or, alternatively, as part of an extract.

In another embodiment, the additional sweetener is at least one synthetic sweetener. As used herein, the phrase "synthetic sweetener" refers to any composition which is not found naturally in nature and characteristically has a sweetness potency greater than sucrose, fructose, or glucose, yet has less calories.

In still other embodiments, combinations of natural high potency sweeteners and synthetic sweeteners are contemplated.

In other embodiments, the additional sweetener is at least one carbohydrate sweetener. Suitable carbohydrate sweeteners are selected from, but not limited to, the group consisting of sucrose, glyceraldehyde, dihydroxyacetone, erythrose, threose, erythrulose, arabinose, lyxose, ribose, xylose, ribulose, xylulose, allose, altrose, galactose, glucose, gulose, idose, mannose, talose, fructose, psicose, sorbose, tagatose, mannoheptulose, sedoheltulose, octolose, fucose, rhamnose, arabinose, turanose, sialose and combinations thereof.

Other suitable additional sweeteners include rebaudioside A, rebaudioside B, rebaudioside C, rebaudioside D, rebaudioside E, rebaudioside F, rebaudioside I, rebaudioside H, rebaudioside L, rebaudioside K, rebaudioside J, rebaudioside M, rebaudioside N, rebaudioside O, dulcoside A, dulcoside B, rubusoside, Stevia, stevioside, mogroside IV, mogroside V, mogroside VI, Luo han guo, siamenoside I, isomgorside V, Mogroside IIIe, monatin and its salts (monatin SS, RR, RS, SR), curculin, glycyrrhizic acid and its salts, thaumatin, monellin, mabinlin, brazzein, hernandulcin, phyllodulcin, glycyphyllin, phloridzin, trilobatin, baiyunoside, osladin, polypodoside A, pterocaryoside A, pterocaryoside B, mukurozioside, phlomisoside I, periandrin I, abrusoside A, steviolbioside, hesperitin and cyclocarioside I, sugar alcohols such as erythritol, sucralose, potassium acesulfame, acesulfame acid and salts thereof, aspartame, alitame, saccharin and salts thereof, neohesperidin dihydrochalcone, cyclamate, cyclamic acid and salts thereof, neotame, advantame, glucosylated steviol glycosides (GSGs) and combinations thereof.

In a particular embodiment, the additional sweetener is at least one calorie-providing carbohydrate sweetener. In one embodiment, the additional sweetener is a caloric sweetener or mixture of caloric sweeteners. In another embodiment, the caloric sweetener is selected from sucrose, fructose, glucose, high fructose corn/starch syrup, a beet sugar, a cane sugar and combinations thereof.

In another embodiment, the additional sweetener is a rare sugar selected from allulose, sorbose, lyxose, ribulose, xylose, xylulose, D-allose, L-ribose, D-tagatose, L-glucose, L-fucose, L-arabinose, turanose, kojibiose and combinations thereof.

In still another embodiment, the additional sweetener is a mixture of at least one natural high potency sweetener and at least one carbohydrate sweetener. In yet another embodiment, the additional sweetener is a mixture of at least one synthetic sweetener and at least one carbohydrate sweetener. In a further embodiment, the additional sweetener is at least one natural high potency sweetener, at least one synthetic sweetener and at least one carbohydrate sweetener.

Additives

The compositions may comprise, in addition to at least one target steviol glycoside, one or more additives and/or functional ingredients, detailed below.

Exemplary additives include, but not limited to, carbohydrates, polyols, amino acids and their corresponding salts, poly-amino acids and their corresponding salts, sugar acids and their corresponding salts, nucleotides, organic acids, inorganic acids, organic salts including organic acid salts and organic base salts, inorganic salts, bitter compounds, caffeine, flavorants and flavoring ingredients, astringent compounds, proteins or protein hydrolysates, surfactants, emulsifiers, plant extracts, flavonoids, alcohols, polymers and combinations thereof.

In one embodiment, the composition further comprises one or more polyols. The term "polyol", as used herein, refers to a molecule that contains more than one hydroxyl group. A polyol may be a diol, triol, or a tetraol which contains 2, 3, and 4 hydroxyl groups respectively. A polyol also may contain more than 4 hydroxyl groups, such as a pentaol, hexaol, heptaol, or the like, which contain 5, 6, or 7 hydroxyl groups, respectively. Additionally, a polyol also may be a sugar alcohol, polyhydric alcohol, or polyalcohol which is a reduced form of carbohydrate, wherein the carbonyl group (aldehyde or ketone, reducing sugar) has been reduced to a primary or secondary hydroxyl group.

Non-limiting examples of polyols in some embodiments include maltitol, mannitol, sorbitol, lactitol, xylitol, isomalt, propylene glycol, glycerol (glycerin), threitol, galactitol, palatinose, reduced isomalto-oligosaccharides, reduced xylo-oligosaccharides, reduced gentio-oligosaccharides, reduced maltose syrup, reduced glucose syrup, and sugar alcohols or any other carbohydrates capable of being reduced which do not adversely affect taste.

Suitable amino acid additives include, but are not limited to, aspartic acid, arginine, glycine, glutamic acid, proline, threonine, theanine, cysteine, cystine, alanine, valine, tyrosine, leucine, arabinose, trans-4-hydroxyproline, isoleucine, asparagine, serine, lysine, histidine, ornithine, methionine, carnitine, aminobutyric acid ($\alpha$-, $\beta$-, and/or $\delta$-isomers), glutamine, hydroxyproline, taurine, norvaline, sarcosine, and their salt forms such as sodium or potassium salts or acid salts. The amino acid additives also may be in the D- or L-configuration and in the mono-, di-, or tri-form of the same or different amino acids. Additionally, the amino acids may be $\alpha$-, $\beta$-, $\gamma$- and/or $\delta$-isomers if appropriate. Combinations of the foregoing amino acids and their corresponding salts (e.g., sodium, potassium, calcium, magnesium salts or other alkali or alkaline earth metal salts thereof, or acid salts) also are suitable additives in some embodiments. The amino acids may be natural or synthetic. The amino acids also may be modified. Modified amino acids refers to any amino acid wherein at least one atom has been added, removed, substituted, or combinations thereof (e.g., N-alkyl amino acid, N-acyl amino acid, or N-methyl amino acid). Non-limiting examples of modified amino acids include amino acid derivatives such as trimethyl glycine, N-methyl-glycine, and N-methyl-alanine. As used herein, modified amino acids encompass both modified and unmodified amino acids. As used herein, amino acids also encompass both peptides and polypeptides (e.g., dipeptides, tripeptides, tetrapeptides, and pentapeptides) such as glutathione and L-alanyl-L-glutamine. Suitable polyamino acid additives include poly-L-aspartic acid, poly-L-lysine (e.g., poly-L-$\alpha$-lysine or poly-L-$\varepsilon$-lysine), poly-L-ornithine (e.g., poly-L-$\alpha$-ornithine or poly-L-$\varepsilon$-ornithine), poly-L-arginine, other polymeric forms of amino acids, and salt forms thereof (e.g., calcium, potassium, sodium, or magnesium salts such as L-glutamic acid mono sodium salt). The poly-amino acid additives also may be in the D- or L-configuration. Additionally, the poly-amino acids may be $\alpha$-, $\beta$-, $\gamma$-, $\delta$-, and $\varepsilon$-isomers if appropriate.

Combinations of the foregoing poly-amino acids and their corresponding salts (e.g., sodium, potassium, calcium, magnesium salts or other alkali or alkaline earth metal salts thereof or acid salts) also are suitable additives in some embodiments. The poly-amino acids described herein also may comprise co-polymers of different amino acids. The poly-amino acids may be natural or synthetic. The poly-amino acids also may be modified, such that at least one atom has been added, removed, substituted, or combinations thereof (e.g., N-alkyl poly-amino acid or N-acyl poly-amino acid). As used herein, poly-amino acids encompass both modified and unmodified poly-amino acids. For example, modified poly-amino acids include, but are not limited to, poly-amino acids of various molecular weights (MW), such as poly-L-α-lysine with a MW of 1,500, MW of 6,000, MW of 25,200, MW of 63,000, MW of 83,000, or MW of 300,000.

Suitable sugar acid additives include, but are not limited to, aldonic, uronic, aldaric, alginic, gluconic, glucuronic, glucaric, galactaric, galacturonic, and salts thereof (e.g., sodium, potassium, calcium, magnesium salts or other physiologically acceptable salts) and combinations thereof.

Suitable nucleotide additives include, but are not limited to, inosine monophosphate ("IMP"), guanosine monophosphate ("GMP"), adenosine monophosphate ("AMP"), cytosine monophosphate (CMP), uracil monophosphate (UMP), inosine diphosphate, guanosine diphosphate, adenosine diphosphate, cytosine diphosphate, uracil diphosphate, inosine triphosphate, guanosine triphosphate, adenosine triphosphate, cytosine triphosphate, uracil triphosphate, alkali or alkaline earth metal salts thereof, and combinations thereof. The nucleotides described herein also may comprise nucleotide-related additives, such as nucleosides or nucleic acid bases (e.g., guanine, cytosine, adenine, thymine, uracil).

Suitable organic acid additives include any compound which comprises a —COOH moiety, such as, for example, C2-C30 carboxylic acids, substituted hydroxyl C2-C30 carboxylic acids, butyric acid (ethyl esters), substituted butyric acid (ethyl esters), benzoic acid, substituted benzoic acids (e.g., 2,4-dihydroxybenzoic acid), substituted cinnamic acids, hydroxyacids, substituted hydroxybenzoic acids, anisic acid substituted cyclohexyl carboxylic acids, tannic acid, aconitic acid, lactic acid, tartaric acid, citric acid, isocitric acid, gluconic acid, glucoheptonic acids, adipic acid, hydroxycitric acid, malic acid, fruitaric acid (a blend of malic, fumaric, and tartaric acids), fumaric acid, maleic acid, succinic acid, chlorogenic acid, salicylic acid, creatine, caffeic acid, bile acids, acetic acid, ascorbic acid, alginic acid, erythorbic acid, polyglutamic acid, glucono delta lactone, and their alkali or alkaline earth metal salt derivatives thereof. In addition, the organic acid additives also may be in either the D- or L-configuration.

Suitable organic acid additive salts include, but are not limited to, sodium, calcium, potassium, and magnesium salts of all organic acids, such as salts of citric acid, malic acid, tartaric acid, fumaric acid, lactic acid (e.g., sodium lactate), alginic acid (e.g., sodium alginate), ascorbic acid (e.g., sodium ascorbate), benzoic acid (e.g., sodium benzoate or potassium benzoate), sorbic acid and adipic acid. The examples of the organic acid additives described optionally may be substituted with at least one group chosen from hydrogen, alkyl, alkenyl, alkynyl, halo, haloalkyl, carboxyl, acyl, acyloxy, amino, amido, carboxyl derivatives, alkylamino, dialkylamino, arylamino, alkoxy, aryloxy, nitro, cyano, sulfo, thiol, imine, sulfonyl, sulfenyl, sulfinyl, sulfamyl, carboxalkoxy, carboxamido, phosphonyl, phosphinyl, phosphoryl, phosphino, thioester, thioether, anhydride, oximino, hydrazino, carbamyl, phosphor or phosphonato.

Suitable inorganic acid additives include, but are not limited to, phosphoric acid, phosphorous acid, polyphosphoric acid, hydrochloric acid, sulfuric acid, carbonic acid, sodium dihydrogen phosphate, and alkali or alkaline earth metal salts thereof (e.g., inositol hexaphosphate Mg/Ca).

Suitable bitter compound additives include, but are not limited to, caffeine, quinine, urea, bitter orange oil, naringin, quassia and salts thereof.

Suitable flavorants and flavoring ingredient additives include, but are not limited to, vanillin, vanilla extract, mango extract, cinnamon, citrus, coconut, ginger, viridiflorol, almond, menthol (including menthol without mint), grape skin extract, and grape seed extract. "Flavorant" and "flavoring ingredient" are synonymous and can include natural or synthetic substances or combinations thereof. Flavorants also include any other substance which imparts flavor and may include natural or non-natural (synthetic) substances which are safe for human or animals when used in a generally accepted range. Non-limiting examples of proprietary flavorants include Döhler™ Natural Flavoring Sweetness Enhancer K14323 (Döhler™, Darmstadt, Germany), Symrise™ Natural Flavor Mask for Sweeteners 161453 and 164126 (Symrise™, Holzminden, Germany), Natural Advantage™ Bitterness Blockers 1, 2, 9 and 10 (Natural Advantage™, Freehold, N.J., U.S.A.), and Sucramask™ (Creative Research Management, Stockton, Calif., U.S.A.).

Suitable polymer additives include, but are not limited to, chitosan, pectin, pectic, pectinic, polyuronic, polygalacturonic acid, starch, food hydrocolloid or crude extracts thereof (e.g., gum acacia senegal (Fibergum™), gum acacia seyal, carageenan), poly-L-lysine (e.g., poly-L-α-lysine or poly-L-ε-lysine), poly-L-ornithine (e.g., poly-L-α-ornithine or poly-L-ε-ornithine), polypropylene glycol, polyethylene glycol, poly(ethylene glycol methyl ether), polyarginine, polyaspartic acid, polyglutamic acid, polyethylene imine, alginic acid, sodium alginate, propylene glycol alginate, and sodium polyethyleneglycolalginate, sodium hexametaphosphate and its salts, and other cationic polymers and anionic polymers.

Suitable protein or protein hydrolysate additives include, but are not limited to, bovine serum albumin (BSA), whey protein (including fractions or concentrates thereof such as 90% instant whey protein isolate, 34% whey protein, 50% hydrolyzed whey protein, and 80% whey protein concentrate), soluble rice protein, soy protein, protein isolates, protein hydrolysates, reaction products of protein hydrolysates, glycoproteins, and/or proteoglycans containing amino acids (e.g., glycine, alanine, serine, threonine, asparagine, glutamine, arginine, valine, isoleucine, leucine, norvaline, methionine, proline, tyrosine, hydroxyproline, and the like), collagen (e.g., gelatin), partially hydrolyzed collagen (e.g., hydrolyzed fish collagen), and collagen hydrolysates (e.g., porcine collagen hydrolysate).

Suitable surfactant additives include, but are not limited to, polysorbates (e.g., polyoxyethylene sorbitan monooleate (polysorbate 80), polysorbate 20, polysorbate 60), sodium dodecylbenzenesulfonate, dioctyl sulfosuccinate or dioctyl sulfosuccinate sodium, sodium dodecyl sulfate, cetylpyridinium chloride (hexadecylpyridinium chloride), hexadecyltrimethylammonium bromide, sodium cholate, carbamoyl, choline chloride, sodium glycocholate, sodium taurodeoxycholate, lauric arginate, sodium stearoyl lactylate, sodium taurocholate, lecithins, sucrose oleate esters, sucrose stearate esters, sucrose palmitate esters, sucrose laurate esters, and other emulsifiers and the like.

Suitable flavonoid additives are classified as flavonols, flavones, flavanones, flavan-3-ols, isoflavones, or anthocyanidins. Non-limiting examples of flavonoid additives include, but are not limited to, catechins (e.g., green tea extracts such as Polyphenon™ 60, Polyphenon™ 30, and Polyphenon™ 25 (Mitsui Norin Co., Ltd., Japan), polyphenols, rutins (e.g., enzyme modified rutin Sanmelin™ AO (San-fi Gen F.F.I., Inc., Osaka, Japan)), neohesperidin, naringin, neohesperidin dihydrochalcone and the like.

Suitable alcohol additives include, but are not limited to, ethanol.

Suitable astringent compound additives include, but are not limited to, tannic acid, europium chloride (EuCl3), gadolinium chloride (GdCl3), terbium chloride (TbCl3), alum, tannic acid and polyphenols (e.g., tea polyphenols).

Exemplary functional ingredients include, but are not limited to, saponins, antioxidants, dietary fiber sources, fatty acids, vitamins, glucosamine, minerals, preservatives, hydration agents, probiotics, prebiotics, weight management agents, osteoporosis management agents, phytoestrogens, long chain primary aliphatic saturated alcohols, phytosterols and combinations thereof.

In certain embodiments, the functional ingredient is at least one saponin. As used herein, the at least one saponin may comprise a single saponin or a plurality of saponins as a functional ingredient for the composition provided herein. Saponins are glycosidic natural plant products comprising an aglycone ring structure and one or more sugar moieties. Non-limiting examples of specific saponins for use in particular embodiments of the invention include group A acetyl saponin, group B acetyl saponin and group E acetyl saponin. Several common sources of saponins include soybeans, which have approximately 5% saponin content by dry weight, soapwort plants (Saponaria), the root of which was used historically as soap, as well as alfalfa, aloe, asparagus, grapes, chickpeas, yucca, and various other beans and weeds. Saponins may be obtained from these sources by using extraction techniques well known to those of ordinary skill in the art. A description of conventional extraction techniques can be found in U.S. Pat. Appl. No. 2005/0123662, the disclosure of which is expressly incorporated by reference.

In certain embodiments, the functional ingredient is at least one antioxidant. As used herein "antioxidant" refers to any substance which inhibits, suppresses, or reduces oxidative damage to cells and biomolecules. Examples of suitable antioxidants for embodiments of this invention include, but are not limited to, vitamins, vitamin cofactors, minerals, hormones, carotenoids, carotenoid terpenoids, non-carotenoid terpenoids, flavonoids, flavonoid polyphenolics (e.g., bioflavonoids), flavonols, flavones, phenols, polyphenols, esters of phenols, esters of polyphenols, nonflavonoid phenolics, isothiocyanates, and combinations thereof. In some embodiments, the antioxidant is vitamin A, vitamin C, vitamin E, ubiquinone, mineral selenium, manganese, melatonin, α-carotene, β-carotene, lycopene, lutein, zeanthin, crypoxanthin, reservatol, eugenol, quercetin, catechin, gossypol, hesperetin, curcumin, ferulic acid, thymol, hydroxytyrosol, tumeric, thyme, olive oil, lipoic acid, glutathinone, gutamine, oxalic acid, tocopherol-derived compounds, butylated hydroxyanisole (BHA), butylated hydroxytoluene (BHT), ethylenediaminetetraacetic acid (EDTA), tert-butylhydroquinone, acetic acid, pectin, tocotrienol, tocopherol, coenzyme Q10, zeaxanthin, astaxanthin, canthaxantin, saponins, limonoids, kaempfedrol, myricetin, isorhamnetin, proanthocyanidins, quercetin, rutin, luteolin, apigenin, tangeritin, hesperetin, naringenin, erodictyol, flavan-3-ols (e.g., anthocyanidins), gallocatechins, epicatechin and its gallate forms, epigallocatechin and its gallate forms (ECGC) theaflavin and its gallate forms, thearubigins, isoflavone, phytoestrogens, genistein, daidzein, glycitein, anythocyanins, cyaniding, delphinidin, malvidin, pelargonidin, peonidin, petunidin, ellagic acid, gallic acid, salicylic acid, rosmarinic acid, cinnamic acid and its derivatives (e.g., ferulic acid), chlorogenic acid, chicoric acid, gallotannins, ellagitannins, anthoxanthins, betacyanins and other plant pigments, silymarin, citric acid, lignan, antinutrients, bilirubin, uric acid, R-α-lipoic acid, N-acetylcysteine, emblicanin, apple extract, apple skin extract (applephenon), rooibos extract red, rooibos extract, green, hawthorn berry extract, red raspberry extract, green coffee antioxidant (GCA), aronia extract 20%, grape seed extract (VinOseed), cocoa extract, hops extract, mangosteen extract, mangosteen hull extract, cranberry extract, pomegranate extract, pomegranate hull extract, pomegranate seed extract, hawthorn berry extract, pomella pomegranate extract, cinnamon bark extract, grape skin extract, bilberry extract, pine bark extract, pycnogenol, elderberry extract, mulberry root extract, wolfberry (gogi) extract, blackberry extract, blueberry extract, blueberry leaf extract, raspberry extract, turmeric extract, citrus bioflavonoids, black currant, ginger, acai powder, green coffee bean extract, green tea extract, and phytic acid, or combinations thereof. In alternate embodiments, the antioxidant is a synthetic antioxidant such as butylated hydroxytolune or butylated hydroxyanisole, for example. Other sources of suitable antioxidants for embodiments of this invention include, but are not limited to, fruits, vegetables, tea, cocoa, chocolate, spices, herbs, rice, organ meats from livestock, yeast, whole grains or cereal grains.

Particular antioxidants belong to the class of phytonutrients called polyphenols (also known as "polyphenolics"), which are a group of chemical substances found in plants, characterized by the presence of more than one phenol group per molecule. A variety of health benefits may be derived from polyphenols, including prevention of cancer, heart disease, and chronic inflammatory disease and improved mental strength and physical strength, for example. Suitable polyphenols for embodiments of this invention include catechins, proanthocyanidins, procyanidins, anthocyanins, quercerin, rutin, reservatrol, isoflavones, curcumin, punicalagin, ellagitannin, hesperidin, naringin, citrus flavonoids, chlorogenic acid, other similar materials and combinations thereof.

In particular embodiments, the antioxidant is a catechin such as, for example, epigallocatechin gallate (EGCG). In another embodiment, the antioxidant is chosen from proanthocyanidins, procyanidins or combinations thereof. In particular embodiments, the antioxidant is an anthocyanin. In still other embodiments, the antioxidant is chosen from quercetin, rutin or combinations thereof. In yet other embodiments, the antioxidant is reservatrol. In still further embodiments, the antioxidant is an isoflavone. In yet further embodiments, the antioxidant is curcumin. In other embodiments, the antioxidant is chosen from punicalagin, ellagitannin or combinations thereof. In still other embodiments, the antioxidant is chlorogenic acid.

In certain embodiments, the functional ingredient is at least one dietary fiber source. Numerous polymeric carbohydrates having significantly different structures in both composition and linkages fall within the definition of dietary fiber. Such compounds are well known to those skilled in the art, non-limiting examples of which include non-starch polysaccharides, lignin, cellulose, methylcellulose, the hemicelluloses, β-glucans, pectins, gums, mucilage, waxes, inulins, oligosaccharides, fructooligosaccharides, cyclodextrins, chitins and combinations thereof. Although dietary fiber generally is derived from plant sources, indigestible animal products such as chitins are also classified as dietary fiber. Chitin is a polysaccharide composed of units of acetylglucosamine joined by β(1-4) linkages, similar to the linkages of cellulose.

In certain embodiments, the functional ingredient is at least one fatty acid. As used herein, "fatty acid" refers to any straight chain monocarboxylic acid and includes saturated fatty acids, unsaturated fatty acids, long chain fatty acids, medium chain fatty acids, short chain fatty acids, fatty acid precursors (including omega-9 fatty acid precursors), and esterified fatty acids. As used herein, "long chain polyunsaturated fatty acid" refers to any polyunsaturated carboxylic acid or organic acid with a long aliphatic tail. As used herein, "omega-3 fatty acid" refers to any polyunsaturated fatty acid having a first double bond as the third carbon-carbon bond from the terminal methyl end of its carbon chain. In particular embodiments, the omega-3 fatty acid may comprise a long chain omega-3 fatty acid. As used herein, "omega-6 fatty acid" any polyunsaturated fatty acid having a first double bond as the sixth carbon-carbon bond from the terminal methyl end of its carbon chain.

Suitable omega-3 fatty acids for use in embodiments of the present invention can be derived from algae, fish, animals, plants, or combinations thereof, for example. Examples of suitable omega-3 fatty acids include, but are not limited to, linolenic acid, alpha-linolenic acid, eicosapentaenoic acid, docosahexaenoic acid, stearidonic acid, eicosatetraenoic acid and combinations thereof. In some embodiments, suitable omega-3 fatty acids can be provided in fish oils, (e.g., menhaden oil, tuna oil, salmon oil, bonito oil, and cod oil), microalgae omega-3 oils or combinations thereof. In particular embodiments, suitable omega-3 fatty acids may be derived from commercially available omega-3 fatty acid oils such as Microalgae DHA oil (from Martek, Columbia, Md.), OmegaPure (from Omega Protein, Houston, Tex.), Marinol C-38 (from Lipid Nutrition, Channahon, Ill.), Bonito oil and MEG-3 (from Ocean Nutrition, Dartmouth, NS), Evogel (from Symrise, Holzminden, Germany), Marine Oil, from tuna or salmon (from Arista Wilton, Conn.), OmegaSource 2000, Marine Oil, from menhaden and Marine Oil, from cod (from OmegaSource, RTP, NC).

Suitable omega-6 fatty acids include, but are not limited to, linoleic acid, gamma-linolenic acid, dihommo-gamma-linolenic acid, arachidonic acid, eicosadienoic acid, docosadienoic acid, adrenic acid, docosapentaenoic acid and combinations thereof.

Suitable esterified fatty acids for embodiments of the present invention may include, but are not limited to, monoacylglycerols containing omega-3 and/or omega-6 fatty acids, diacylglycerols containing omega-3 and/or omega-6 fatty acids, or triacylglycerols containing omega-3 and/or omega-6 fatty acids and combinations thereof.

In certain embodiments, the functional ingredient is at least one vitamin. Suitable vitamins include vitamin A, vitamin D, vitamin E, vitamin K, vitamin B1, vitamin B2, vitamin B3, vitamin B5, vitamin B6, vitamin B7, vitamin B9, vitamin B12, and vitamin C.

Various other compounds have been classified as vitamins by some authorities. These compounds may be termed pseudo-vitamins and include, but are not limited to, compounds such as ubiquinone (coenzyme Q10), pangamic acid, dimethylglycine, taestrile, amygdaline, flavanoids, para-aminobenzoic acid, adenine, adenylic acid, and s-methylmethionine. As used herein, the term vitamin includes pseudo-vitamins. In some embodiments, the vitamin is a fat-soluble vitamin chosen from vitamin A, D, E, K and combinations thereof. In other embodiments, the vitamin is a water-soluble vitamin chosen from vitamin B1, vitamin B2, vitamin B3, vitamin B6, vitamin B12, folic acid, biotin, pantothenic acid, vitamin C and combinations thereof.

In certain embodiments, the functional ingredient is glucosamine, optionally further comprising chondroitin sulfate.

In certain embodiments, the functional ingredient is at least one mineral. Minerals, in accordance with the teachings of this invention, comprise inorganic chemical elements required by living organisms. Minerals are comprised of a broad range of compositions (e.g., elements, simple salts, and complex silicates) and also vary broadly in crystalline structure. They may naturally occur in foods and beverages, may be added as a supplement, or may be consumed or administered separately from foods or beverages.

Minerals may be categorized as either bulk minerals, which are required in relatively large amounts, or trace minerals, which are required in relatively small amounts. Bulk minerals generally are required in amounts greater than or equal to about 100 mg per day and trace minerals are those that are required in amounts less than about 100 mg per day.

In one embodiment, the mineral is chosen from bulk minerals, trace minerals or combinations thereof. Non-limiting examples of bulk minerals include calcium, chlorine, magnesium, phosphorous, potassium, sodium, and sulfur. Non-limiting examples of trace minerals include chromium, cobalt, copper, fluorine, iron, manganese, molybdenum, selenium, zinc, and iodine. Although iodine generally is classified as a trace mineral, it is required in larger quantities than other trace minerals and often is categorized as a bulk mineral.

In a particular embodiment, the mineral is a trace mineral, believed to be necessary for human nutrition, non-limiting examples of which include bismuth, boron, lithium, nickel, rubidium, silicon, strontium, tellurium, tin, titanium, tungsten, and vanadium.

The minerals embodied herein may be in any form known to those of ordinary skill in the art. For example, in a particular embodiment the minerals may be in their ionic form, having either a positive or negative charge. In another particular embodiment the minerals may be in their molecular form. For example, sulfur and phosphorous often are found naturally as sulfates, sulfides, and phosphates.

In certain embodiments, the functional ingredient is at least one preservative. In particular embodiments of this invention, the preservative is chosen from antimicrobials, antioxidants, antienzymatics or combinations thereof. Non-limiting examples of antimicrobials include sulfites, propionates, benzoates, sorbates, nitrates, nitrites, bacteriocins, salts, sugars, acetic acid, dimethyl dicarbonate (DMDC), ethanol, and ozone. In one embodiment, the preservative is a sulfite. Sulfites include, but are not limited to, sulfur dioxide, sodium bisulfite, and potassium hydrogen sulfite. In another embodiment, the preservative is a propionate. Propionates include, but are not limited to, propionic acid, calcium propionate, and sodium propionate. In yet another embodiment, the preservative is a benzoate. Benzoates include, but are not limited to, sodium benzoate and benzoic acid. In a still further embodiment, the preservative is a sorbate. Sorbates include, but are not limited to, potassium sorbate, sodium sorbate, calcium sorbate, and sorbic acid. In a yet further embodiment, the preservative is a nitrate and/or a nitrite. Nitrates and nitrites include, but are not limited to, sodium nitrate and sodium nitrite. In another embodiment, the at least one preservative is a bacteriocin, such as, for example, nisin. In a further embodiment, the preservative is ethanol. In still another embodiment, the preservative is ozone. Non-limiting examples of antienzymatics suitable for use as preservatives in particular embodiments of the invention include ascorbic acid, citric acid, and metal chelating agents such as ethylenediaminetetraacetic acid (EDTA).

In certain embodiments, the functional ingredient is at least one hydration agent. In a particular embodiment, the hydration agent is an electrolyte. Non-limiting examples of electrolytes include sodium, potassium, calcium, magnesium, chloride, phosphate, bicarbonate, and combinations thereof. Suitable electrolytes for use in particular embodiments of this invention are also described in U.S. Pat. No. 5,681,569, the disclosure of which is expressly incorporated herein by reference. In one embodiment, the electrolyte is obtained from their corresponding water-soluble salt. Non-limiting examples of salts for use in particular embodiments include chlorides, carbonates, sulfates, acetates, bicarbonates, citrates, phosphates, hydrogen phosphates, tartrates, sorbates, citrates, benzoates, or combinations thereof. In other embodiments, the electrolytes are provided by juice, fruit extracts, vegetable extracts, tea, or teas extracts.

In particular embodiments of this invention, the hydration agent is a carbohydrate to supplement energy stores burned by muscles. Suitable carbohydrates for use in particular embodiments of this invention are described in U.S. Pat. Nos. 4,312,856, 4,853,237, 5,681,569, and 6,989,171, the disclosures of which are expressly incorporated herein by reference. Non-limiting examples of suitable carbohydrates include monosaccharides, disaccharides, oligosaccharides, complex polysaccharides or combinations thereof. Non-limiting examples of suitable types of monosaccharides for use in particular embodiments include trioses, tetroses, pentoses, hexoses, heptoses, octoses, and nonoses. Non-limiting examples of specific types of suitable monosaccharides include glyceraldehyde, dihydroxyacetone, erythrose, threose, erythrulose, arabinose, lyxose, ribose, xylose, ribulose, xylulose, allose, altrose, galactose, glucose, gulose, idose, mannose, talose, fructose, psicose, sorbose, tagatose, mannoheptulose, sedoheptulose, octolose, and sialose. Non-limiting examples of suitable disaccharides include sucrose, lactose, and maltose. Non-limiting examples of suitable oligosaccharides include saccharose, maltotriose, and maltodextrin. In other particular embodiments, the carbohydrates are provided by a corn syrup, a beet sugar, a cane sugar, a juice, or a tea.

In another particular embodiment, the hydration agent is a flavanol that provides cellular rehydration. Flavanols are a class of natural substances present in plants, and generally comprise a 2-phenylbenzopyrone molecular skeleton attached to one or more chemical moieties. Non-limiting examples of suitable flavanols for use in particular embodiments of this invention include catechin, epicatechin, gallocatechin, epigallocatechin, epicatechin gallate, epigallocatechin 3-gallate, theaflavin, theaflavin 3-gallate, theaflavin 3'-gallate, theaflavin 3,3' gallate, thearubigin or combinations thereof. Several common sources of flavanols include tea plants, fruits, vegetables, and flowers. In preferred embodiments, the flavanol is extracted from green tea.

In a particular embodiment, the hydration agent is a glycerol solution to enhance exercise endurance. The ingestion of a glycerol containing solution has been shown to provide beneficial physiological effects, such as expanded blood volume, lower heart rate, and lower rectal temperature.

In certain embodiments, the functional ingredient is chosen from at least one probiotic, prebiotic and combination thereof. The probiotic is a beneficial microorganisms that affects the human body's naturally-occurring gastrointestinal microflora. Examples of probiotics include, but are not limited to, bacteria of the genus Lactobacilli, Bifidobacteria, Streptococci, or combinations thereof, that confer beneficial effects to humans. In particular embodiments of the invention, the at least one probiotic is chosen from the genus Lactobacilli. According to other particular embodiments of this invention, the probiotic is chosen from the genus Bifidobacteria. According to still other particular embodiments of this invention, the probiotic is chosen from the genus *Streptococcus*.

Probiotics that may be used in accordance with this invention are well-known to those of skill in the art. Non-limiting examples of foodstuffs comprising probiotics include yogurt, sauerkraut, kefir, kimchi, fermented vegetables, and other foodstuffs containing a microbial element that beneficially affects the host animal by improving the intestinal microbalance.

Prebiotics, in accordance with the teachings of this invention, include, without limitation, mucopolysaccharides, oligosaccharides, polysaccharides, amino acids, vitamins, nutrient precursors, proteins and combinations thereof. According to a particular embodiment of this invention, the prebiotic is chosen from dietary fibers, including, without limitation, polysaccharides and oligosaccharides. Non-limiting examples of oligosaccharides that are categorized as prebiotics in accordance with particular embodiments of this invention include fructooligosaccharides, inulins, isomalto-oligosaccharides, lactilol, lactosucrose, lactulose, pyrodextrins, soy oligosaccharides, transgalacto-oligosaccharides, and xylo-oligosaccharides. In other embodiments, the prebiotic is an amino acid. Although a number of known prebiotics break down to provide carbohydrates for probiotics, some probiotics also require amino acids for nourishment.

Prebiotics are found naturally in a variety of foods including, without limitation, bananas, berries, asparagus, garlic, wheat, oats, barley (and other whole grains), flaxseed, tomatoes, Jerusalem artichoke, onions and chicory, greens (e.g., dandelion greens, spinach, collard greens, chard, kale, mustard greens, turnip greens), and legumes (e.g., lentils, kidney beans, chickpeas, navy beans, white beans, black beans).

In certain embodiments, the functional ingredient is at least one weight management agent. As used herein, "a weight management agent" includes an appetite suppressant and/or a thermogenesis agent. As used herein, the phrases "appetite suppressant", "appetite satiation compositions", "satiety agents", and "satiety ingredients" are synonymous. The phrase "appetite suppressant" describes macronutrients, herbal extracts, exogenous hormones, anorectics, anorexigenics, pharmaceutical drugs, and combinations thereof, that when delivered in an effective amount, suppress, inhibit, reduce, or otherwise curtail a person's appetite. The phrase "thermogenesis agent" describes macronutrients, herbal extracts, exogenous hormones, anorectics, anorexigenics, pharmaceutical drugs, and combinations thereof, that when delivered in an effective amount, activate or otherwise enhance a person's thermogenesis or metabolism.

Suitable weight management agents include macronutrient selected from the group consisting of proteins, carbohydrates, dietary fats, and combinations thereof. Consumption of proteins, carbohydrates, and dietary fats stimulates the release of peptides with appetite-suppressing effects. For example, consumption of proteins and dietary fats stimulates the release of the gut hormone cholecytokinin (CCK), while consumption of carbohydrates and dietary fats stimulates release of Glucagon-like peptide 1 (GLP-1).

Suitable macronutrient weight management agents also include carbohydrates. Carbohydrates generally comprise sugars, starches, cellulose and gums that the body converts into glucose for energy. Carbohydrates often are classified into two categories, digestible carbohydrates (e.g., monosaccharides, disaccharides, and starch) and non-digestible carbohydrates (e.g., dietary fiber). Studies have shown that non-digestible carbohydrates and complex polymeric carbohydrates having reduced absorption and digestibility in the small intestine stimulate physiologic responses that inhibit food intake. Accordingly, the carbohydrates embodied herein desirably comprise non-digestible carbohydrates or carbohydrates with reduced digestibility. Non-limiting examples of such carbohydrates include polydextrose; inulin; monosaccharide-derived polyols such as erythritol, mannitol, xylitol, and sorbitol; disaccharide-derived alcohols such as isomalt, lactitol, and maltitol; and hydrogenated starch hydrolysates. Carbohydrates are described in more detail herein below.

In another particular embodiment weight management agent is a dietary fat. Dietary fats are lipids comprising combinations of saturated and unsaturated fatty acids. Poly-unsaturated fatty acids have been shown to have a greater satiating power than mono-unsaturated fatty acids. Accordingly, the dietary fats embodied herein desirably comprise poly-unsaturated fatty acids, non-limiting examples of which include triacylglycerols.

In a particular embodiment, the weight management agent is an herbal extract. Extracts from numerous types of plants have been identified as possessing appetite suppressant properties. Non-limiting examples of plants whose extracts have appetite suppressant properties include plants of the genus *Hoodia*, *Trichocaulon*, *Caralluma*, *Stapelia*, *Orbea*, *Asclepias*, and *Camelia*. Other embodiments include extracts derived from *Gymnema Sylvestre*, Kola Nut, Citrus Auran tium, Yerba Mate, Griffonia Simplicifolia, Guarana, myrrh, guggul Lipid, and black current seed oil.

The herbal extracts may be prepared from any type of plant material or plant biomass. Non-limiting examples of plant material and biomass include the stems, roots, leaves, dried powder obtained from the plant material, and sap or dried sap. The herbal extracts generally are prepared by extracting sap from the plant and then spray-drying the sap. Alternatively, solvent extraction procedures may be employed. Following the initial extraction, it may be desirable to further fractionate the initial extract (e.g., by column chromatography) in order to obtain an herbal extract with enhanced activity. Such techniques are well known to those of ordinary skill in the art.

In a particular embodiment, the herbal extract is derived from a plant of the genus *Hoodia*, species of which include *H. alstonii, H. currorii, H. dregei, H. flava, H. gordonii, H. jutatae, H. mossamedensis, H. officinalis, H. parviflorai, H. pedicellata, H. pilifera, H. ruschii,* and *H. triebneri*. *Hoodia* plants are stem succulents native to southern Africa. A sterol glycoside of *Hoodia*, known as P57, is believed to be responsible for the appetite-suppressant effect of the *Hoodia* species. In another particular embodiment, the herbal extract is derived from a plant of the genus *Caralluma*, species of which include *C. indica, C. fimbriata, C. attenuate, C. tuberculata, C. edulis, C. adscendens, C. stalagmifera, C. umbellate, C. penicillata, C. russeliana, C. retrospicens, C. Arabica,* and *C. lasiantha*. *Caralluma* plants belong to the same Subfamily as *Hoodia*, Asclepiadaceae. *Caralluma* are small, erect and fleshy plants native to India having medicinal properties, such as appetite suppression, that generally are attributed to glycosides belonging to the pregnane group of glycosides, non-limiting examples of which include caratuberside A, caratuberside B, bouceroside I, bouceroside II, bouceroside III, bouceroside IV, bouceroside V, bouceroside VI, bouceroside VII, bouceroside VIII, bouceroside IX, and bouceroside X. In another particular embodiment, the at least one herbal extract is derived from a plant of the genus *Trichocaulon*. *Trichocaulon* plants are succulents that generally are native to southern Africa, similar to *Hoodia*, and include the species *T. piliferum* and *T. officinale*. In another particular embodiment, the herbal extract is derived from a plant of the genus *Stapelia* or *Orbea*, species of which include *S. gigantean* and *O. variegate*, respectively. Both *Stapelia* and *Orbea* plants belong to the same Subfamily as *Hoodia*, Asclepiadaceae. Not wishing to be bound by any theory, it is believed that the compounds exhibiting appetite suppressant activity are saponins, such as pregnane glycosides, which include stavarosides A, B, C, D, E, F, G, H, I, J, and K. In another particular embodiment, the herbal extract is derived from a plant of the genus *Asclepias*. *Asclepias* plants also belong to the Asclepiadaceae family of plants. Non-limiting examples of *Asclepias* plants include *A. incarnate, A. curassayica, A. syriaca,* and *A. tuberose*. Not wishing to be bound by any theory, it is believed that the extracts comprise steroidal compounds, such as pregnane glycosides and pregnane aglycone, having appetite suppressant effects.

In a particular embodiment, the weight management agent is an exogenous hormone having a weight management effect. Non-limiting examples of such hormones include CCK, peptide YY, ghrelin, bombesin and gastrin-releasing peptide (GRP), enterostatin, apolipoprotein A-IV, GLP-1, amylin, somastatin, and leptin.

In another embodiment, the weight management agent is a pharmaceutical drug. Non-limiting examples include phentenime, diethylpropion, phendimetrazine, sibutramine, rimonabant, oxyntomodulin, floxetine hydrochloride, ephedrine, phenethylamine, or other stimulants.

In certain embodiments, the functional ingredient is at least one osteoporosis management agent. In certain embodiments, the osteoporosis management agent is at least one calcium source. According to a particular embodiment, the calcium source is any compound containing calcium, including salt complexes, solubilized species, and other forms of calcium. Non-limiting examples of calcium sources include amino acid chelated calcium, calcium carbonate, calcium oxide, calcium hydroxide, calcium sulfate, calcium chloride, calcium phosphate, calcium hydrogen phosphate, calcium dihydrogen phosphate, calcium citrate, calcium malate, calcium citrate malate, calcium gluconate, calcium tartrate, calcium lactate, solubilized species thereof, and combinations thereof.

According to a particular embodiment, the osteoporosis management agent is a magnesium source. The magnesium source is any compound containing magnesium, including salt complexes, solubilized species, and other forms of magnesium. Non-limiting examples of magnesium sources include magnesium chloride, magnesium citrate, magnesium gluceptate, magnesium gluconate, magnesium lactate, magnesium hydroxide, magnesium picolate, magnesium sulfate, solubilized species thereof, and mixtures thereof. In another particular embodiment, the magnesium source comprises an amino acid chelated or creatine chelated magnesium.

In other embodiments, the osteoporosis agent is chosen from vitamins D, C, K, their precursors and/or beta-carotene and combinations thereof.

Numerous plants and plant extracts also have been identified as being effective in the prevention and treatment of osteoporosis. Non-limiting examples of suitable plants and plant extracts as osteoporosis management agents include species of the genus *Taraxacum* and *Amelanchier*, as disclosed in U.S. Patent Publication No. 2005/0106215, and species of the genus *Lindera, Artemisia, Acorus, Carthamus, Carum, Cnidium, Curcuma, Cyperus, Juniperus, Prunus, Iris, Cichorium, Dodonaea, Epimedium, Erigonoum, Soya, Mentha, Ocimum, thymus, Tanacetum, Plantago, Spearmint, Bixa, Vitis, Rosemarinus, Rhus,* and *Anethum*, as disclosed in U.S. Patent Publication No. 2005/0079232.

In certain embodiments, the functional ingredient is at least one phytoestrogen. Phytoestrogens are compounds found in plants which can typically be delivered into human bodies by ingestion of the plants or the plant parts having the phytoestrogens. As used herein, "phytoestrogen" refers to any substance which, when introduced into a body causes an estrogen-like effect of any degree. For example, a phytoestrogen may bind to estrogen receptors within the body and have a small estrogen-like effect. Examples of suitable phytoestrogens for embodiments of this invention include, but are not limited to, isoflavones, stilbenes, lignans, resorcyclic acid lactones, coumestans, coumestrol, equol, and combinations thereof. Sources of suitable phytoestrogens include, but are not limited to, whole grains, cereals, fibers, fruits, vegetables, black cohosh, agave root, black currant, black haw, chasteberries, cramp bark, dong quai root, devil's club root, false unicorn root, *ginseng* root, groundsel herb, licorice, liferoot herb, motherwort herb, peony root, raspberry leaves, rose family plants, sage leaves, sarsaparilla root, saw palmetto berried, wild yam root, yarrow blossoms, legumes, soybeans, soy products (e.g., miso, soy flour, soymilk, soy nuts, soy protein isolate, tempen, or tofu) chick peas, nuts, lentils, seeds, clover, red clover, dandelion leaves, dandelion roots, fenugreek seeds, green tea, hops, red wine, flaxseed, garlic, onions, linseed, borage, butterfly weed, caraway, chaste tree, vitex, dates, dill, fennel seed, gotu kola, milk thistle, pennyroyal, pomegranates, southernwood, soya flour, tansy, and root of the kudzu vine (pueraria root) and the like, and combinations thereof.

Isoflavones belong to the group of phytonutrients called polyphenols. In general, polyphenols (also known as "polyphenolics"), are a group of chemical substances found in plants, characterized by the presence of more than one phenol group per molecule.

Suitable phytoestrogen isoflavones in accordance with embodiments of this invention include genistein, daidzein, glycitein, biochanin A, formononetin, their respective naturally occurring glycosides and glycoside conjugates, matairesinol, secoisolariciresinol, enterolactone, enterodiol, textured vegetable protein, and combinations thereof.

Suitable sources of isoflavones for embodiments of this invention include, but are not limited to, soy beans, soy products, legumes, alfalfa sprouts, chickpeas, peanuts, and red clover.

In certain embodiments, the functional ingredient is at least one long chain primary aliphatic saturated alcohol. Long-chain primary aliphatic saturated alcohols are a diverse group of organic compounds. The term alcohol refers to the fact these compounds feature a hydroxyl group (—OH) bound to a carbon atom. Non-limiting examples of particular long-chain primary aliphatic saturated alcohols for use in particular embodiments of the invention include the 8 carbon atom 1-octanol, the 9 carbon 1-nonanol, the 10 carbon atom 1-decanol, the 12 carbon atom 1-dodecanol, the 14 carbon atom 1-tetradecanol, the 16 carbon atom 1-hexadecanol, the 18 carbon atom 1-octadecanol, the 20 carbon atom 1-eicosanol, the 22 carbon 1-docosanol, the 24 carbon 1-tetracosanol, the 26 carbon 1-hexacosanol, the 27 carbon 1-heptacosanol, the 28 carbon 1-octanosol, the 29 carbon 1-nonacosanol, the 30 carbon 1-triacontanol, the 32 carbon 1-dotriacontanol, and the 34 carbon 1-tetracontanol.

In a particularly desirable embodiment of the invention, the long-chain primary aliphatic saturated alcohols are policosanol. Policosanol is the term for a mixture of long-chain primary aliphatic saturated alcohols composed primarily of 28 carbon 1-octanosol and 30 carbon 1-triacontanol, as well as other alcohols in lower concentrations such as 22 carbon 1-docosanol, 24 carbon 1-tetracosanol, 26 carbon 1-hexacosanol, 27 carbon 1-heptacosanol, 29 carbon 1-nonacosanol, 32 carbon 1-dotriacontanol, and 34 carbon 1-tetracontanol.

In certain embodiments, the functional ingredient is at least one phytosterol, phytostanol or combination thereof. As used herein, the phrases "stanol", "plant stanol" and "phytostanol" are synonymous. Plant sterols and stanols are present naturally in small quantities in many fruits, vegetables, nuts, seeds, cereals, legumes, vegetable oils, bark of the trees and other plant sources. Sterols are a subgroup of steroids with a hydroxyl group at C-3. Generally, phytosterols have a double bond within the steroid nucleus, like cholesterol; however, phytosterols also may comprise a substituted side chain (R) at C-24, such as an ethyl or methyl group, or an additional double bond. The structures of phytosterols are well known to those of skill in the art.

At least 44 naturally-occurring phytosterols have been discovered, and generally are derived from plants, such as corn, soy, wheat, and wood oils; however, they also may be produced synthetically to form compositions identical to those in nature or having properties similar to those of naturally-occurring phytosterols. According to particular embodiments of this invention, non-limiting examples of phytosterols well known to those or ordinary skill in the art include 4-desmethylsterols (e.g., β-sitosterol, campesterol, stigmasterol, brassicasterol, 22-dehydrobrassicasterol, and Δ5-avenasterol), 4-monomethyl sterols, and 4,4-dimethyl sterols (triterpene alcohols) (e.g., cycloartenol, 24-methylenecycloartanol, and cyclobranol).

As used herein, the phrases "stanol", "plant stanol" and "phytostanol" are synonymous. Phytostanols are saturated sterol alcohols present in only trace amounts in nature and also may be synthetically produced, such as by hydrogenation of phytosterols. According to particular embodiments of this invention, non-limiting examples of phytostanols include β-sitostanol, campestanol, cycloartanol, and saturated forms of other triterpene alcohols.

Both phytosterols and phytostanols, as used herein, include the various isomers such as the α and β isomers (e.g., α-sitosterol and β-sitostanol, which comprise one of the most effective phytosterols and phytostanols, respectively, for lowering serum cholesterol in mammals).

The phytosterols and phytostanols of the present invention also may be in their ester form. Suitable methods for deriving the esters of phytosterols and phytostanols are well known to those of ordinary skill in the art, and are disclosed in U.S. Pat. Nos. 6,589,588, 6,635,774, 6,800,317, and U.S. Patent Publication Number 2003/0045473, the disclosures of which are incorporated herein by reference in their entirety. Non-limiting examples of suitable phytosterol and phytostanol esters include sitosterol acetate, sitosterol oleate, stigmasterol oleate, and their corresponding phytostanol esters. The phytosterols and phytostanols of the present invention also may include their derivatives.

Generally, the amount of functional ingredient in the composition varies widely depending on the particular composition and the desired functional ingredient. Those of ordinary skill in the art will readily ascertain the appropriate amount of functional ingredient for each composition.

In one embodiment, a method for preparing a composition comprises combining at least one target steviol glycoside and at least one sweetener and/or additive and/or functional ingredient.

In a particular embodiment, a method for preparing a composition comprises combining at least one target steviol glycoside and at least one additional sweetener and/or additive and/or functional ingredient.

Consumables

In one embodiment, the present invention is a consumable comprising at least one target steviol glycoside, or a composition comprising at least one target steviol glycoside. In a particular embodiment, the at least one target steviol glycoside is purified.

The target steviol glycoside, or a composition comprising the same, can be admixed with any known edible or oral composition, referred to herein as a "consumable". The term "consumable(s)", as used herein, mean substances which are contacted with the mouth of man or animal, including substances which are taken into and subsequently ejected from the mouth and substances which are drunk, eaten, swallowed or otherwise ingested, and are safe for human or animal consumption when used in a generally acceptable range.

Exemplary consumables include pharmaceutical compositions, edible gel mixes and compositions, dental compositions, foodstuffs (confections, condiments, chewing gum, cereal compositions baked goods dairy products, and table-top sweetener compositions), beverages and beverage products. The consumables of the present invention require admixing and, as such, do not occur in nature.

For example, a beverage is a consumable. The beverage may be sweetened or unsweetened. The target steviol glycoside, or composition comprising the same, may be added to a beverage or beverage matrix to sweeten the beverage or enhance its existing sweetness or flavor.

In one embodiment, the present invention is a consumable comprising at least one target steviol glycoside. In particular embodiments, a target steviol glycoside is present in the consumable in a concentration from about 50 ppm to about 1,000 ppm, such as, for example, from about 100 ppm to about 1,000 ppm, from about 200 ppm to about 1,000 ppm, from about 300 ppm to about 1,000 ppm, from about 400 ppm to about 1,000 ppm or from about 500 ppm to about 1,000 ppm. In a more particular embodiment, a target steviol glycoside is present in the consumable in a concentration from about 100 ppm to about 600 ppm, such as, for example, from about 200 ppm to about 600 ppm, from about 300 ppm to about 600 ppm, from about 400 ppm to about 600 ppm and from about 500 ppm to about 600 ppm.

In other particular embodiments, a target steviol glycoside is provided as a composition. Any composition described hereinabove can be used. In still other embodiments, a target steviol glycoside is provided to the consumable in >99% purity by weight on a dry basis.

The consumable can optionally include additives, additional sweeteners, functional ingredients and combinations thereof, as described herein. Any of the additive, additional sweetener and functional ingredients described above can be present in the consumable.

In another embodiment, the present invention is a beverage or beverage product comprising a composition that comprises at least one target steviol glycoside. In a particular embodiment, the beverage or beverage product comprises a composition comprising at least one purified target steviol glycoside.

As used herein a "beverage product" is a ready-to-drink beverage, a beverage concentrate, a beverage syrup, or a powdered beverage. Suitable ready-to-drink beverages include carbonated and non-carbonated beverages. Carbonated beverages include, but are not limited to, enhanced sparkling beverages, cola, lemon-lime flavored sparkling beverage, orange flavored sparkling beverage, grape flavored sparkling beverage, strawberry flavored sparkling beverage, pineapple flavored sparkling beverage, ginger-ale, soft drinks and root beer. Non-carbonated beverages include, but are not limited to fruit juice, fruit-flavored juice, juice drinks, nectars, vegetable juice, vegetable-flavored juice, sports drinks, energy drinks, enhanced water drinks, enhanced water with vitamins, near water drinks (e.g., water with natural or synthetic flavorants), coconut water, tea type drinks (e.g. black tea, green tea, red tea, oolong tea), coffee, cocoa drink, beverage containing milk components (e.g. milk beverages, coffee containing milk components, café au lait, milk tea, fruit milk beverages), beverages containing cereal extracts, smoothies and combinations thereof.

Beverage concentrates and beverage syrups are prepared with an initial volume of liquid matrix (e.g. water) and the desired beverage ingredients. Full strength beverages are then prepared by adding further volumes of water. Powdered beverages are prepared by dry-mixing all of the beverage ingredients in the absence of a liquid matrix. Full strength beverages are then prepared by adding the full volume of water.

Beverages comprise a matrix, i.e. the basic ingredient in which the ingredients—including the compositions of the present invention—are dissolved. In one embodiment, a beverage comprises water of beverage quality as the matrix, such as, for example deionized water, distilled water, reverse osmosis water, carbon-treated water, purified water, demineralized water and combinations thereof, can be used. Additional suitable matrices include, but are not limited to phosphoric acid, phosphate buffer, citric acid, citrate buffer and carbon-treated water.

In one embodiment, the present invention is a beverage comprising at least one target steviol glycoside.

In a further embodiment, the present invention is a beverage product comprising at least one target steviol glycoside.

The at least one target steviol glycoside can be provided as a single compound or as part of any composition described above. In an exemplary embodiment, the at least one target steviol glycoside is purified.

In a particular embodiment, a beverage or beverage product comprises at least one target steviol glycoside in purified form and at least one other substance that does not occur with the target steviol glycoside in nature, i.e. *Stevia* leaf. In one embodiment, the at least other additional substance modulates the taste profile of the at least one target steviol glycoside to provide a beverage with a more sucrose-like taste profile compared to the target steviol glycoside in nature and (if applicable) the at least one other substance in nature. For example, in certain embodiments the beverage exhibits one or more of the following characteristics: improved sweetness potency, improved mouthfeel, decreased sweetness linger, decreased bitterness and/or decreased metallic taste.

The concentration of the target steviol glycoside in the beverage may be above, at or below the threshold sweetness or flavor recognition concentration of the target steviol glycoside.

In one embodiment, a target steviol glycoside is present in the beverage in a concentration greater than about 1 ppm, such as, for example, from about 1 ppm to about 1,000 ppm, from about 25 ppm to about 1,000 ppm, from about 50 ppm to about 1,000 ppm, from about 75 ppm to about 1,000 ppm, from about 100 ppm to about 1,000 ppm, from about 200 ppm to about 1,000 ppm, from about 300 ppm to about 1,000 ppm, from about 400 ppm to about 1,000 ppm or from about 500 ppm to about 1,000 ppm.

In a more particular embodiment, a target steviol glycoside is present in the beverage in a concentration from about 25 ppm to about 600 ppm, such as, for example, from about 25 ppm to about 500 ppm, from about 25 ppm to about 400 ppm, from about 25 ppm to about 300 ppm, from about 25 ppm to about 200 ppm, from about 25 ppm to about 100 ppm, from about 50 ppm to about 600 ppm, from about 50 ppm to about 500 ppm, from about 50 ppm to about 400 ppm, from about 50 ppm to about 300 ppm, from about 50 ppm to about 200 ppm, from about 50 ppm to about 100 ppm, from about 100 ppm to about 600 ppm, from about 100 ppm to about 500 ppm, from about 100 ppm to about 400 ppm, from about 100 ppm to about 300 ppm, from about 100 ppm to about 200 ppm, from about 200 ppm to about 600 ppm, from about 200 ppm to about 500 ppm, from about 200 ppm to about 400 ppm, from about 200 ppm to about 300 ppm, from about 300 ppm to about 600 ppm, from about 300 ppm to about 500 ppm, from about 300 ppm to about 400 ppm, from about 400 ppm to about 600 ppm, from about 400 ppm to about 500 ppm or from about 500 ppm to about 600 ppm.

In other particular embodiments, a target steviol glycoside is present in the beverage in a purity of at least about 5% with respect to a mixture of steviol glycosides or *Stevia* extract, such as, for example, at least about 10%, at least about 20%, at least about 30%, at least about 40%, at least about 50%, at least about 60%, at least about 70%, at least about 80%, at least about 90%, at least about 95% or at least about 97%. In still other embodiments, a target steviol glycoside is present in the beverage in >99% purity.

The beverage can include one or more sweeteners. Any of the sweeteners detailed herein can be used, including natural, non-natural, or synthetic sweeteners. These may be added to the beverage either before, contemporaneously with or after the at least one target steviol glycoside.

It is contemplated that the pH of the consumable, such as, for example, a beverage, does not materially or adversely affect the taste of the sweetener. A non-limiting example of the pH range of the beverage may be from about 1.8 to about 10. A further example includes a pH range from about 2 to about 5. In a particular embodiment, the pH of beverage can be from about 2.5 to about 4.2. On of skill in the art will understand that the pH of the beverage can vary based on the type of beverage. Dairy beverages, for example, can have pHs greater than 4.2.

The titratable acidity of a beverage may, for example, range from about 0.01 to about 1.0% by weight of beverage.

In one embodiment, the sparkling beverage product has an acidity from about 0.01 to about 1.0% by weight of the beverage, such as, for example, from about 0.05% to about 0.25% by weight of beverage.

The carbonation of a sparkling beverage product has 0 to about 2% (w/w) of carbon dioxide or its equivalent, for example, from about 0.1 to about 1.0% (w/w).

The temperature of a beverage may, for example, range from about 4° C. to about 100° C., such as, for example, from about 4° C. to about 25° C.

The beverage can be a full-calorie beverage that has up to about 120 calories per 8 oz serving.

The beverage can be a mid-calorie beverage that has up to about 60 calories per 8 oz serving.

The beverage can be a low-calorie beverage that has up to about 40 calories per 8 oz serving.

The beverage can be a zero-calorie that has less than about 5 calories per 8 oz. serving.

In one embodiment, the beverage comprises natural sweetener(s) only, i.e. the only type of sweetener(s) are naturally-occurring.

III. Methods of Use

The target steviol glycosides and compositions of the present invention can be used to impart sweetness or to enhance the flavor or sweetness of consumables or other compositions.

In one aspect, the present invention is a method of preparing a sweetened consumable comprising (i) providing a consumable and (ii) adding at least one target steviol glycoside of the present invention to the consumable to provide a sweetened consumable.

In a particular embodiment, a method of preparing a sweetened consumable comprises (i) providing an unsweetened consumable and (ii) adding at least one target steviol glycoside of the present invention to the unsweetened consumable to provide a sweetened consumable.

In a particular embodiment, the present invention is a method of preparing a sweetened beverage comprising (i) providing a beverage and (ii) adding at least one target steviol glycoside of the present invention to the beverage to provide a sweetened beverage.

In a particular embodiment, the present invention is a method of preparing a sweetened beverage comprising (i) providing an unsweetened beverage and (ii) adding at least one target steviol glycoside of the present invention to the unsweetened beverage to provide a sweetened beverage.

In the above methods, the target steviol glycoside(s) of the present invention may be provided as such, i.e., in the form of a purified compound, or in form of a composition. When provided as a composition, the amount of target steviol glycoside in the composition is effective to provide a concentration that is above its sweetness recognition threshold when added to the consumable (e.g., the beverage). When the target steviol glycoside(s) of the present invention is provided as a purified compound, it may be added to the consumable at a concentration that is above its sweetness recognition threshold.

The following examples illustrate preferred embodiments of the invention. It will be understood that the invention is not limited to the materials, proportions, conditions and procedures set forth in the examples, which are only illustrative.

Example 1: Preparation of CC-00326

Preparation of Dextran Sucrase from *Leuconostoc lactis* EG001

The amino-acid sequence for Dextran Sucrase from *Leuconostoc Lactis* EG001 was retrieved from UniProt under the accession number C7DT60. The synthetic gene was prepared by DNA2.0. The initial Methionine was deleted and NcoI and NotI cloning sites were introduced for cloning in pET22b+ vector (Invitrogen) allowing the addition of a C-terminal HIS-tag and an N-terminal pelB signal (DS-LeuLac_pET22b+).

E. coli BL21 (DE3) cells harboring the DS-LeuLac_pET22b+ plasmid were grown in Overnight Express™ instant LB medium (Novagen) at 30° C. Cells were collected by centrifugation. Frozen cells were mechanically lysed and the DS-LeuLac lysate was recovered by centrifugation. DS-LeuLac was stored frozen.

Activity Test of DS-LeuLac Lysate

The activity of DS-LeuLac was determined by measuring the amount of reducing sugars (3,5-dinitrosalicylic acid assay) that was produced from sucrose (100 g/L) in 20 mM sodium acetate buffer pH 5.5 in the presence of 0.02 g/L $CaCl_2$ at 30° C. An activity of 370 U/g was determined (1 U corresponds to the production of 1 μmol of reducing sugar per minute per g of harvested cells under the assay conditions).

Conversion of Rebaudioside A to CC-00326 (Reb_A_G1) Using DS-LeuLac

Figure 3:
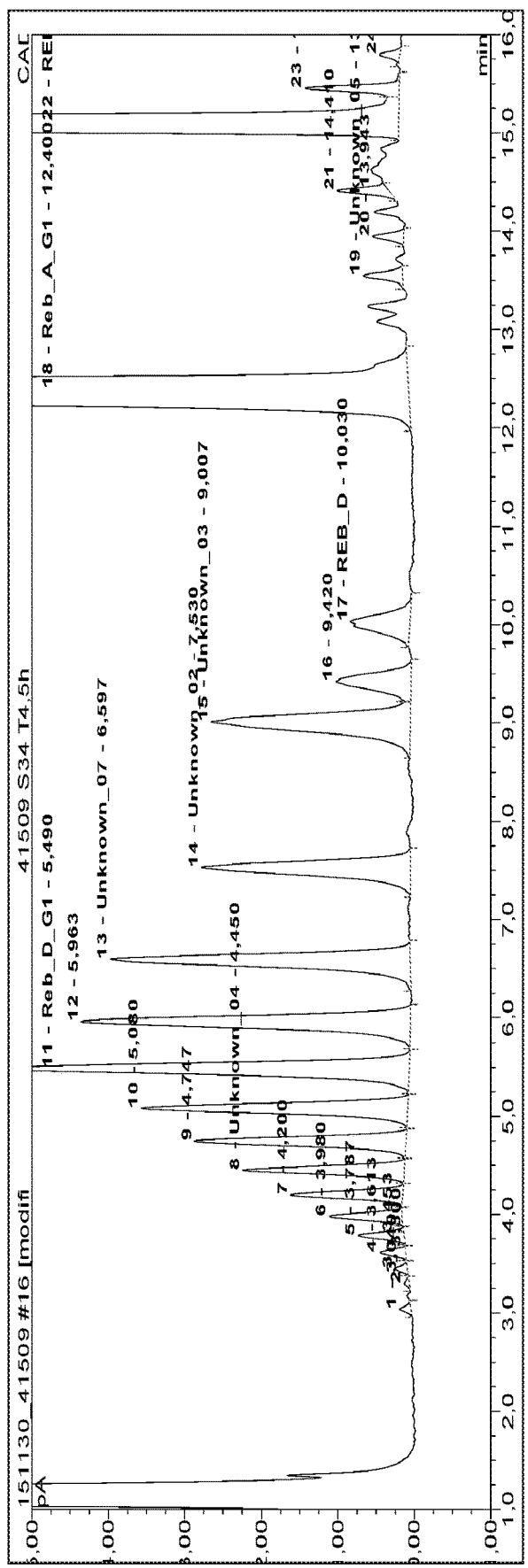
FIG. 3 shows the reaction mixture of the bioconversion from rebaudioside A to CC-00326 after 4.5 hours. CC-00326 is referred to as Reb_A_G1.
Figure 4:
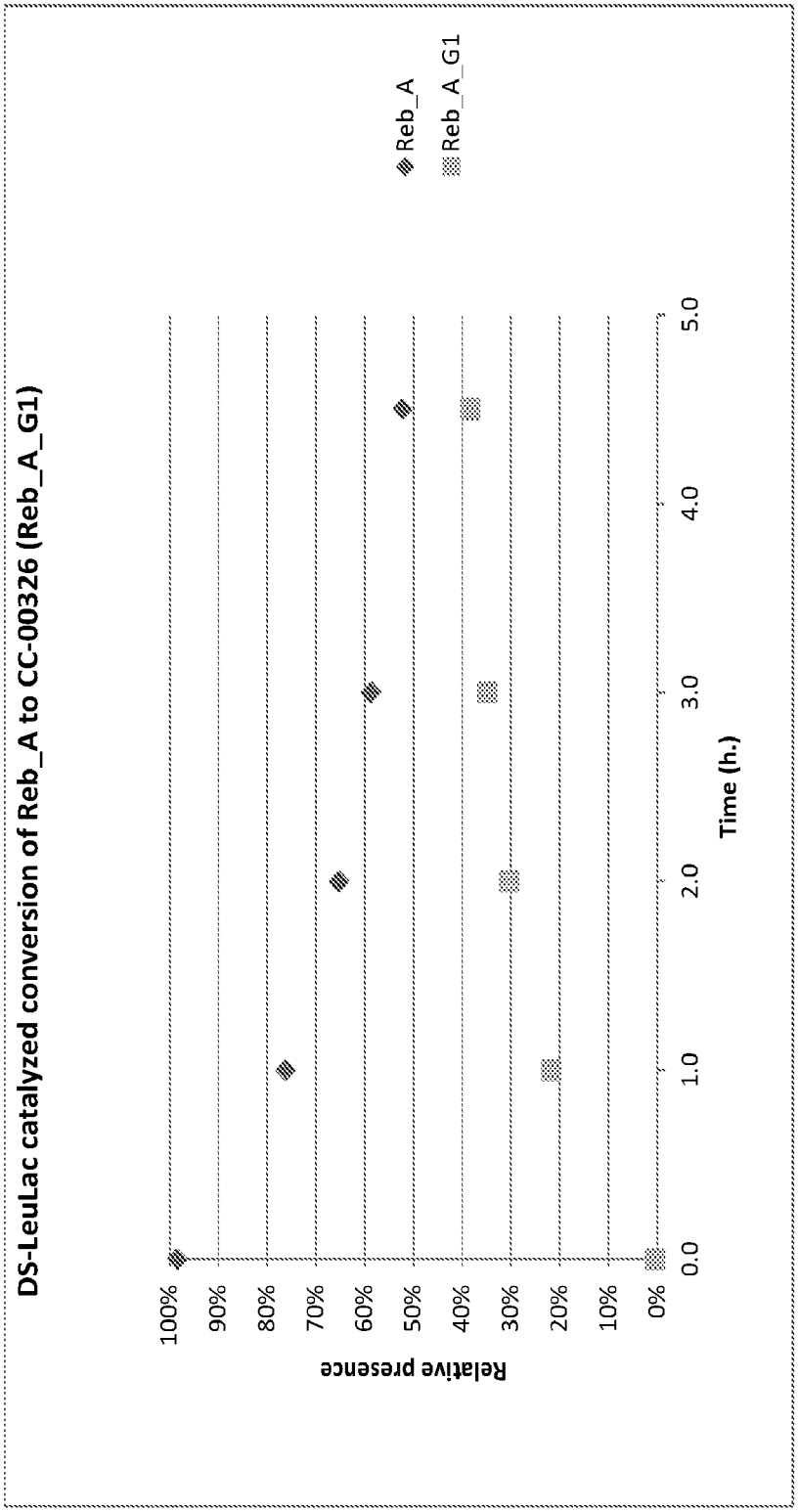
FIG. 4 shows the reaction profile of the bioconversion from rebaudioside A to CC-00326. CC-00326 is referred to as Reb_A_G1.

On a 1 L scale, 15 mM of Rebaudioside A was converted to CC-00326 at 30° C. under the following conditions: 50 mM Sodium acetate buffer pH 5.2; 0.05 g/L of $CaCl_2$; 250 mM of sucrose and 500 U/L of DS-LeuLac. The reaction was followed by HPLC (FIGS. 3 and 4) using the method described below. After 4.5 hours, the reaction was quenched with 500 mL of ethanol and stored at −20° C. overnight. After centrifugation of the suspension, the crude supernatant was used for isolation of CC-00326 (Reb_A_G1).

HPLC Method Gradient

| Time (min) | Water containing 0.1% Formic acid | Acetonitrile |
|---|---|---|
| 0 | 80 | 20 |
| 9 | 80 | 20 |
| 13 | 70 | 30 |
| 14 | 70 | 30 |
| 15 | 80 | 20 |
| 20 | 80 | 20 |

Column: KINETEX C18 100A 2.6 μm 4.6×100 mm (Phenomenex Ref.: 00D-4462-EU)

Flow: 0.8 mL/min

Temperature: 45° C.

Detection: Corona Veo SD

Example 2: Isolation and Characterization of CC-00326

Analytical HPLC Methods.

HPLC analyses were performed on a Waters 2695 Alliance System coupled to a Waters 996 Photo Diode Array (PDA) detector. In addition, final sample purities were assessed using an ESA Corona Charged Aerosol Detector (CAD). Sample analyses were performed using the method conditions described in Tables 1 and 2.

TABLE 1

Analytical HPLC Conditions for Fraction Analysis.

| | |
|---|---|
| Column | Waters Atlantis dC18 (4.6 × 150 mm, 5 μm) |
| Column Temperature (° C.) | Ambient |
| Sample Temperature (° C.) | Ambient |
| Mobile Phase | 78:22 Water/Acetonitrile (MeCN) |
| Flow Rate (mL/min) | 1.0 |
| Detection | CAD and UV at 210 nm |

TABLE 2

Analytical HPLC Conditions for Fraction Analysis.

| | | | |
|---|---|---|---|
| Column | Phenomenex Synergi Hydro-RP (4.6 × 250 mm, 4 μm) | | |
| Column Temperature (° C.) | 55 | | |
| Sample Temperature (° C.) | Ambient | | |
| Mobile Phases | (A) 0.0284% ammonium acetate ($NH_4OAc$) and 0.0116% acetic acid (HOAc) in water (B) MeCN | | |
| Flow Rate (mL/min) | 1.0 | | |
| Detection | CAD and UV at 210 nm | | |

| Gradient | | |
|---|---|---|
| Time (min) | % A | % B |
| 0.0-8.5 | 75 | 25 |
| 10.0 | 71 | 29 |
| 16.5 | 70 | 30 |
| 18.5-24.5 | 66 | 34 |
| 26.5-29.0 | 48 | 52 |
| 31.0-37.0 | 30 | 70 |
| 38.0 | 75 | 25 |

Primary Preparative HPLC Method.

Primary processing of material obtained via the process described in Example 1 was performed using pre-packed Waters Atlantis dC18 (50×250 mm, 10 μm). The purification process was performed with a Waters Delta Prep LC Model 2000/4000 system coupled to a UV-Vis detector. Details of the preparative method are summarized in Table 3.

TABLE 3

Conditions for Primary Preparative HPLC Method.

| Primary Preparative HPLC method for the Isolation of CC-00326 | | |
|---|---|---|
| Column | Waters Atlantis dC18 (50 × 250 mm, 10 μm) | |
| Flow Rate (mL/min) | 117 | |
| Detection | UV at 210 nm | |
| Primary Processing | | |
| Mobile Phases | (A) 22% MeCN in water (B) MeCN | |
| Load (g) | 1.1 | |
| Sample preparation | dissolve in MP-A | |
| Isocratic Method with Flush | | |
| Time (min) | % A | % B |
| 0.0-50.0 | 100 | 0 |
| 50.0-60.0 | 20 | 80 |
| 61.0-71.0 | 100 | 0 |

Isolation Procedure.

Fractions collected during the final pre-concentration step were concentrated in vacuo using a Buchi® Rotary Evaporator, Model R-114. The concentrated solution was dried for 48-72 h using the Kinetics Flexi-Dry Personal Freeze Dryer.

MS and MS/MS.

MS and MS/MS data were generated with a Waters QT of Micro mass spectrometer equipped with an electrospray ionization source. Samples were analyzed by negative ESI. Samples were diluted with $H_2O$:acetonitrile (1:1) by 50 fold and introduced via infusion using the onboard syringe pump. The samples were diluted to yield good s/n which occurred at an approximate concentration of 0.01 mg/mL.

NMR.

The sample was prepared by dissolving 10.2 mg in 150 μL of pyridine-d5 and NMR data were acquired on a Bruker Avance 500 MHz instrument with a 2.5 mm inverse detection probe. The $^1H$ NMR spectrum was referenced to the residual solvent signal ($\delta_H$ 8.74 and $\delta_C$ 150.35 for pyridine-d5).

Results and Discussion

Unless otherwise noted, all solvent ratios are listed as percent by volume (v/v).

Primary Purification of CC-00326.

Approximately 1.83 g was processed using the primary preparative HPLC method described in Table 3. Collected fractions were analyzed by HPLC using the analytical method summarized in Table 1. Desired fractions were pooled.

Final Batch Preparation.

Figure 5:
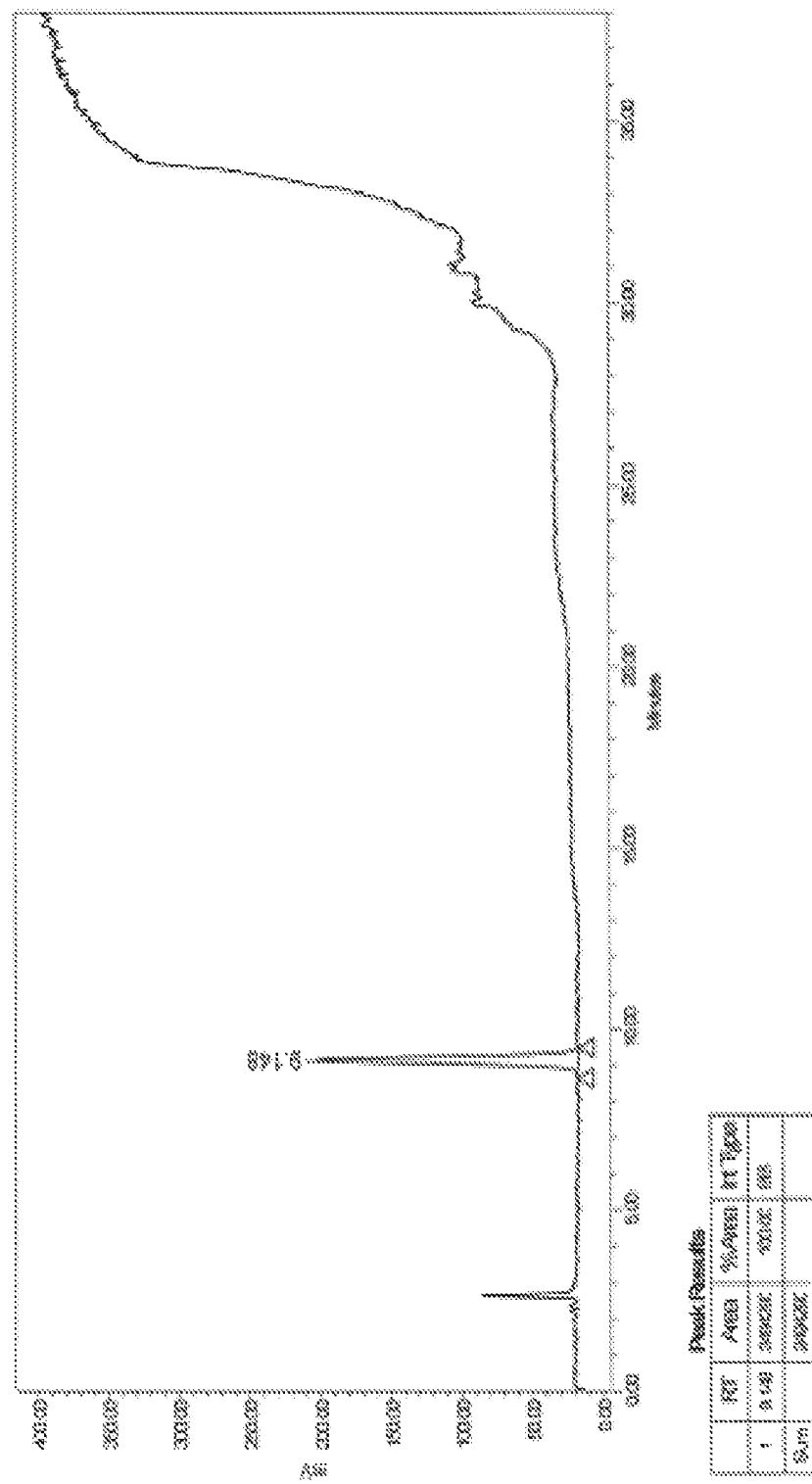
FIG. 5 shows the HPLC trace of purified CC-00326.

CC-00326 was isolated in a single batch and identified by NMR analysis. The solution was then concentrated by rotary evaporation and lyophilized for 48-72 h. The HPLC analysis was performed using the method summarized in Table 2 and the trace is presented in FIG. 5. The final batch had a purity of >99% (AUC, CAD).

Mass Spectrometry.

The ESI-TOF mass spectrum acquired by infusing a sample of CC-00326 showed a [M-H]$^-$ ion at m/z 1127.4745. The mass of the [M-H]$^-$ ion was in good agreement with the molecular formula $C_{50}H_{80}O_{28}$ (calcd for $C_{50}H_{79}O_{28}$: 1127.4758, error: −1.2 ppm) expected. The MS data confirmed that CC-00326 has a nominal mass of 1128 Daltons with the molecular formula, $C_{50}H_{80}O_{28}$.

The MS/MS spectrum of CC-00326, selecting the [M-H]$^-$ ion at m/z 1127.4 for fragmentation, indicated loss of two glucose units at m/z 805.3783; however, it did not show any additional fragmentation with collision energy of 20 eV. When higher collision energy was applied (60-70 eV), the parent ion was not observed but the ion at m/z 803.3920 was again observed corresponding to loss of two glucose. The ion at m/z 641.3406 corresponds to loss of third glucose unit followed by loss of two additional glucose units at m/z 479.2864 and 317.2431. The mass fragmentation pattern thus indicated the presence of five glucose units in the structure.

NMR Spectroscopy.

A series of NMR experiments including $^1H$ NMR (500 MHz, pyridine-d5), $^{13}C$ NMR (125 MHz, pyridine-d5), $^1H$-$^1H$ COSY (500 MHz, pyridine-d5), HSQC-DEPT (500 MHz, pyridine-d5), HMBC (500 MHz, pyridine-d5), ROESY (500 MHz, pyridine-d5), and 1D TOCSY (500 MHz, pyridine-d5 over a range of mixing times (40-140 msec) at 300 K) were acquired to assign CC-00326.

The $^1H$, $^1H$-$^1H$ COSY, $^1H$-$^{13}C$ HSQC-DEPT and $^1H$-$^{13}C$ HMBC NMR data indicated that the central core of the glycoside is a diterpene. The presence of five anomeric protons observed in the $^1H$ and $^1H$-$^{13}C$ HSQC-DEPT spectra confirmed five sugar units in the structure. The methylene $^{13}C$ resonance at $\delta_C$ 68.4 in the $^1H$-$^{13}C$ HSQC-DEPT spectrum indicated the presence of a 1→6 sugar linkage in the structure. The linkages of sugar units were assigned using $^1H$-$^{13}C$ HMBC and 1D-TOCSY correlations.

Figure 6:
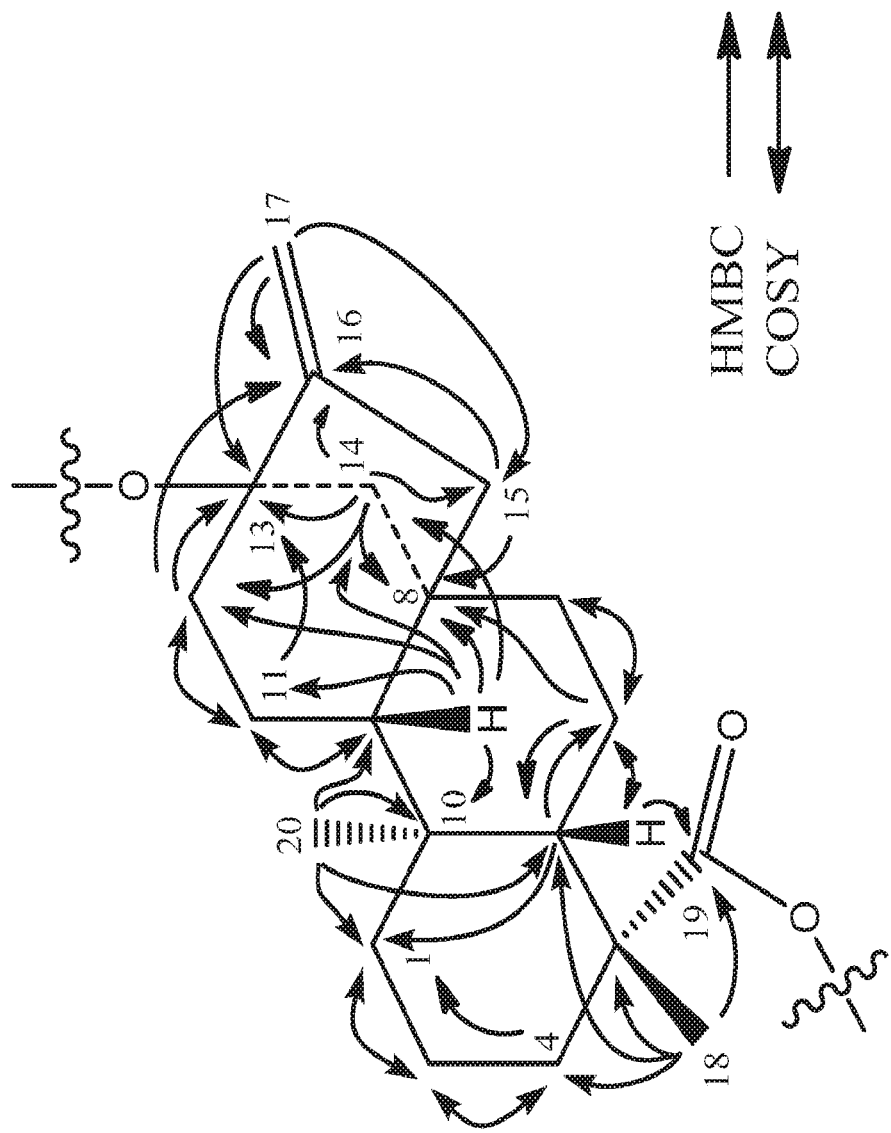
FIG. 6 shows a summary of the HMBC and COSY correlations used to determine the diterpene core of CC-00326.

A summary of the $^1H$ and $^{13}C$ chemical shifts for the aglycone are found in Table 4 and a summary of the key HMBC and COSY correlations used to assign the aglycone region are provided in FIG. 6.

TABLE 4

$^1H$ and $^{13}C$ NMR (500 and 125 MHz, pyridine-d5), assignments of CC-00326 aglycone.

| Position | CC-00326 $^{13}C$ | $^1H$ |
|---|---|---|
| 1 | 41.3 | 0.75 t (11.5) |
|   |   | 1.77 m |
| 2 | 19.9 | 1.43 m |
|   |   | 2.20 m |
| 3 | 38.8 | 1.00 m |
|   |   | 2.38 m |
| 4 | 44.6 | — |
| 5 | 57.8 | 1.04 m |
| 6 | 22.8 | 1.91 m |
|   |   | 2.41 m |
| 7 | 42.2 | 1.30* m |
| 8 | 43.1 | — |
| 9 | 54.5 | 0.89 brd (6.8) |
| 10 | 40.4 | — |
| 11 | 21.2 | 1.65 m |
|   |   | 1.70 m |
| 12 | 37.5 | 1.99 m |
|   |   | 2.28 m |
| 13 | 87.0 | — |
| 14 | 44.9 | 1.81 m |
|   |   | 2.65 d (11.6) |
| 15 | 48.2 | 2.05* brs |
| 16 | 154.8 | — |
| 17 | 105.1 | 5.01 brs |
|   |   | 5.63 brs |
| 18 | 28.8 | 1.29 s |
| 19 | 177.6 | — |
| 20 | 16.1 | 1.32 s |

*Two protons

A summary of the $^1H$ and $^{13}C$ chemical shifts for the glycoside at C-19 are found in Table 5.

TABLE 5

$^1H$ and $^{13}C$ NMR (500 and 125 MHz, pyridine-d5), Assignments of the CC-00326 C-19 glycoside.

| Position | CC-00326 $^{13}C$ | $^1H$ |
|---|---|---|
| Glc$_I$-1 | 96.0 | 6.04 d (7.6) |
| Glc$_I$-2 | 74.2 | 4.08 m |
| Glc$_I$-3 | 79.0 or 79.1 or 79.4 | 4.10 m |
| Glc$_I$-4 | 72.0 or 72.1 | 4.13 m |
| Glc$_I$-5 | 77.6 | 3.98 m |
| Glc$_I$-6 | 68.4 | 4.21 m |
|   |   | 4.47 m |
| Glc$_{VII}$-1 | 100.9 | 5.36 (3.6) |
| Glc$_{VII}$-2 | 74.5$^¥$ | 4.11 m |
| Glc$_{VII}$-3 | 75.9 | 4.57 m |
| Glc$_{VII}$-4 | 72.4$^§$ | 4.24 m |
| Glc$_{VII}$-5 | 74.5$^¥$ | 4.46 m |
| Glc$_{VII}$-6 | 63.1 or 63.2 or 63.4 | 4.47 m |
|   |   | 4.40 m |

$^¥$Two carbons, δc 74.46 and 74.50.
$^§$Two carbons, δc 72.38 and 72.43

A summary of the $^1H$ and $^{13}C$ chemical shifts for the glycoside at C-13 are found in Table 6.

TABLE 6

$^1$H and $^{13}$C NMR (500 and 125 MHz, pyridine-$d_5$),
Assignments of the CC-00326 C-13 glycoside.

| Position | CC-00326 | |
|---|---|---|
| | $^{13}$C | $^1$H |
| Glc$_{II}$-1 | 98.8 | 5.08 (~7.7)$^\epsilon$ |
| Glc$_{II}$-2 | 81.3 | 4.37 m |
| Glc$_{II}$-3 | 88.3 | 4.19 m |
| Glc$_{II}$-4 | 71.1 | 3.88 t (9.2) |
| Glc$_{II}$-5 | 77.9 | 3.78 m |
| Glc$_{II}$-6 | 63.1 or 63.2 or 63.4 | 4.09 m |
| | | 4.45 m |
| Glc$_{III}$-1 | 105.3 | 5.56 d (7.7) |
| Glc$_{III}$-2 | 76.8 | 4.18 m |
| Glc$_{III}$-3 | 78.7 or 78.8 | 4.25 m |
| Glc$_{III}$-4 | 72.4$^\S$ | 4.27 m |
| Glc$_{III}$-5 | 78.7 or 78.8 | 3.93 m |
| Glc$_{III}$-6 | 63.1 or 63.2 or 63.4 | 4.40 m |
| | | 4.49 m |
| Glc$_{IV}$-1 | 105.3 | 5.33 d (7.8) |
| Glc$_{IV}$-2 | 75.8 | 4.05 m |
| Glc$_{IV}$-3 | 79.0 or 79.1 | 4.22 m |
| Glc$_{IV}$-4 | 72.0 or 72.1 | 4.16 m |
| Glc$_{IV}$-5 | 79.0 or 79.1 or 79.4 | 4.09 m |
| Glc$_{IV}$-6 | 62.9 | 4.31 m |
| | | 4.57 m |

$^\epsilon$Anomeric proton was partially obscured by solvent (HDO) resonance, coupling constant value obtained from 1D-TOCSY data.
$^\S$Two carbons, δc 72.38 and 72.43.

The structure of CC-00326 was determined to be (13-[(2-O-β-D-glucopyranosyl-3-O-β-D-glucopyranosyl-β-D-glucopyranosyl)oxy] ent-kaur-16-en-19-oic acid-[(6-O-α-D-glucopyranosyl-β-D-glucopyranosyl) ester]). This glycoside contained five sugars and had the relatively uncommon 1→6 α-glycoside linkage between Glc$_{VII}$ and Glc$_I$.

Example 3: Preparation of CC-00342

Preparation of EUGT11 (UDP-Glucosyl Transferase)

The nucleic sequence from EUGT11 was retrieved from GenBank under the accession number AAS07253.1. The synthetic gene was prepared by DNA2.0. NdeI and XhoI cloning sites were introduced for cloning in pET30A+ vector (Invitrogen). The plasmid was named EUGT11_pET30A+.

E. coli BL21 (DE3) cells harboring the EUGT11_pET30A+ plasmid were grown in Overnight Express™ instant LB medium (Novagen) at 20° C. for 24 h. Cells were collected by centrifugation. Frozen cells were mechanically lysed and the EUGT11 lysate was recovered by centrifugation. Sucrose (40 wt %) was added and the resulting lysate was kept frozen before use. Activity of EUGT11 was determined at 1.2 U/mL. The activity is defined as the amount of enzyme that is required for the conversion of Rebaudioside A to Rebaudioside D under the assay conditions.

Preparation of AtSUS (Sucrose Synthase)

The amino acid sequence from AtSUS was retrieved from UniProt under the accession number P49040. The synthetic gene was prepared by DNA2.0. NdeI and XhoI cloning sites were introduced for cloning in pET30A+ vector (Invitrogen). The plasmid was named AtSUS_pET30A+.

E. coli BL21 (DE3) cells harboring the AtSUS_pET30A+ plasmid were grown in Overnight Express™ instant LB medium (Novagen) at 20° C. for 24 h. Cells were collected by centrifugation. Frozen cells were mechanically lysed and the AtSUS lysate was recovered by centrifugation. Sucrose (40 wt %) was added and the resulting lysate was kept frozen before use. Activity was determined at 754 U/mL. The activity is defined as the amount of enzyme that is required for the formation reducing sugars from the reaction of sucrose with UDP using a di-nitro salicylic acid (DNS) assay.

Conversion of CC-00326 (Reb_A_G1) to CC-00342 (Reb_D_G1)

Figure 7:
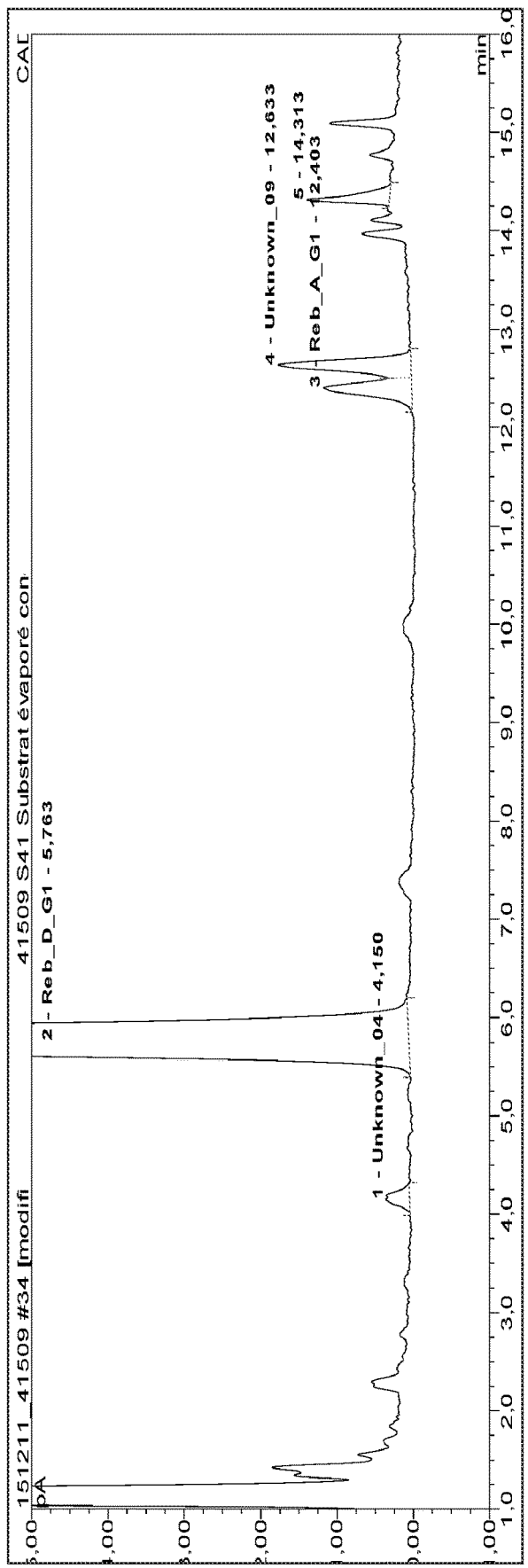
FIG. 7 shows the reaction mixture of the bioconversion from CC-00326 to CC-00342. CC-00342 is referred to as Reb_D_G1.
Figure 8:
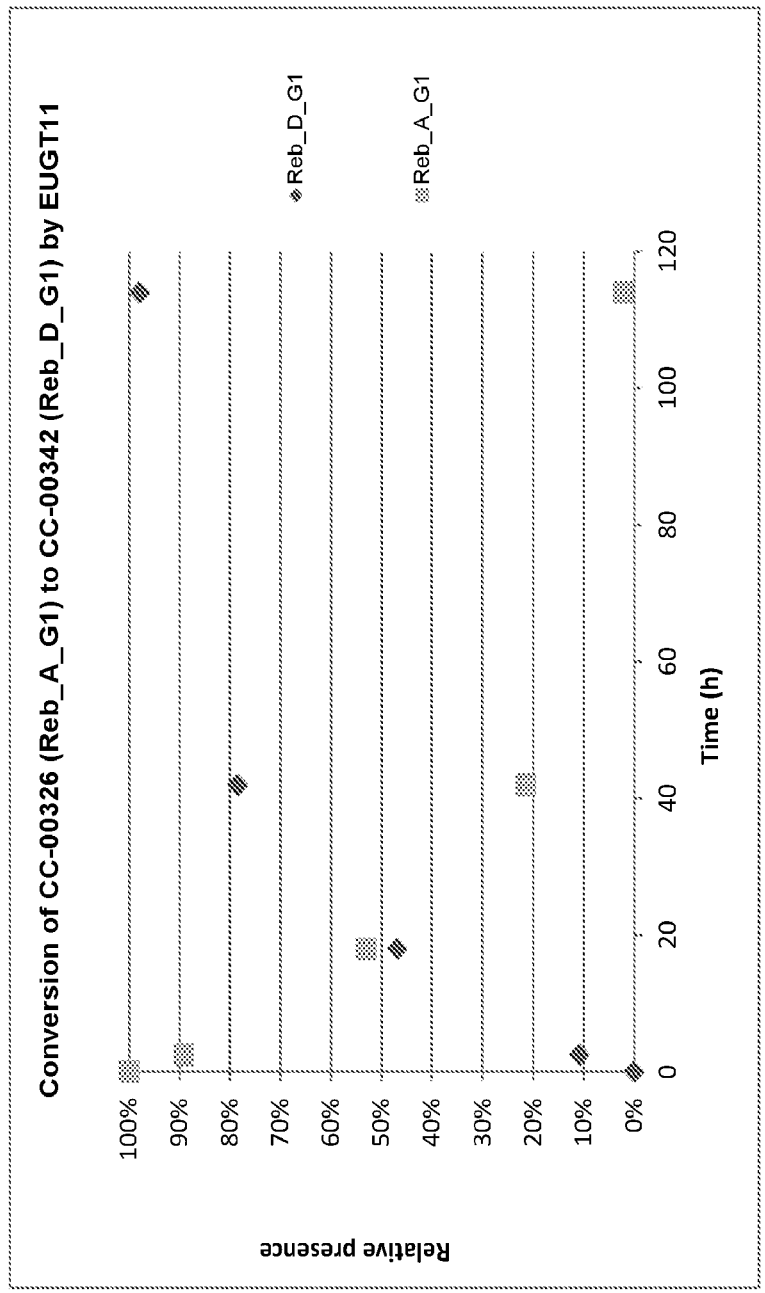
FIG. 8 shows the reaction profile of the bioconversion from CC-00326 to CC-00342. CC-00342 is referred to as Reb_D_G1.

On a 100 mL scale, CC-00326 (Reb_A_G1) was converted to CC-00342 (Reb_D_G1) at 30° C. under the following conditions: 1.0 mM CC-00326; 50 mM Potassium phosphate pH 7.2; 3 mM MgCl$_2$; 0.25 mM of UDP; 100 mM of sucrose; 20 mL of EUGT11 lysate (activity 1.2 U/mL) and 1 mL of AtSUS (754 U/mL). The reaction was performed under sterile conditions and followed by HPLC (method below) by taking samples at regular times (FIGS. 7 and 8). After quenching with 1 vol of ethanol, the crude reaction mixture was used for isolation of CC-00342.

TABLE 1

HPLC Method

| Time (min) | Water containing 0.1% Formic acid | Acetonitrile |
|---|---|---|
| 0 | 80 | 20 |
| 9 | 80 | 20 |
| 13 | 70 | 30 |
| 14 | 70 | 30 |
| 15 | 80 | 20 |
| 20 | 80 | 20 |

Column: KINETEX C18 100A 2.6 µm 4.6×100 mm (Phenomenex Ref.: 00D-4462-EU)
Flow: 0.8 mL/min
Temperature: 45° C.
Detection: Corona Veo SD

Example 4: Isolation and Characterization of CC-00342

HPLC Analysis.

HPLC analyses were performed on a Waters 2695 Alliance System coupled to a Waters 996 Photo Diode Array (PDA) detector. In addition, sample purities were assessed using an ESA Corona Charged Aerosol Detector (CAD). Sample analyses were performed using the method conditions described in Tables 1-3.

TABLE 1

Analytical HPLC Conditions for Preliminary Sample Analysis

| Column | Phenomenex Kinetix C18 (4.6 × 100 mm, 2.6 µm) |
|---|---|
| Column Temperature (° C.) | 55 |
| Sample Temperature (° C.) | Ambient |
| Mobile Phases | (A) 0.1% Formic acid (HCOOH) in water |
| | (B) Acetonitrile (MeCN) |
| Flow Rate (mL/min) | 0.8 |
| Detection | CAD and UV at 210 nm |

| Gradient | | |
|---|---|---|
| Time (min) | % A | % B |
| 0-9 | 80 | 20 |
| 13-14 | 70 | 30 |
| 15-20 | 80 | 20 |

TABLE 2

Analytical HPLC Conditions for Fraction Analysis in Primary Process

| Column | Waters Symmetry Shield RP18 (4.6 × 250 mm, 5 μm) |
|---|---|
| Column Temperature (° C.) | Ambient |
| Sample Temperature (° C.) | Ambient |
| Mobile Phases | (A) Water |
|  | (B) MeCN |
| Flow Rate (mL/min) | 1.0 |
| Detection | CAD and UV at 210 nm |

| Gradient | | |
|---|---|---|
| Time (min) | % A | % B |
| 0-30 | 80 | 20 |
| 30-35 | 5 | 95 |
| 35-45 | 80 | 20 |

TABLE 3

Analytical HPLC Conditions for Final Purity and Retention Time Evaluation

| Column | Phenomenex Synergi Hydro RP (4.6 × 250 mm, 4 μm) |
|---|---|
| Column Temperature (° C.) | 55 |
| Sample Temperature (° C.) | Ambient |
| Mobile Phases | (A) 0.0284% Ammonium Acetate (NH₄OAc) and 0.0116% Acetic Acid (HOAc) in Water |
|  | (B) Acetonitrile (MeCN) |
| Flow Rate (mL/min) | 1.0 |
| Detection | CAD and UV at 210 nm |

| Gradient | | |
|---|---|---|
| Time (min) | % A | % B |
| 0.0 | 85 | 15 |
| 28.5 | 75 | 25 |
| 30.0 | 71 | 29 |
| 36.5 | 70 | 30 |
| 38.5-44.5 | 66 | 34 |
| 46.5-49.0 | 48 | 52 |
| 51.0-57.0 | 30 | 70 |
| 58.0 | 85 | 15 |

Primary Preparative HPLC Method.

Primary processing of material obtained via the process described in Example 3 was performed using a pre-packed Waters Symmetry Shield RP18 column 50×250 mm, 7 μm. The purification process was performed with a Waters Delta Prep LC Model 2000/4000 system coupled to a UV-Vis detector. Details of the primary preparative method are summarized in Table 3.

TABLE 3

Conditions for Primary Preparative HPLC Method

| Column | Waters Symmetry Shield RP18 (50 × 250 mm, 7 μm) |
|---|---|
| Column Temperature (° C.) | Ambient |
| Sample Temperature (° C.) | Ambient |
| Mobile Phases | (A) 80:20 Water/MeCN |
|  | (B) MeCN |
| Flow Rate (mL/min) | 118 |
| Detection | UV at 210 nm |
| Sample Preparation | 25 mg dissolved in 30 mL of water |

TABLE 3-continued

Conditions for Primary Preparative HPLC Method

| Gradient | | |
|---|---|---|
| Time (min) | % A | %B |
| 0 - 25 | 100 | 0 |
| 25 - 35 | 0 | 100 |

Isolation Procedure.

Fractions collected during the processing step were concentrated in vacuo using a Buchi® Rotary Evaporator, Model R-114. The concentrated solution was dried for 48-72 h using the Kinetics Flexi-Dry Personal Freeze Dryer.

MS and MS/MS.

MS and MS/MS data were generated with a Waters QT of Micro mass spectrometer equipped with an electrospray ionization source. The sample was analyzed by negative ESI. The sample (0.1 mg) was diluted with 50:50 ACN:H₂O to a concentration of 0.2 mg/mL for HRMS and MS/MS. Both samples were introduced via direct infusion.

NMR.

The sample was prepared by dissolving 2.27 mg in 130 μL of CD₃OD and NMR data were acquired on a Bruker Avance 500 MHz instrument equipped with a 2.5 mm inverse probe and a 5 mm broad band probe. The $^1$H and $^{13}$C NMR spectra were referenced to the solvent resonance at $\delta_H$ 3.30 ppm and $\delta_C$ 49.0 ppm, respectively.

Results and Discussion

Unless otherwise noted, all solvent ratios are listed as percent by volume (v/v).

Primary Purification of CC-00342.

Analysis was performed using the method described in Table 1. Approximately 25 mg of the material was processed using the primary preparative HPLC method described above. Collected fractions were analyzed by HPLC using the analytical method summarized in Table 1.

Final Batch Preparation of CC-00342.

Figure 9:
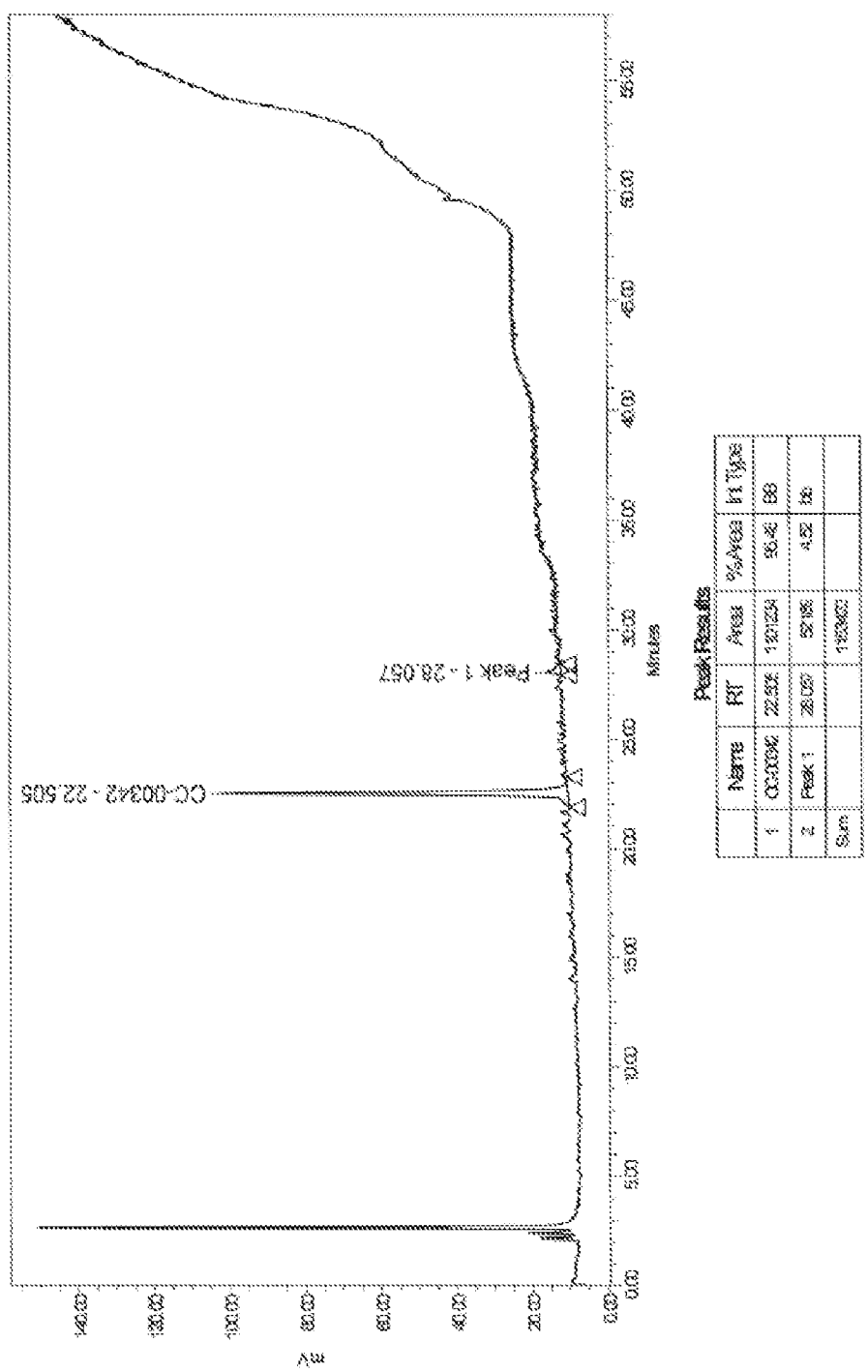
FIG. 9 shows the HPLC trace of purified CC-00342.
Figure 10:
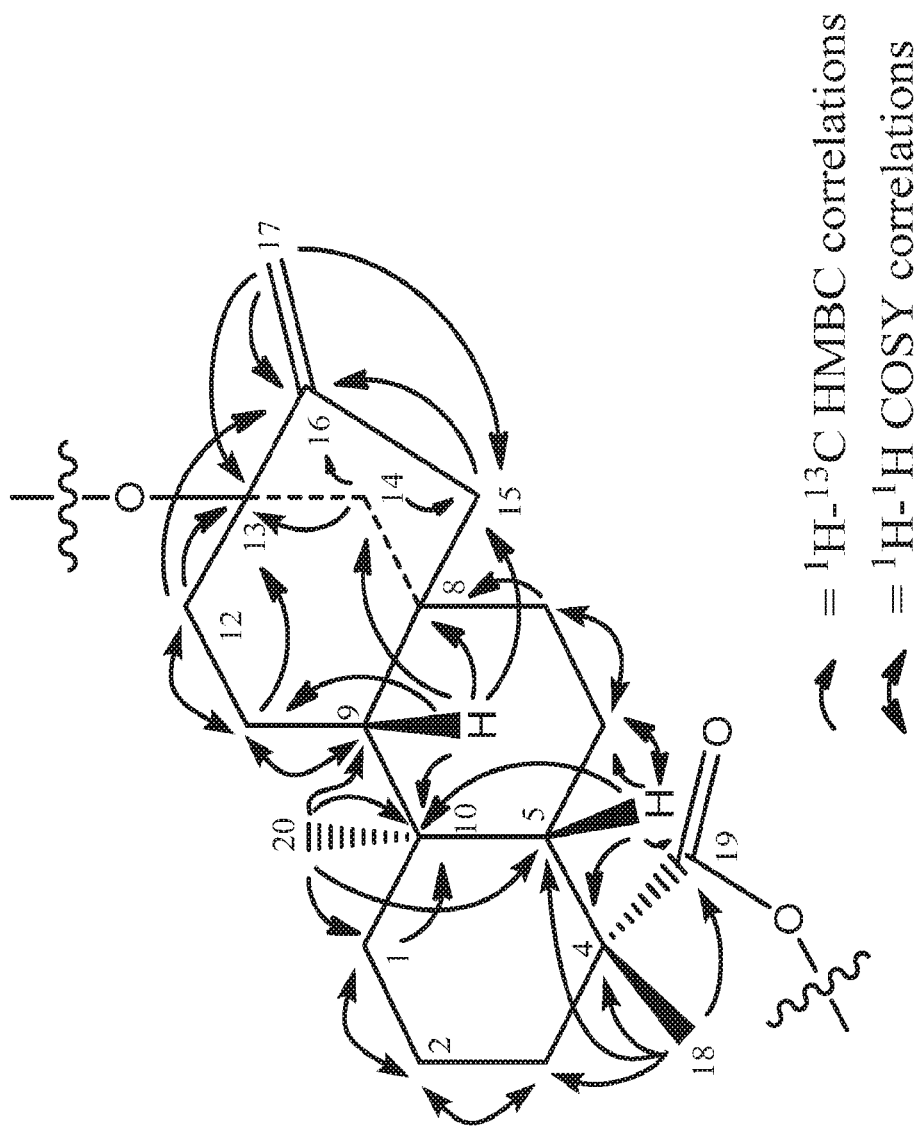
FIG. 10 shows a summary of the HMBC and COSY correlations used to determine the diterpene core of CC-00342.

Pooled fractions were combined and concentrated by rotary evaporation. The concentrated solution was further dried via lyophilization for 48 hours. The final yield of the batch, was 2.3 mg. HPLC analysis was performed using the conditions in Table 3 and is illustrated in FIG. 9. Final purity was determined to be 95.5% by CAD and >99.0% by UV. Retention time was found to be 22.505 min for CAD and 22.441 min for UV.

Mass Spectrometry.

The ESI-TOF mass spectrum acquired by infusing a sample of CC-00342 showed a [M-H]⁻ ion at m/z 1289.4829. The mass of the [M-H]⁻ ion was in good agreement with the molecular formula $C_{56}H_{90}O_{33}$ (calcd for $C_{56}H_{89}O_{33}$: 1289.5286, error: −0.9 ppm) expected. The MS data confirmed that CC-00342 has a nominal mass of 1290 Daltons with the molecular formula, $C_{56}H_{90}O_{33}$. The ion observed at m/z 1403.4869 was due to [M-H+TFA]⁻.

The MS/MS spectrum of CC-00342, selecting the [M-H]⁻ ion at m/z 1289.0 for fragmentation, indicated loss of one glucose unit at m/z 1127.3928 followed by loss of two glucose units at m/z 803.3438. Sequential loss of three more glucose units corresponds to the ions at m/z 641.2920, 479.2570 and 317.1986. The data thus indicated the presence of six glucose units in the structure.

NMR Spectroscopy

A series of NMR experiments including $^1$H NMR (500 MHz, CD₃OD, 300K. 292K), $^{13}$C NMR (125 MHz, CD₃OD, 292K), $^1$H-$^1$H COSY (500 MHz, CD₃OD, 292K), HSQC- DEPT (500 MHz, CD₃OD, 292K)), HMBC (500 MHz, CD₃OD, 292K)), ROESY (500 MHz, CD₃OD, 292K), and 1D TOCSY (500 MHz, CD₃OD, 292K, range of mixing times (40-140 sec)) were acquired to assign CC-00342.

A summary of the $^1$H and $^{13}$C chemical shifts for the aglycone are found in Table 4.

TABLE 4

$^1$H and $^{13}$C NMR (500 and 125 MHz, CD₃OD), assignments of the aglycone.

| | CC-00342 | |
|---|---|---|
| Position | $^{13}$C | $^1$H |
| 1 | 41.4 | 0.85 m |
| | | 1.88 m |
| 2 | 20.4 | 1.42 m |
| | | 1.99 m |
| 3 | 38.7 | 1.04 m |
| | | 2.25 m |
| 4 | 45.1 | — |
| 5 | 58.4 | 1.08 m |
| 6 | 23.5 | 1.87 m |
| | | 1.90 m |
| 7 | 42.9 | 1.42 m |
| | | 1.57 m |
| 8 | 42.7 | — |
| 9 | 55.1 | 0.97 m |
| 10 | 40.6 | — |
| 11 | 21.0 | 1.61 m |
| | | 1.79 m |
| 12 | 38.8 | 1.49 m |
| | | 2.09 m |
| 13 | 88.8 | — |
| 14 | 44.4 | 1.55 m |
| | | 2.23 m |
| 15 | 48.0 | 2.06 m |
| | | 2.13 m |
| 16 | 153.5 | — |
| 17 | 105.4 | 4.82¶ |
| | | 5.21 brs |
| 18 | 29.1 | 1.24 s |
| 19 | 177.9 | — |
| 20 | 17.3 | 0.94 s |

¶Partially overlapped with Glc$_V$ anomeric proton.

A summary of the $^1$H and $^{13}$C chemical shifts for the glycoside at C-19 are found in Table 5.

TABLE 5

$^1$H and $^{13}$C NMR (500 and 125 MHz, CD3OD), assignments of the C-19 glycoside.

| | CC-00342 | |
|---|---|---|
| Position | $^{13}$C | $^1$H |
| Glc$_I$-1 | 94.5 | 5.51 d (8.0) |
| Glc$_I$-2 | 79.3 | 3.80 m |
| Glc$_I$-3 | 77.9-78.5§ | 3.88 m |
| Glc$_I$-4 | 71.4 | 3.45 m |
| Glc$_I$-5 | 77.1 | 3.62 m |
| Glc$_I$-6 | 67.8 | 3.75 m, 3.90 m |
| Glc$_V$-1 | 104.7 | 4.81 d (7.7) |
| Glc$_V$-2 | 75.8 | 3.30 m |
| Glc$_V$-3 | 77.9-78.5§ | ~3.26 - ~3.33 m |
| Glc$_V$-4 | 71.5 or 72.5 | 3.24 or 3.33 m |
| Glc$_V$-5 | 77.9-78.5§ | ~3.26 - ~3.40 m |
| Glc$_V$-6 | 63.3 | 3.66 m, 3.90 m |
| Glc$_{VII}$-1 | 100.1 | 4.83 d (3.6) |
| Glc$_{VII}$-2 | 73.8 | 3.37 m |
| Glc$_{VII}$-3 | 75.3 | 3.65 m |
| Glc$_{VII}$-4 | 71.5 or 72.5 | 3.24 or 3.33 m |

TABLE 5-continued $^1$H and $^{13}$C NMR (500 and 125 MHz, CD3OD), assignments of the C-19 glycoside.

| | CC-00342 | |
|---|---|---|
| Position | $^{13}$C | $^1$H |
| Glc$_{VII}$-5 | 73.4 | 3.63 m |
| Glc$_{VII}$-6 | 62.5 | 3.70 m, 3.76 m |

§Seven carbon resonances in the range of 77.9-78.5 ppm (77.94, 78.01, 78.04, 78.22, 78.29, 78.46 and 78.53), hence chemical shifts could not be unequivocally assigned.

A summary of the $^1$H and $^{13}$C chemical shifts for the glycoside at C-13 are found in Table 6.

TABLE 6

$^1$H and $^{13}$C NMR (500 and 125 MHz, CD₃OD), assignments of the C-13 glycoside.

| | CC-00342 | |
|---|---|---|
| Position | $^{13}$C | $^1$H |
| Glc$_{II}$-1 | 96.9 | 4.76 d (7.8) |
| Glc$_{II}$-2 | 80.6 | 3.59 m |
| Glc$_{II}$-3 | 87.3 | 4.01 t (8.8) |
| Glc$_{II}$-4 | 70.3 | 3.37 m |
| Glc$_{II}$-5 | 77.5 | 3.31 m |
| Glc$_{II}$-6 | 62.7 or 62.8 | 3.65 m, 3.81 m |
| Glc$_{III}$-1 | 103.9 | 4.87 d (8.0) |
| Glc$_{III}$-2 | 76.2 | 3.23 m |
| Glc$_{III}$-3 | 77.9-78.5§ | 3.33 m |
| Glc$_{III}$-4 | 72.4 | 3.10 t (9.3) |
| Glc$_{III}$-5 | 77.9-78.5§ | 3.29 m |
| Glc$_{III}$-6 | 63.6 | 3.59 m, 3.85 m |
| Glc$_{IV}$-1 | 103.9 | 4.75 d (7.9) |
| Glc$_{IV}$-2 | 75.4 | 3.28 m |
| Glc$_{IV}$-3 | 77.9-78.5§ | ~3.27 m |
| Glc$_{IV}$-4 | 71.7 | 3.26 m |
| Glc$_{IV}$-5 | 77.9-78.5§ | 3.46 m |
| Glc$_{IV}$-6 | 62.7 or 62.8 | 3.62 m, 3.91 m |

§Seven carbon resonances in the range of 77.9-78.5 ppm (77.94, 78.01, 78.04, 78.22, 78.29, 78.46 and 78.53), hence chemical shifts could not be unequivocally assigned.

The structure of CC-00342 was determined to be (13-[(2-O-β-D-glucopyranosyl-3-O-β-D-glucopyranosyl)-β-D-glucopyranosyl)oxy] ent-kaur-16-en-19-oic acid-[(2-O-β-D-glucopyranosyl-6-O-α-D-glucopyranosyl)-β-D-glucopyranosyl) ester].

Example 5: Preparation of CC-00345

Preparation of UGT76G1 (UDP-Glucosyl Transferase)

The amino acid sequence from UGT76G1 was retrieved from UniProt under the accession number Q6VAB4. The synthetic gene was prepared by DNA2.0. NdeI and XhoI cloning sites were introduced for cloning in pET30A+ vector (Invitrogen). The plasmid was named UGT76G1_pET30A+.

E. coli BL21 (DE3) cells harboring the UGT76G1_pET30A+ plasmid were grown in Overnight Express™ instant LB medium (Novagen) at 20° C. for 24 h. Cells were collected by centrifugation. Frozen cells were mechanically lysed and the UGT76G1 lysate was recovered by centrifugation. Sucrose (40 wt %) was added and the resulting lysate was kept frozen before use. Activity of UGT76G1 was determined at 2.5 U/mL. The activity is defined as the amount of enzyme that is required for the conversion of Rebaudioside D to Rebaudioside M under the assay conditions.

Figure 11:
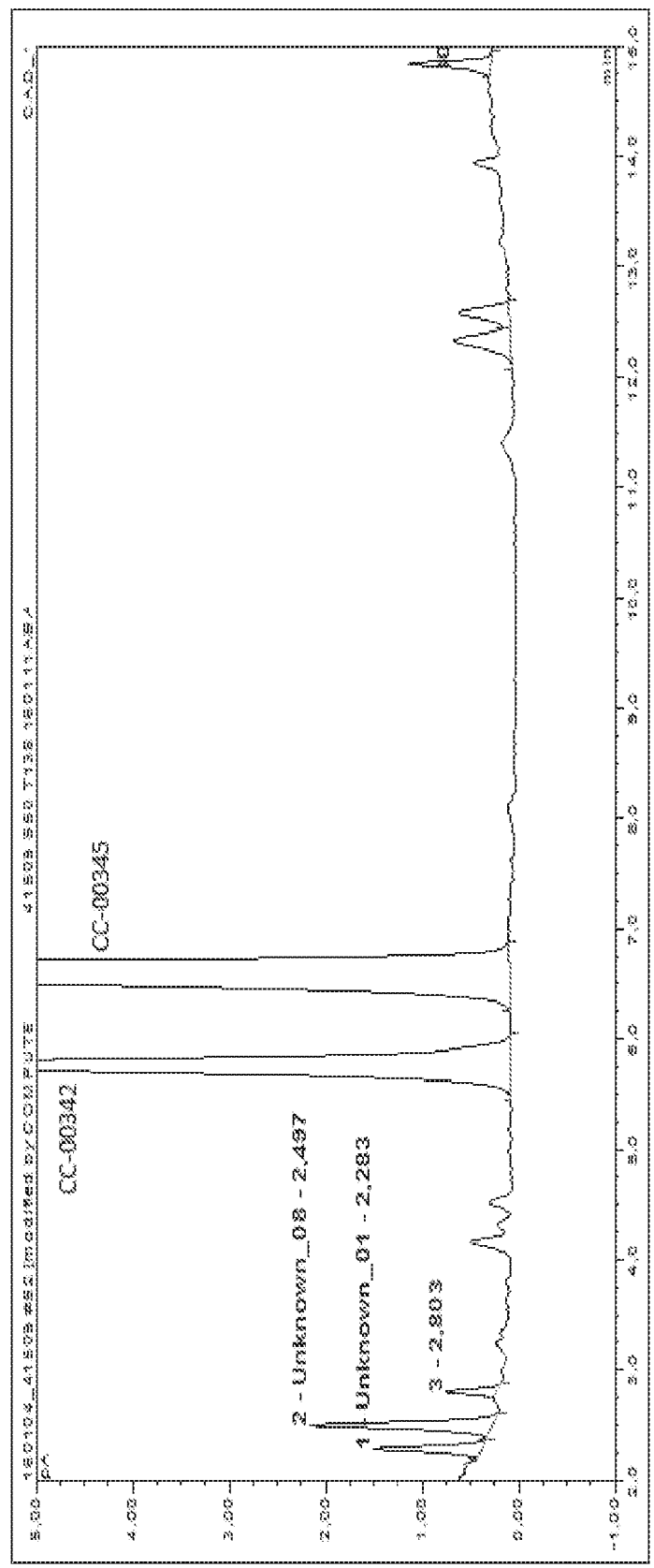
FIG. 11 shows the reaction mixture of the bioconversion from CC-00342 to CC-00345.
Figure 12:
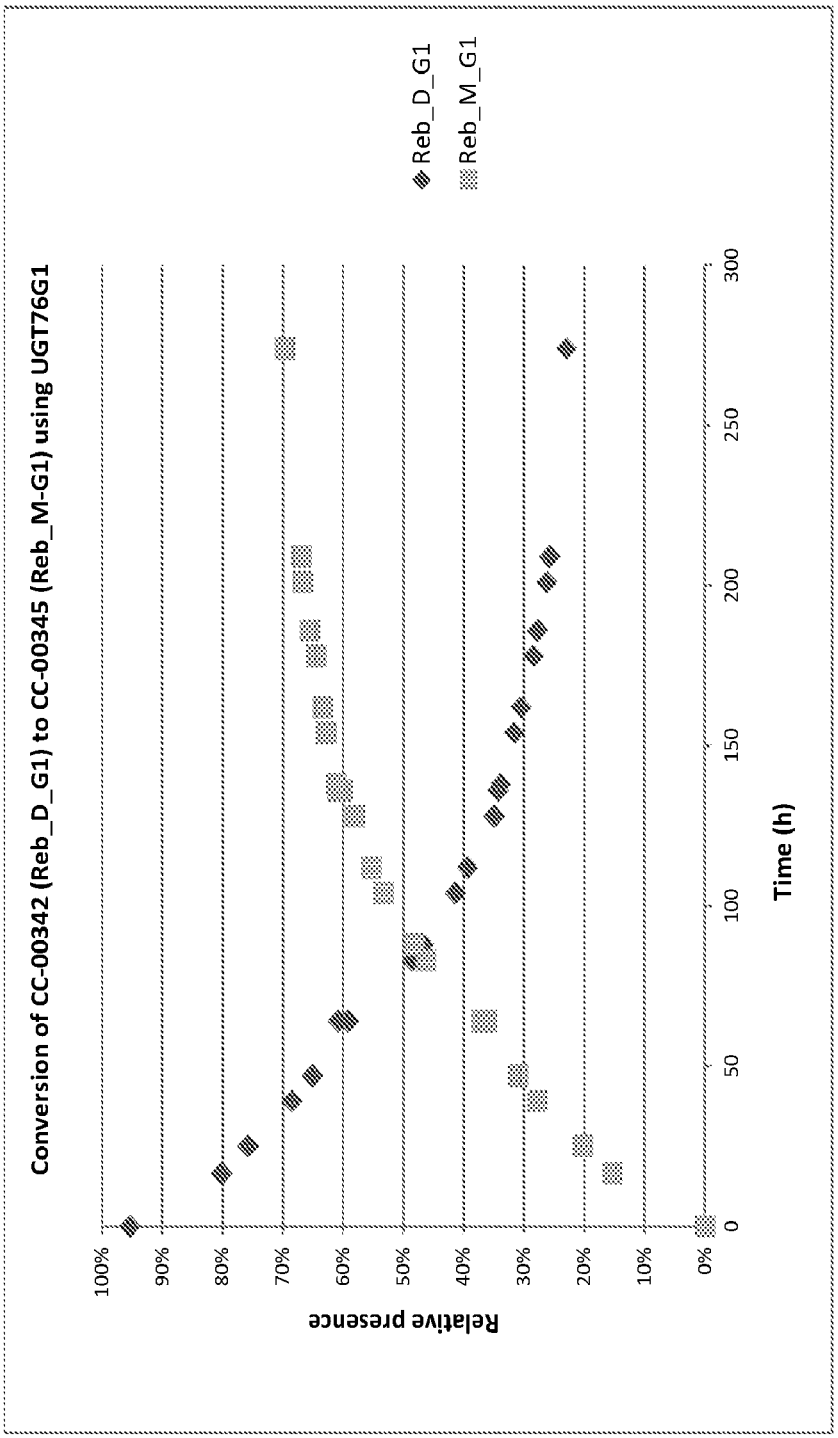
FIG. 12 shows the reaction profile of the bioconversion from CC-00342 (Reb_D_G1) to CC-00345 (Reb_M_G1).

Conversion of CC-00342 (Reb_D_G1) to CC-00345 (Reb_M_G1) On a 75 mL scale, CC-00342 (Reb_D_G1) was converted to CC-00345 (Reb_M_G1) at 30° C. under the following conditions: 1.0 mM CC-00342 (Reb_D_G1); 50 mM Potassium phosphate pH 7.2; 3 mM $MgCl_2$; 0.25 mM of UDP; 100 mM of sucrose; 15 mL of UGT76G1 lysate (2.5 U/mL) and 0.75 mL of AtSUS (754 U/mL). The reaction was performed under sterile conditions and followed by HPLC (FIGS. 11 and 12) by taking samples at regular times using the method described below. After quenching with 1 vol of ethanol, the crude reaction mixture was used for isolation of CC-00345.

Example 6: Isolation and Characterization of CC-00345

HPLC Analysis.

HPLC analyses were performed on a Waters 2695 Alliance System coupled to a Waters 996 Photo Diode Array (PDA) detector. In addition, sample purities were assessed using an ESA Corona Charged Aerosol Detector (CAD). Sample analyses were performed using the method conditions described in Tables 1-2.

TABLE 1

Analytical HPLC Conditions for Preliminary Sample Analysis

| Column | Phenomenex Kinetix C18 (4.6 × 100 mm, 2.6 μm) |
|---|---|
| Column Temperature (° C.) | 55 |
| Sample Temperature (° C.) | Ambient |
| Mobile Phases | (A) 0.1% Formic acid (HCOOH) in water |
|  | (B) Acetonitrile (MeCN) |
| Flow Rate (mL/min) | 0.8 |
| Detection | CAD and UV at 210 nm |

Gradient

| Time (min) | % A | % B |
|---|---|---|
| 0 - 9 | 80 | 20 |
| 13 - 14 | 70 | 30 |
| 15 - 20 | 80 | 20 |

Primary Preparative HPLC Method.

Primary processing of material obtained via the process described in Example 5 was performed using a pre-packed Waters Atlantis dC18 column (50×250 mm, 10 μm). The purification process was performed with a Waters Delta Prep LC Model 2000/4000 system coupled to a UV-Vis detector. Details of the preparative method are summarized in Table 2.

TABLE 2

Conditions for Primary Preparative HPLC Method

| Column | Waters Atlantis dC18 (50 × 250 mm, 10 μm) |
|---|---|
| Flow Rate (mL/min) | 120 |
| Detection | UV at 210 nm |
| Mobile Phases | (A) 85:15 Water/MeCN |
|  | (B) 30:70 Water/MeCN |

Gradient

| Time (min) | % A | % B |
|---|---|---|
| 0 - 50 | 100 | 0 |
| 63 - 67 | 71 | 29 |
| 68 - 78 | 0 | 100 |

Isolation Procedure.

Fractions collected during the final pre-concentration step were filtered through a stainless steel sieve and concentrated in vacuo using a Buchi® Rotary Evaporator, Model R-114. The concentrated solution was dried for 48-72 h using the Kinetics Flexi-Dry Personal Freeze Dryer, followed by vacuum oven drying at 37° C. for 24 h to remove residual moisture.

MS and MS/MS.

MS and MS/MS data were generated with a Waters QT of Micro mass spectrometer equipped with an electrospray ionization source. The sample was analyzed by negative ESI. The sample (0.2 mg) was diluted with 50:50 ACN:$H_2O$ to a concentration of 50 g/mL for HRMS and MS/MS. Both samples were introduced via direct infusion.

NMR.

The sample was prepared by dissolving 4.3 mg in 130 μL of $CD_3OD$ and NMR data were acquired on Bruker Avance 500 MHz instruments equipped with a 2.5 mm inverse probe and a 5 mm broad band probe. The $^1H$ and $^{13}C$ NMR spectra were referenced to the solvent resonance at $\delta_H$ 3.30 ppm and $\delta_C$ 49.0 ppm, respectively.

Results and Discussion

Unless otherwise noted, all solvent ratios are listed as percent by volume (v/v).

Primary Purification of CC-00345.

Approximately 50 mg was processed using the primary preparative HPLC method described above. Collected fractions were analyzed by LC-CAD using the analytical method summarized in Table 1.

Final Batch Preparation of CC-00345.

Figure 13:
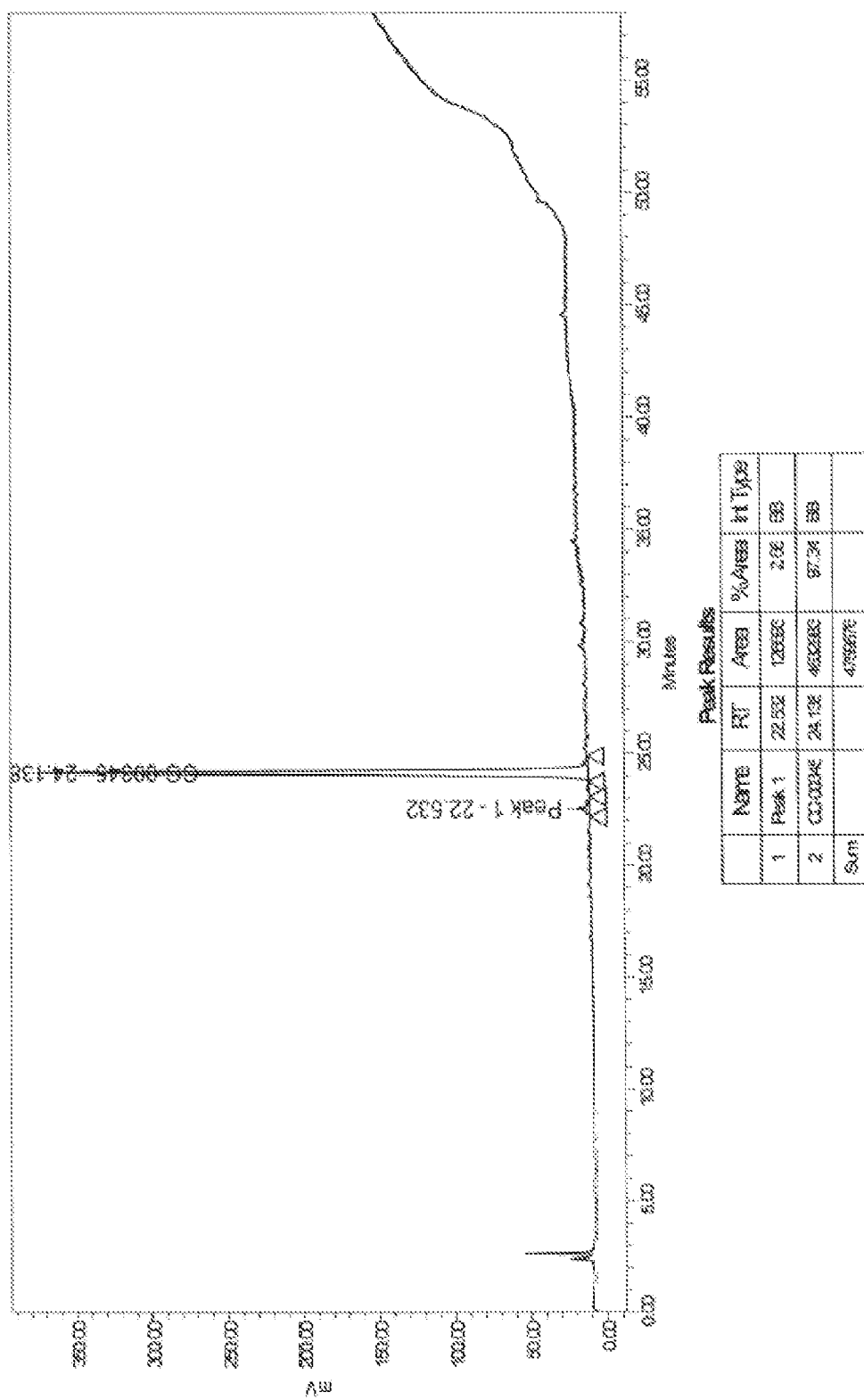
FIG. 13 shows the HPLC trace of purified CC-00345.

Collected fractions were concentrated by rotary evaporation for final isolation. The concentrated solution was further dried via lyophilization for 48 h. The final yield of the batch was 13 mg. The purity was >99% (AUC, CAD). HPLC analysis was performed using the conditions in Table 3, Example 4 and is illustrated in FIG. 13. Retention time was found to be 24.138 min for CAD and 24.080 min for UV.

Mass Spectrometry.

The ESI-TOF mass spectrum acquired by infusing a sample of CC-00345 showed a [M-H]$^-$ ion at m/z 1451.5759. The mass of the [M-H]$^-$ ion was in good agreement with the molecular formula $C_{62}H_{100}O_{38}$ (calcd for $C_{62}H_{99}O_{38}$: 1451.5814, error: 3.7 ppm) expected. The MS data confirmed that CC-00345 has a nominal mass of 1452 Daltons with the molecular formula, $C_{62}H_{100}O_{38}$.

The MS/MS spectrum of CC-00345, selecting the [M-H]$^-$ ion at m/z 1451.0 for fragmentation, indicated sequential loss of two glucose units at m/z 1289.4780 and 1127.4412 followed by loss of two glucose units at m/z 803.3508 and then sequential loss of three glucose units at m/z 641.3007, 479.2548 and 317.213. The data thus indicated the presence of seven glucose units in the structure.

NMR Spectroscopy.

A series of NMR experiments including $^1H$ NMR (500 MHz, $CD_3OD$, 300K and 296K), $^{13}C$ NMR (125 MHz, $CD_3OD$, 296K), $^1H$-$^1H$ COSY (500 MHz, $CD_3OD$, 296K), HSQC-DEPT (500 MHz, $CD_3OD$, 296K), HMBC (500 MHz, $CD_3OD$, 296K), ROESY (500 MHz, $CD_3OD$, 296K), and 1D TOCSY (500 MHz, $CD_3OD$, 296K over a range of mixing times (40-140 msec)) were acquired.

Figure 14:
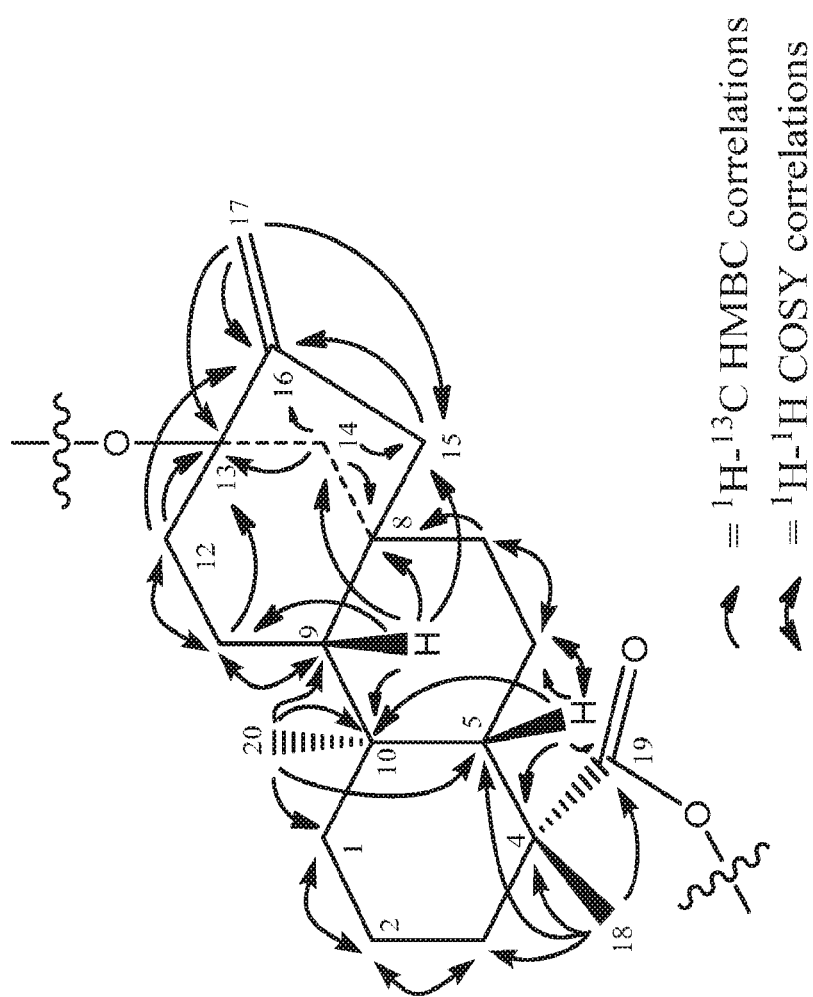
FIG. 14 shows a summary of the HMBC and COSY correlations used to determine the diterpene core of CC-00345.

A summary of the $^1H$ and $^{13}C$ chemical shifts for the aglycone are found in Table 3 and a summary of the key HMBC and COSY correlations used to assign the aglycone region are provided in FIG. 14.

TABLE 3

$^1$H and $^{13}$C NMR (500 and 125 MHz, CD$_3$OD),
assignments of the aglycone.

| | CC-00345 | |
|---|---|---|
| Position | $^{13}$C | $^1$H |
| 1 | 41.0 | 0.86 m |
| | | 1.88 m |
| 2 | 20.2 | 1.43 m |
| | | 2.13 m |
| 3 | 39.0 | 1.07 m |
| | | 2.10 m |
| 4 | 45.1 | — |
| 5 | 58.3 | 1.07 m |
| 6 | 24.3 | 1.83 m |
| | | 1.97 brd (13.3) |
| 7 | 43.1 | 1.41 m |
| | | 1.57 m |
| 8 | 41.8 | — |
| 9 | 55.3 | 0.95 m |
| 10 | 40.5 | — |
| 11 | 20.6 | 1.60 m |
| | | 1.75 m |
| 12 | 39.0 | 1.47 m |
| | | 2.18 m |
| 13 | 89.5 | — |
| 14 | 43.9 | 1.57 m |
| | | 2.21 brd (10.9) |
| 15 | 47.0 | 2.08 m |
| | | 2.11 m |
| 16 | 152.6 | — |
| 17 | 105.4 | ~4.81¶ |
| | | 5.24 brs |
| 18 | 28.4 | 1.24 s |
| 19 | 178.6 | — |
| 20 | 17.1 | 0.95 s |

¶Partially overlapped with Glc$_{II}$, Glc$_{IV}$ and Glc$_{VII}$ anomeric protons.

A summary of the $^1$H and $^{13}$C chemical shifts for the glycoside at C-19 are found in Table 4.

TABLE 4

$^1$H and $^{13}$C NMR (500 and 125 MHz, CD$_3$OD),
assignments of the C-19 glycoside.

| | CC-00345 | |
|---|---|---|
| Position | $^{13}$C | $^1$H |
| Glc$_I$-1 | 95.4 | 5.49 d (8.4) |
| Glc$_I$-2 | 76.7 or 76.8 | 4.00 t (8.8) |
| Glc$_I$-3 | 87.8 | 4.48 t (8.6) |
| Glc$_I$-4 | 70.2 | 3.64 m |
| Glc$_I$-5 | 76.7 or 76.8 | 3.65 m |
| Glc$_I$-6 | 66.7 | 3.68 m, 3.95 m |
| Glc$_V$-1 | 104.0 | 5.04 d (7.7) |
| Glc$_V$-2 | 75.8 or 75.9 | 3.38 m |
| Glc$_V$-3 | 77.6-78.3§ | 3.38 m |
| Glc$_V$-4 | 73.1 | 3.26 m |
| Glc$_V$-5 | 77.6-78.3§ | 3.32 m |
| Glc$_V$-6 | 63.8 | 3.64 m, 3.93 m |
| Glc$_{VI}$-1 | 104.0 | 4.84 d (8.0) |
| Glc$_{VI}$-2 | 75.4 | 3.31 m |
| Glc$_{VI}$-3 | 77.6-78.3§ | 3.56 m |
| Glc$_{VI}$-4 | 71.6 or 71.7 | 3.28 m |
| Glc$_{VI}$-5 | 77.6-78.3§ | 3.53 m |
| Glc$_{VI}$-6 | 62.7 or 62.8 | 3.62 m, 3.94 m |
| Glc$_{VII}$-1 | 99.6 | 4.81 d (~4.0)¥ |
| Glc$_{VII}$-2 | 73.9 | 3.35 m |
| Glc$_{VII}$-3 | 75.2 | 3.66 m |
| Glc$_{VII}$-4 | 71.6 or 71.7 | ~3.29 - ~3.31 m |
| Glc$_{VII}$-5 | 73.3 | 3.65 m |
| Glc$_{VII}$-6 | 62.5 | 3.68 m, 3.75 m |

§Eight carbon resonances in the range of 77.6-78.3 ppm (77.61, 77.76, 77.81, 77.83, 77.85, 77.91, 78.18 and 78.29), hence chemical shifts could not be unequivocally assigned.
¥Partially overlapped with one of the H-17 protons and Glc$_{II}$ and Glc$_{IV}$ anomeric protons.

A summary of the $^1$H and $^{13}$C chemical shifts for the glycoside at C-19 are found in Table 5.

TABLE 5

$^1$H and $^{13}$C NMR (500 and 125 MHz, CD$_3$OD),
assignments of the C-13 glycoside.

| | CC-00345 | |
|---|---|---|
| Position | $^{13}$C | $^1$H |
| Glc$_{II}$-1 | 96.0 | 4.79 d (8.2) |
| Glc$_{II}$-2 | 80.9 | 3.48 t (8.6) |
| Glc$_{II}$-3 | 87.5 | 4.10 t (9.0) |
| Glc$_{II}$-4 | 70.5 | 3.39 m |
| Glc$_{II}$-5 | 77.6-78.3§ | 3.28 m |
| Glc$_{II}$-6 | 62.7 or 62.8 | 3.65 m, 3.78 m |
| Glc$_{III}$-1 | 104.6 | 4.76 d (7.8) |
| Glc$_{III}$-2 | 75.8 or 75.9 | 3.32 m |
| Glc$_{III}$-3 | 77.6-78.3§ | 3.32 m |
| Glc$_{III}$-4 | 72.8 | 3.00 m |
| Glc$_{III}$-5 | 77.6-78.3§ | 3.28 m |
| Glc$_{III}$-6 | 63.8 | 3.56 m, 3.86 m |
| Glc$_{IV}$-1 | 103.8 | 4.79 d (8.2) |
| Glc$_{IV}$-2 | 75.4 | 3.28 m |
| Glc$_{IV}$-3 | 78.7 | ~3.28 m |
| Glc$_{IV}$-4 | 71.6 or 71.7 | ~3.27 - ~3.31 m |
| Glc$_{IV}$-5 | 77.6-78.3§ | 3.62 |
| Glc$_{IV}$-6 | 62.7 or 62.8 | ~3.60 m, ~3.92 m |

§Eight carbon resonances in the range of 77.6-78.3 ppm (77.61, 77.76, 77.81, 77.83, 77.85, 77.91, 78.18 and 78.29), hence chemical shifts could not be unequivocally assigned.

The structure of CC-00345 was determined to be (13-[(2-O-β-D-glucopyranosyl-3-O-β-D-glucopyranosyl)-β-D-glucopyranosyl)oxy]ent-kaur-16-en-19-oic acid-[(2-O-β-D-glucopyranosyl-3-O-β-D-glucopyranosyl-6-O-α-D-glucopyranosyl)-β-D-glucopyranosyl ester].

Example 7: Preparation of CC-00337

Cells of *Leuconostoc mesenteroides mesenteroides* ATCC 11449 were grown at 23° C. in a medium that consisted of: 40 g/L of Sucrose, 20 g/L of Yeast Extract (BIOKAR), 7.82 g/L of KH$_2$PO$_4$, 10.02 g/L of K$_2$HPO$_4$, 0.2 g/L of MgSO$_4$.7H$_2$O, 0.01 g/L of MnSO$_4$.H$_2$O, 0.02 g/L of CaCl$_2$.2H$_2$O and 0.01 g/L of FeSO$_4$. The supernatant after centrifugation was stored frozen and named DS ATCC11449.

Activity Test of DS-ATCC11449

The activity of DS-ATCC 11449 was determined by measuring the amount of reducing sugars (3,5-dinitrosalicylic acid assay) that was produced from sucrose (100 g/L) in 20 mM sodium actetate buffer pH 5.5 in the presence of 0.02 g/L CaCl$_2$ at 30° C. An activity of 10 U/g was determined (1 U/g corresponds to the production of 1 μmol of reducing sugar per minute per g of supernatant under the assay conditions).

DS-ATCC11449 Catalyzed Conversion of Rebaudioside D to CC-00337

Figure 15:
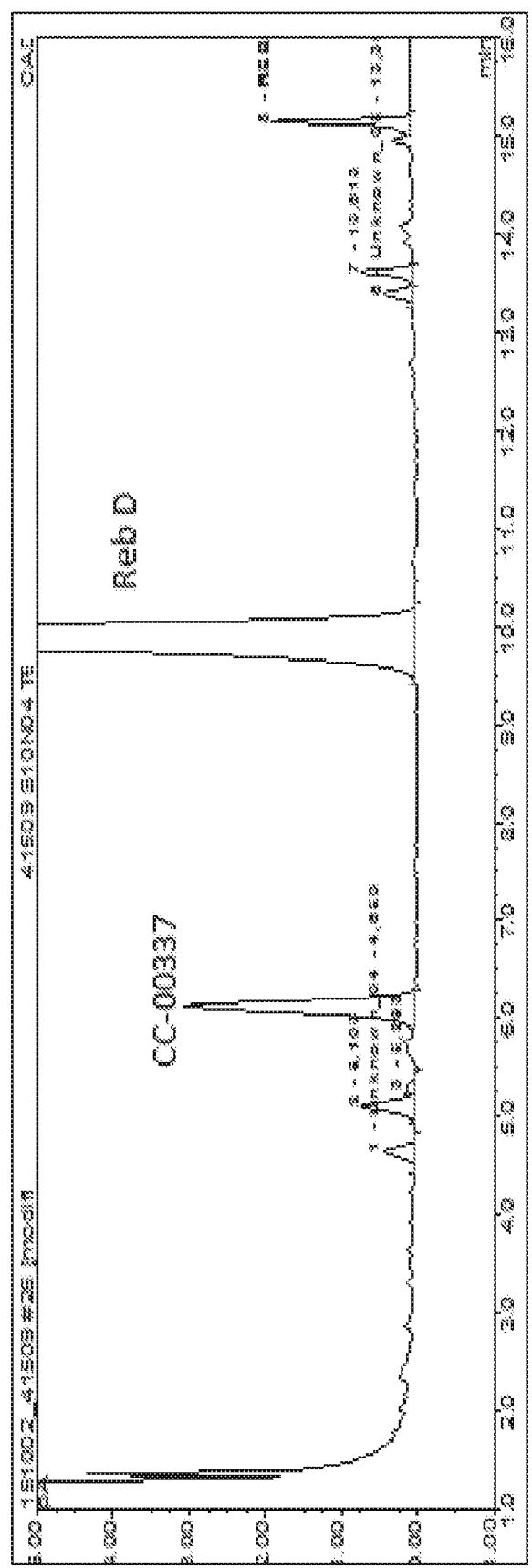
FIG. 15 shows the reaction mixture of the bioconversion from Reb D to CC-00337.
Figure 16:
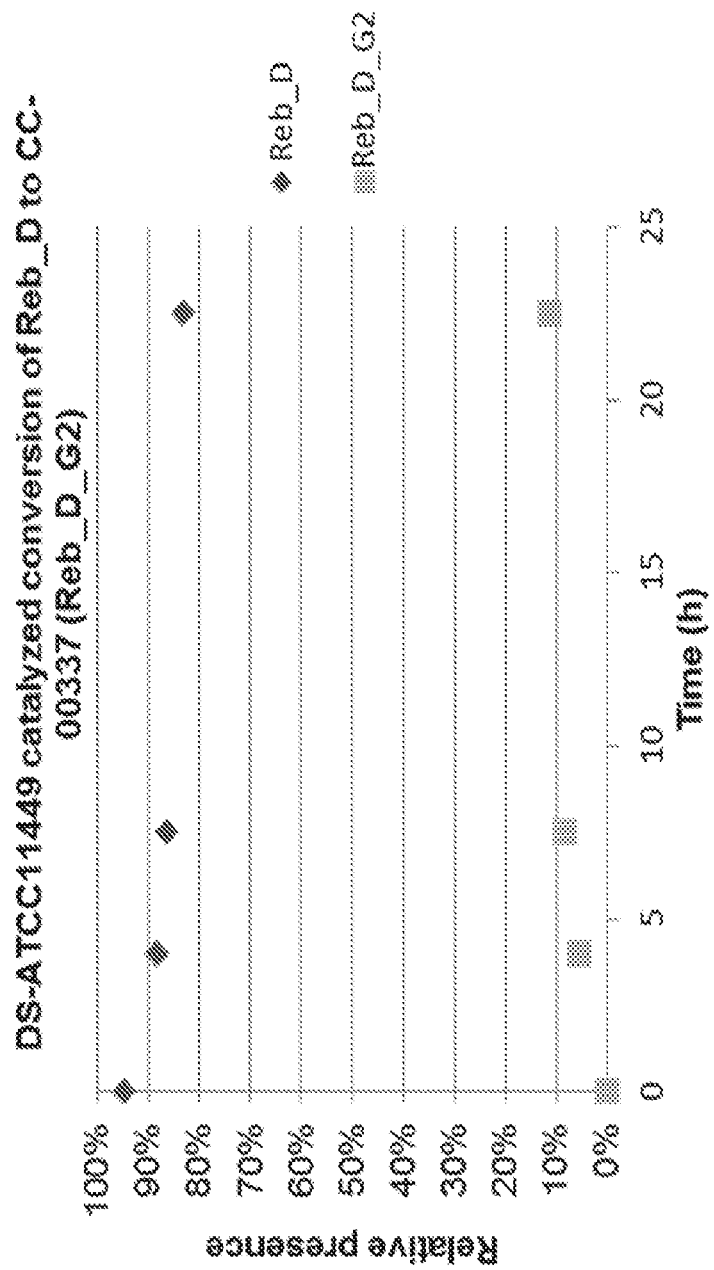
FIG. 16 shows the reaction profile of the bioconversion from Reb D to CC-00337 (Reb_D_G2)

On a 200 mL scale, 1 mM of Rebaudioside D was converted to CC-00337 (Reb_D_G2) at 30° C. under the following conditions: 50 mM Sodium acetate buffer pH 5.2; 0.05 g/L of CaCl$_2$; 250 mM of sucrose; 500 U/L of DS-ATCC11449. The reaction was followed by HPLC using the method described below (FIGS. 15 and 16). After 4.5 h. the reaction was quenched with 100 mL of ethanol and stored at −20° C. overnight. After centrifugation of the suspension, the crude reaction mixture was used for isolation of CC-00337 (Reb_D_G2).

Example 8: Isolation and Characterization of CC-00337

HPLC Analysis.

HPLC analyses were performed on a Waters 2695 Alliance System coupled to a Waters 996 Photo Diode Array (PDA) detector. In addition, sample purities were assessed using an ESA Corona Charged Aerosol Detector (CAD). Sample analyses were performed using the method conditions described in Tables 1-2.

TABLE 1

Analytical HPLC Conditions for Preliminary Sample Analysis and Final Purity Evaluation

| Column | Phenomenex Synergi Hydro RP (4.6 × 250 mm, 4 μm) |
|---|---|
| Column Temperature (° C.) | 55 |
| Sample Temperature (° C.) | Ambient |
| Mobile Phases | (A) 0.0284% ammonium acetate (NH4OAc) and 0.0116% acetic acid (HOAc) in water |
| | (B) MeCN |
| Flow Rate (mL/min) | 1.0 |
| Detection | CAD and UV at 210 nm |

Gradient

| Time (min) | % A | % B |
|---|---|---|
| 0.0 | 85 | 15 |
| 28.5 | 75 | 25 |
| 30.0 | 71 | 29 |
| 36.5 | 70 | 30 |
| 38.5 - 44.5 | 66 | 34 |
| 46.5 - 49.0 | 48 | 52 |
| 51.0 - 57.0 | 30 | 70 |
| 58.0 | 85 | 15 |

TABLE 2

Analytical HPLC Conditions for Primary and Secondary Processes

| Column | Waters Atlantis dC18 (4.6 × 150 mm, 5 μm) |
|---|---|
| Column Temperature (° C.) | Ambient |
| Sample Temperature (° C.) | Ambient |
| Mobile Phases | (A) Water |
| | (B) MeCN |
| Flow Rate (mL/min) | 1.0 |
| Detection | CAD and UV at 210 nm |

Gradient

| Time (min) | % A | % B |
|---|---|---|
| 0 - 20 | 75 | 25 |
| 20 - 35 | 10 | 90 |
| 35 - 45 | 75 | 25 |

Primary and Secondary Preparative HPLC Method.

Primary and secondary processing of material prepare via the method described in Example 7 was performed using a pre-packed Waters Atlantis dC18 column 50×250 mm, 10 μm. The purification process was performed with a Waters Delta Prep LC Model 2000/4000 system coupled to a UV-Vis detector. Details of the preparative method are summarized in Table 3.

TABLE 3

Conditions for Primary and Secondary Preparative HPLC Method

| Column | Waters Atlantis dC18 (50 × 250 mm, 10 μm) |
|---|---|
| Flow Rate (mL/min) | 117 |
| Detection | UV at 210 nm |
| Mobile Phases | (A) 75:25 Water/MecN |
| | (B) MeCN |

Gradient

| Time (min) | % A | % B |
|---|---|---|
| 0 - 35 | 100 | 0 |
| 35 - 45 | 0 | 100 |

Isolation Procedure.

Fractions collected during the final processing step were concentrated in vacuo using a Buchi® Rotary Evaporator, Model R-114. The concentrated solution was dried for 48-72 h using the Kinetics Flexi-Dry Personal Freeze Dryer.

MS and MS/MS.

MS and MS/MS data were generated with a Waters QT of Micro mass spectrometer equipped with an electrospray ionization source. The sample was analyzed by negative ESI. The sample (0.1 mg) was diluted with 50:50 ACN:H$_2$O to a concentration of 0.2 mg/mL for HRMS and MS/MS. Both samples were introduced via direct infusion.

NMR.

The sample was prepared by dissolving 2.1 mg in 130 μL of CD$_3$OD and NMR data were acquired on a Bruker Avance 500 MHz instrument equipped with a 2.5 mm inverse probe and a 5 mm broad band probe. The $^1$H and $^{13}$C NMR spectra were referenced to the solvent resonance at $\delta_H$ 3.30 ppm and $\delta_C$ 49.0 ppm, respectively.

Results and Discussion

Unless otherwise noted, all solvent ratios are listed as percent by volume (v/v).

Primary Purification of CC-00337.

Material was analyzed using the conditions described in Table 1. Approximately 150 mL was processed using the primary preparative HPLC method described above. Collected fractions were analyzed by HPLC using the analytical method summarized in Table 1.

Secondary Purification of CC-00337.

Material from primary purification was reprocessed with conditions summarized above. Fractions were analyzed using the analytical method summarized in Table 1.

Final Batch Preparation of CC-00337.

Figure 17:
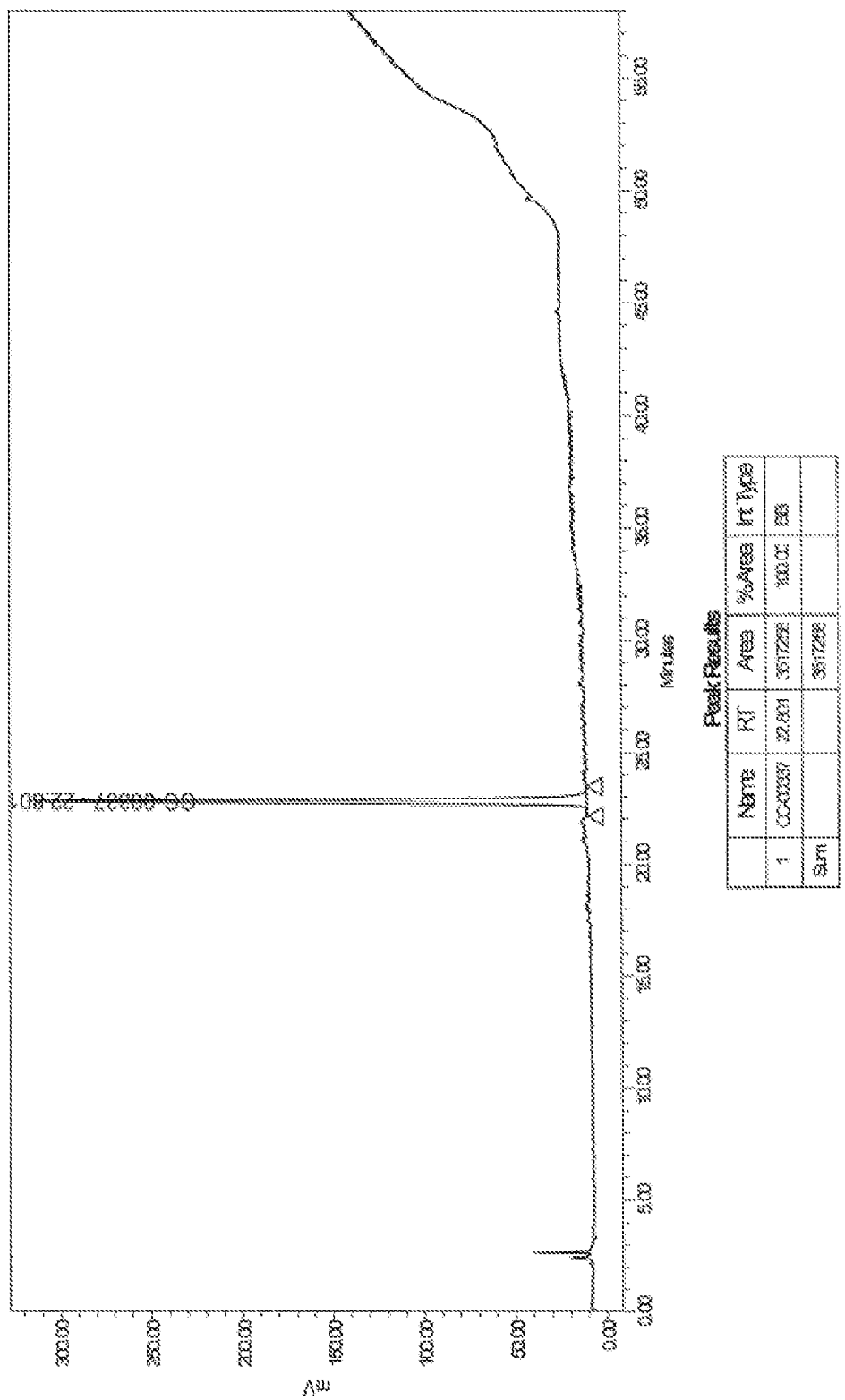
FIG. 17 shows the HPLC trace of purified CC-00337.
Figure 18:
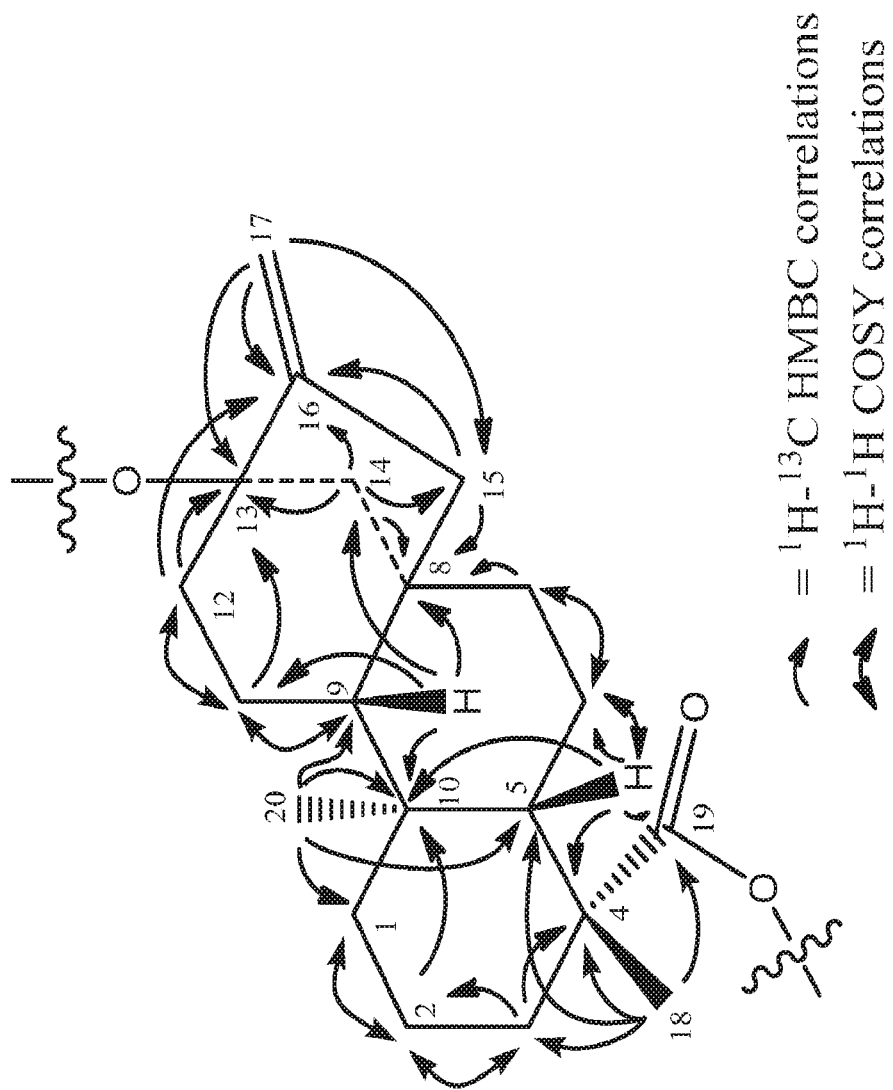
FIG. 18 shows a summary of the HMBC and COSY correlations used to determine the diterpene core of CC-00337.

Collected fractions were combined and concentrated by rotary evaporation for final isolation. The concentrated solution was further dried via lyophilization for 48 hours. The final yield of the batch was 14.1 mg. HPLC analysis was performed using the conditions in Table 1 and is illustrated in FIG. 17. The purity was >99%. The retention time was found to be 22.801 min for CAD and 22.745 min for UV.

Mass Spectrometry.

The ESI-TOF mass spectrum acquired by infusing a sample of CC-00337 showed a [M-H]$^-$ ion at m/z 1289.5004. The mass of the [M-H]$^-$ ion was in good agreement with the molecular formula $C_{56}H_{90}O_{33}$ (calcd for $C_{56}H_{89}O_{33}$: 1289.5286, error: 0.1 ppm) expected. The MS data confirmed that CC-00337 has a nominal mass of 1290 Daltons with the molecular formula, $C_{56}H_{90}O_{33}$.

The MS/MS spectrum of CC-00337, selecting the [M-H]$^-$ ion at m/z 1289.0 for fragmentation, indicated loss of one glucose unit at m/z 1127.4089 followed by loss of two glucose units at m/z 803.3438. The ion at m/z 641.3042 indicated the loss of one more glucose unit followed by loss of two glucose units at m/z 317.1813. The data thus indicated the presence of six glucose units in the structure.

NMR Spectroscopy.

Since CD$_3$OD provides better resolved spectra, complete NMR data was acquired in CD$_3$OD to assign the structure. Thus, a series of NMR experiments including $^1$H NMR (500 MHz, CD$_3$OD at 300K), $^{13}$C NMR (125 MHz, CD$_3$OD at 300K), $^1$H-$^1$H COSY (500 MHz, CD$_3$OD at 300K), HSQC-DEPT (500 MHz, CD$_3$OD at 300K), HMBC (500 MHz, CD$_3$OD at 300K), ROESY (500 MHz, CD$_3$OD at 300K), and 1D TOCSY (500 MHz, CD$_3$OD at 300K over a range of mixing times (40-140 msec)) were acquired to allow assignment.

A summary of the $^1$H and $^{13}$C chemical shifts for the aglycone are found in Table 4.

TABLE 4

$^1$H and $^{13}$C NMR (500 and 125 MHz, CD$_3$OD), assignments of the CC-00337 aglycone.

| | CC-00337 | |
|---|---|---|
| Position | $^{13}$C | $^1$H |
| 1 | 41.6 | 0.85 m |
| | | 1.87 m |
| 2 | 20.5 | 1.42 m |
| | | 1.98 m |
| 3 | 38.5† | 1.04 m |
| | | 2.33 brd (13.6) |
| 4 | 45.2 | — |
| 5 | 58.5 | 1.08 m |
| 6 | 23.0 | 1.86 m |
| | | 1.89 m |
| 7 | 42.6 | 1.43 m |
| | | 1.58 m |
| 8 | 43.0 | — |
| 9 | 55.0 | 0.99 brd (8.0) |
| 10 | 40.7 | — |
| 11 | 21.2 | 1.64 m |
| | | 1.81 m |
| 12 | 38.5† | 1.49 m |
| | | 1.98 m |
| 13 | 88.5 | — |
| 14 | 45.6 | 1.54 m |
| | | 2.27 brd (11.1) |
| 15 | 48.4 | 2.05 m |
| | | 2.15 m |
| 16 | 153.6 | — |
| 17 | 105.8 | 4.87 brs |
| | | 5.28 brs |
| 18 | 29.5 | 1.25 s |
| 19 | 177.6 | — |
| 20 | 17.5 | 0.95 s |

†Two carbon resonances overlapped at 38.5 ppm.

A summary of the $^1$H and $^{13}$C chemical shifts for the glycoside at C-19 are found in Table 5.

TABLE 5

$^1$H and $^{13}$C NMR (500 and 125 MHz, CD$_3$OD) assignments of the CC-00337 C-19 glycoside.

| | CC-00337 | |
|---|---|---|
| Position | $^{13}$C | $^1$H |
| Glc$_I$-1 | 94.0 | 5.55 d (7.9) |
| Glc$_I$-2 | 79.8$^¥$ | 3.78 m |
| Glc$_I$-3 | 78.2 or 78.3$^ϵ$ or 78.4 | 3.70 m |
| Glc$_I$-4 | 71.2 | 3.39 m |
| Glc$_I$-5 | 78.6$^¶$ | 3.45 m |
| Glc$_I$-6 | 62.6-62.9$^§$ | 3.67 m, 3.85 m |
| Glc$_V$-1 | 104.4 | 4.74 d (7.8) |
| Glc$_V$-2 | 74.5 | 3.32 m |
| Glc$_V$-3 | 86.3 | 3.51 m |
| Glc$_V$-4 | 71.8 | 3.51 m |
| Glc$_V$-5 | 77.6 or 77.7 | 3.31 m |
| Glc$_V$-6 | 62.6-62.9$^§$ | 3.68 m, 3.87 m |
| Glc$_{VII}$-1 | 101.3 | 5.18 d (3.8) |
| Glc$_{VII}$-2 | 74.0 | 3.43 m |
| Glc$_{VII}$-3 | 75.1 | 3.65 m |
| Glc$_{VII}$-4 | 71.6 or 71.7 | 3.30 m |
| Glc$_{VII}$-5 | 73.8 | 3.96 m |
| Glc$_{VII}$-6 | 62.6-62.9$^§$ | 3.67 m, 3.81 m |

$^§$Five carbon resonances in the range of 62.6-62.9 ppm (62.56, 62.67, 62.78 and 62.90; two carbon resonances overlapped at 62.56), hence chemical shifts could not be unequivocally assigned.
$^¥$Two carbons, 79.78 and 79.81 ppm.
$^ϵ$Two carbons, 78.31 and 78.34 ppm.
$^¶$Two carbons, 78.55 and 78.58 ppm.

A summary of the $^1$H and $^{13}$C chemical shifts for the glycoside at C-13 are found in Table 6.

TABLE 6

$^1$H and $^{13}$C NMR (500 and 125 MHz, CD$_3$OD), assignments of the CC-00337 C-13 glycoside.

| | CC-00337 | |
|---|---|---|
| Position | $^{13}$C | $^1$H |
| Glc$_{II}$-1 | 97.2 | 4.65 d (7.7) |
| Glc$_{II}$-2 | 79.8$^¥$ | 3.66 m |
| Glc$_{II}$-3 | 88.1 | 3.73 m |
| Glc$_{II}$-4 | 70.4 | 3.37 m |
| Glc$_{II}$-5 | 77.6 or 77.7 | 3.26 m |
| Glc$_{II}$-6 | 62.6-62.9$^§$ | ~3.64 m, 3.83 m |
| Glc$_{III}$-1 | 103.7 | 4.88 d (7.7) |
| Glc$_{III}$-2 | 76.2 | 3.18 t (8.7) |
| Glc$_{III}$-3 | 78.2 or 78.3$^ϵ$ or 78.4 | 3.33 m |
| Glc$_{III}$-4 | 72.5 | 3.11 t (9.3) |
| Glc$_{III}$-5 | 78.6$^¶$ | 3.27 m |
| Glc$_{III}$-6 | 63.6 | 3.57 m, 3.81 m |
| Glc$_{IV}$-1 | 104.3 | 4.66 d (7.8) |
| Glc$_{IV}$-2 | 75.4 | 3.27 m |
| Glc$_{IV}$-3 | 78.2 or 78.3$^ϵ$ or 78.4 | 3.36 m |
| Glc$_{IV}$-4 | 71.6 or 71.7 | ~3.28 m |
| Glc$_{IV}$-5 | 78.2 or 78.3$^ϵ$ or 78.4 | ~3.37 m |
| Glc$_{IV}$-6 | 62.6-62.9$^§$ | 3.63 m, 3.89 m |

$^§$Five carbon resonances in the range of 62.6-62.9 ppm (62.56, 62.67, 62.78 and 62.90; two carbon resonances overlapped at 62.56), hence chemical shifts could not be unequivocally assigned.
$^¥$Two carbons, 79.78 and 79.81 ppm.
$^ϵ$Two carbons, 78.31 and 78.34 ppm.
$^¶$Two carbons, 78.55 and 78.58 ppm.

The structure of CC-00337 was determined to be (13-[(2-O-β-D-glucopyranosyl-3-O-β-D-glucopyranosyl)-β-D-glucopyranosyl)oxy] ent-kaur-16-en-19-oic acid-[(2-O-β-D-glucopyranosyl-(3-O-α-D-glucopyranosyl)-β-D-glucopyranosyl) ester]. This is a new glycoside containing five sugars which has the relatively uncommon 1→3 α-glycoside linkage between Glc$_{VII}$ and Glc$_V$.

Example 9: Sensory Evaluation of CC-00326, CC-00342 and CC-00345

The sensory profiles of CC-00326, CC-00342 and CC-00345 were compared to rebaudioside M.

A trained panel evaluated the various samples. Samples were evaluated using a single sip protocol as follows:

Samples were served at approximately 4° C.

Panelists were instructed to take 1 sip of the sample, hold in mouth for 5 seconds, expectorate, and rate the given attributes A 5 minute break was placed between each sample and panelists were instructed to cleanse their palates with at least 1 bite of unsalted cracker and 2 sips of filtered water Due to limited sample quantity panelists were given 7 mL aliquots of each sample Samples were randomized within each session for each panelist All samples were presented in replicate in each session Samples were evaluated for the following:

Sweet taste intensity: maximum level of sweetness in mouth during 5 seconds

Bitter taste intensity: maximum level of bitterness in mouth during 5 seconds

Overall maximum sweet intensity: maximum sweet intensity experienced from the time the sip is taken up to 1 minute Overall maximum bitter intensity: maximum sweet intensity experienced from the time the sip is taken up to 1 minute Sweet linger intensity: sweet intensity 1 minute after tasting the sample Bitter aftertaste intensity: bitter intensity 1 minute after tasting the sample Data was analyzed with an ANOVA, with Sample as fixed effects and Panelist and interaction as random effects was used to determine significance between the samples for each attribute at the 95% Confidence Level, two-tailed. Fishers LSD was used to determine significant differences between mean scores.

The sensory profile of (i) 400 ppm CC-00326 was compared to (ii) 400 ppm Reb M 80% (rebaudioside M content 80% by weight on a dry basis). Both samples (i) and (ii) were formulated in a water matrix at 4° C. The results are shown in Table 1:

TABLE 1

Means table for CC-00326 compared to Reb M 80% at 400 ppm in water at 4° C.

| Sample | Sweet Intensity In Mouth | Bitter Intensity In Mouth | Overall Max Sweetness | Overall Max Bitterness | Sweet Linger Intensity | Bitter Aftertaste Intensity |
|---|---|---|---|---|---|---|
| Reb M 80% | 8.3 A | 1.6 A | 9.0 A | 2.3 A | 4.3 A | 1.1 A |
| CC-00326 | 6.9 B | 0.8 B | 7.9 A | 1.6 B | 3.9 A | 0.9 A |

*A 3-way ANOVA (Panelist, Sample, Panelist *Sample) was used to compare the sweeteners for each attribute at p <0.05
* Within a column, means with a different letter beside them are significantly different at p <0.05

The sensory profile of (i) 400 ppm CC-00342 was compared to (ii) 400 ppm Reb M 95% (rebaudioside M content 95% by weight on a dry basis). Both samples (i) and (ii) were formulated in a water matrix at 4° C. The results are shown in Table 2:

TABLE 2

Means table for CC-00342 compared to Reb M 95% at 400 ppm in water at 4° C.

| Sample | Sweet Intensity In Mouth | Bitter Intensity In Mouth | Overall Max Sweetness | Overall Max Bitterness | Sweet Linger Intensity | Bitter Aftertaste Intensity |
|---|---|---|---|---|---|---|
| Reb M 95% | 7.0 A | 1.1 | 8.5 A | 2.0 | 4.5 A | 1.0 |
| CC-00342 | 6.7 A | 1.2 | 8.1 A | 2.0 | 3.8 A | 1.0 |

*A 3-way ANOVA (Panelist, Sample, Panelist *Sample) was used to compare the sweeteners for each attribute at p <0.05
*Within a column, means with a different uppercase letter beside them are significantly different at p <0.05

The sensory profile of (i) 400 ppm CC-00345 was compared to (ii) 400 ppm Reb M 95% (rebaudioside M content 95% by weight on a dry basis). Both samples (i) and (ii) were formulated in a water matrix at 4° C. The results are shown in Table 3:

TABLE 3

Means table for CC-00345 compared to Reb M 95% at 400 ppm in water at 4° C.

| Sample | Sweet Intensity In Mouth | Bitter Intensity In Mouth | Overall Max Sweetness | Overall Max Bitterness | Sweet Linger Intensity | Bitter Aftertaste Intensity |
|---|---|---|---|---|---|---|
| Reb M 95% | 7.1 A | 1.3 A | 7.4 A | 1.5 A | 3.6 A | 1.3 A |
| CC-00345 | 6.6 A | 1.3 A | 7.2 A | 2.2 A | 3.9 A | 1.8 A |

A 3-way ANOVA (Panelist, Sample, Panelist *Sample) was used to compare the sweeteners for each attribute at p <0.05
Within a column, means with a different letter beside them are significantly different at p <0.05
**Overall Max Bitterness p = 0.08 at the 90% CL

The invention claimed is:

1. A method for preparing target steviol glycoside CC-00345 comprising contacting a medium comprising a composition comprising starting steviol glycoside CC-00342:

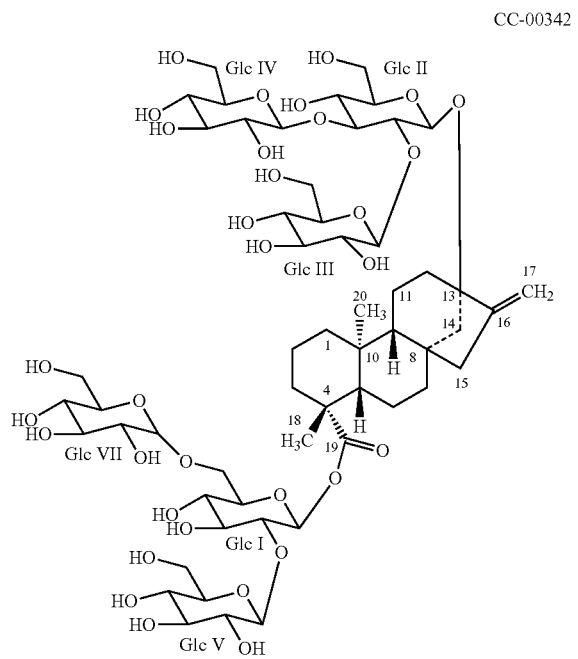

with UGT76G1 to produce a composition comprising target steviol glycoside CC-00345:

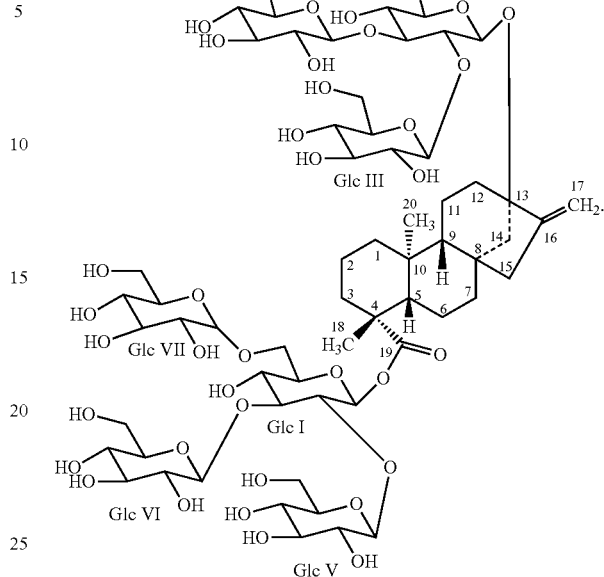

2. The method of claim 1, further comprising separating the target steviol glycoside to provide a separated target steviol glycoside composition.

3. The method of claim 2, further comprising purifying the separated target steviol glycoside composition to provide a purified target steviol glycoside composition comprising at least about 80% target steviol glycoside by weight on a dry basis.

* * * * *